US009080142B2

(12) United States Patent
van den Heuvel et al.

(10) Patent No.: US 9,080,142 B2
(45) Date of Patent: Jul. 14, 2015

(54) PLANT VIRUS DESIGNATED TOMATO MARCHITEZ VIRUS

(75) Inventors: Johannes Franciscus Johanna Maria van den Heuvel, Rotterdam (NL); Paulus Cornelis Maris, Benthuizen (NL); Marinus Verbeek, Andel (NL); Annette Maria Dullemans, Wageningen (NL); René Andries Antonius van der Vlugt, Rhenen (NL)

(73) Assignee: Monsanto Invest B.V., Bergschenhoek (NL)

( * ) Notice: Subject to any disclaimer, the term of this patent is extended or adjusted under 35 U.S.C. 154(b) by 403 days.

(21) Appl. No.: 12/631,259

(22) Filed: Dec. 4, 2009

(65) Prior Publication Data

US 2010/0146659 A1 Jun. 10, 2010

Related U.S. Application Data

(63) Continuation of application No. PCT/NL2008/050076, filed on Feb. 8, 2008, which is a continuation-in-part of application No. 11/759,603, filed on Jun. 7, 2007, now abandoned.

(51) Int. Cl.

| | |
|---|---|
| ***G01N 33/569*** | (2006.01) |
| ***A01H 5/00*** | (2006.01) |
| ***C12N 7/00*** | (2006.01) |
| ***A01H 1/04*** | (2006.01) |
| ***C07K 14/005*** | (2006.01) |
| ***C12N 15/82*** | (2006.01) |

(52) U.S. Cl.

CPC .. *C12N 7/00* (2013.01); *A01H 1/04* (2013.01); *C07K 14/005* (2013.01); *C12N 15/8203* (2013.01); *C12N 15/8283* (2013.01); *G01N 33/56983* (2013.01); *C12N 2770/00021* (2013.01); *C12N 2770/00022* (2013.01)

(58) Field of Classification Search

None

See application file for complete search history.

(56) References Cited

FOREIGN PATENT DOCUMENTS

WO 2006/085749 A1 8/2006

OTHER PUBLICATIONS

Genbank Accession No. EF063642 (2006).*

International Search Report relating to corresponding PCT/NL2008/050076 filed Feb. 8, 2008.

Turina, M., et al., "A Severe Disease of Tomato in the Culiacan Area (Sinaloa, Mexico) is Caused by a New Picorna-Like Vira Species," Plant Disease, vol. 9, No. 8, Aug. 2007, pp. 932-941.

Sequence Listing Accession #: EMBLEF063641 (XP-002488663), 2006.

Sequence Listing Accession #: EMBLEF063642 (XP-002488664), 2006.

Verbeek, M., et al., "Identification and Characterisation of Tomato Torrado Virus, a New Plant Picorna-Like Virus from Tomato," Arch Virol (2007) 152: 881-890.

Verbeek, M., et al., "Tomato Marchitez Virus, a New Plant Picorna-Like Virus from Tomato related to Tomato Torrado Virus," Arch Virol (2008) 153: 127-134.

Sequence Listing Accession #: EMBLEF68174 (XP-00248865), 2007.

Sequence Listing Accession #: EMBLEF68175 (XP-00248866), 2007.

USPTO: Non-Final Office Action regarding U.S. Appl. No. 12/325,310, dated Jun. 11, 2014.

Response to Non-Final Office Action regarding U.S. Appl. No. 12/325,310, dated Sep. 11, 2014.

USPTO: Notice of Allowance and Fees Due regarding U.S. Appl. No. 12/325,310, dated Sep. 30, 2014.

* cited by examiner

*Primary Examiner* — David T Fox
*Assistant Examiner* — Jared Shapiro
(74) *Attorney, Agent, or Firm* — Dentons US LLP

(57) ABSTRACT

The invention relates to the field of virology. The invention provides an isolated plant virus named Tomato Marchitez virus (ToMarV), and components thereof. The invention further relates to methods of producing a ToMarV-resistant plant comprising the steps of identifying a ToMarV-resistant donor plant, crossing said ToMarV-resistant donor plant with a recipient plant, and selecting from an offspring plant a resistant plant.

9 Claims, 19 Drawing Sheets
(4 of 19 Drawing Sheet(s) Filed in Color)

Figure 5

SEQ ID NO: 1

(RNA 2 complete sequence)

TTTAAAAGAATAATTTTATACAATATTTATGTGATCCAAGCCATCACGGAACCTACGTCGTTCCTA
AGATATTGTATCAATTATCTTTGCTGTTACCATTTTGAGTGCACCGTCAACTGAAGGAACCTACGC
CGTTTCCAAGGACAGTGTATCTTTTGTTATTTATTTTGGTTACATCTCTATGTCATTTATTTCTCG
TTTGAATACATCTCTTGAAGAGGAGGCATTTCACAAGCAAGTTGCAGACTCTCAGTGGGTGTGTTC
GGTTGATACAGGCTCTGGCaTAATAAACAGTGATCCAACTCTAGACTTCAAGATTTGTCCCAAGAC
AGGTGGAGCAATTTCTGTTCTATCTGTTTCGTGGCAAAACAATAGCCCTCAACTGGTTCCTGGTCA
TTATTTACTGCGAAGTGGAACTTGGCCAATTACTGGCGTTAAGCTATCTGGCTTACTAGTTCATAG
ATCAATTCGTTTGGAAACCACCAGAAAACTTCTAGAAGCTCAGAGGATTTCTGTATCCCAGCAAGC
ATCTTCTTCCTCCGCTGCTGGTGCTGCAGGAAAACAACCACAAGTAACGCTTACACAATTACAAGA
GGAGCTTGACGAGGCCAAAACTCGCTTAGCTCTCAAAGAGAAAGAGTTACTTGAAGCTCTATCCGA
AATATCCAAATTAAGATTGCAATTGTCCAACCAACTAAGTAATGATGATGTCTTCAGTGGCTGGAC
AGAGGAAGGGCCCAAGTGATAAAAGTGCAGCTGTATCTGAGCAATTAATTGCTCAGATTACAGCTG
CAGTTGAAGCAGGCAACAAAAACCTGCTTCGCAAACTGGGCATGGGTTCATATGGGATTCTCTATG
GCGCCCAAGAGAAGAAAGCCATGGAACTGTTTGACCCTGAGGATGTACATAATATAACCTCATTGT
GGTCTTCATTTAAGAAAACTTTCACTTCCTCGAGGGATCATGGAAATCTATTCTTCCATTTGTATG
GAGTTATGTTTTTCATGGTTCCTCATGTACATGGTGGGGAAGGTAGTGTAAAAATTAGTTTATGTT
CCAGTAATGATCCAACCAATCCTGTTCTGCAGGAGAAGGTTTTGTATTTTTCCGGGGGGGCACAGG
CAGTGTTAATGAGTCCGACCATTACACTACCTTTTGTTAAAAGAGGCCCCATGTTCTACTACACAA
TGGAGTGCCTTGGCACTCGGGCTCAAATTCCTTGCTCAGTAGTGGCCATTTGGAAACAAAAGATTG
ATATCCGTAGTGCCATTTACTCAAAGCAGGAAACAATGTCTTGGGCTATTGAGGCTCTTCACCGAC
CTCAATTTTTCCAGGATAGACAGGAGGCAGCACAGTACATATCATCAGTATATTCTAATGCTACCT
CCTCAGCAACTGATTCAGTGCTTCCGTTTGTGGGAGCACAGCTTGGCGACACAAAGATGAATGTGC
CAAGCGAAGCAAGAATGATCCGGTCCTCCTCGCTCCGGGTGCCCATGCTCAAGGTGCAGAGTAAGC
GGTTTTCCTCAATGGAAATACCATCTACCTCAACTGCACACCTCCTTGGCACAACGCGTGATGAAA
CTGTAATACAGGAGGAAAGTAGGTACGAAGAGGAGGGTGATGATGGGGTTTTGTTCCCCGTTAAAA
AGGCTCAAGGTCTGAACTATTCCCATGTGTGGGATAATCTTGGTATTGAGTCCTTTGTAGATGTTG
AGCTGCCCGAAAACTGGGATGAGCTGTCGGTGAGACAGCAAGTTGCTGCAGCAATGATAGCATTTG
CAAACAAGGGTGTTTGCTTGGTCCCAAAACATATAATCAACCGGGACAAGCACAATATCCACTTGG
AGAATATCACCGAGCACAACTACTTGGTGATACTGGAAAGGTACGGCATTGTGAATGCCGGCTCTC
TGGCCAGAACTGAAAACTGGTACAATCTTACCTTGGCACAGAGAGTGGAAGAGCTAATTTATCAAA
GGGACGATGCATATTTCATGTTTGGTGATAACACCAACCCATATCCTCCCTTTGATTGTTATGATG
GCTTAACGCTCAAAGTTCGCAGTGAGCTAGAGCGTGTGGCAAAGGAGCAGGCGCGCCAAAGATTTT
ACAAGGAGGCGGCCAGGGCTCAGGTGAAAAACAAGGTGGCCCAAACTAGTGTGGAAGAAATACCAT
CCACCTCATTCGCCACAAAGGTTGCCATGGAGAGTGGCAGTGTGGATAGCATGAAAATTGCTATTC
AAGCTGAAGCTGCCAATGAAGCTGTAAGGCCCAATGAAGTTATGTTTGAATTTGGGCAAGAAATGA
ATAATGAAGGTGCGACAGAGCTGGAATTACAACAACCAGCCTGCGTGGCCAGTAACTCCTTCTTCA
ATGTTGGAGTTTTTGAGTTTGCATGGAAGAAAAGCAGTTCTGTTGCTGCTGAGGTGCTATCACTGG
CGCTCCCTGCGGCTCTCTTTGGTAAATCCAAGGAGATGTCAATGGGATCGCAAATGCTAAGGTATT
ATGATGCCGCATTAATTATGTACAAGGTCATCTTGTATATTTCCGGCATGGGTGCAATTTCGGGTC
AGCTGGCCCTGGTTTGGGATGAGTGCAATGTGCTCAACAGAAAGAAGGAGTTCATCAACATTGCCT
CTCTGTATGCCAGCAAACATAGGCTGGTTTCAGCATCTGAACAGAGTAGTGGGGAATTTTGTTTTA
CACCTACGGGTATCGGCAAATTCGTTCCACTTGATCCAGCCTCGGGGGCTTATGATCTGGGTAGCA
TACGGGTGTTTGTGACGCACCCCTTGGCTAGTGCTACTGAATTGGAGAGCATACCTTGTCACATCC
ATCTGCAGTGTAAAGTGTTGTCGACCAACATCATGCAGCCTCCTCGTTTGCGAGCACAGGCACAAT
TTGGTATGAAACCAGACCAGACACACTTTCCACGATTTCCAACAAATCAGGTACTGTTACACTACA

Figure 5

(continued codings)

SEQ ID NO:1 (continued)

ATTGGGGAGTGGCTGCTAGCATGGGTACTACCTTAGTTAGCATCTTCTCTCCGTCAGGCATATATG
AAAGTGACGGTACGCTGCAACCATCCTTGCTTGGAAACATAGCACGCAATTGCAAATGGTGGACTG
GCACTTGCGTGTTTGAGATTTGTATTGAGAAGACTCAGTTCCATTCTGGTAGTTTGGCCATTGGAC
TGGGTACACTGAACACAAGCATGTCCACCCCTCATGACATTTTAAATATGCCGCATGTTATTTGTA
ACCTTGAGATGGGACGAAAGTTCTATTTCAGGTGTACGATAACCAATTGGAATGGGAAAAATCTTT
TGACCACTGGTCGGAAGAGTTCTCTACCGCGGCCCAAGCATATGTCTCACATGAGGTTGTTTGCTA
CAGTCTTGAAACCCCTGGTATCAACTTCAATACATCTAGATACGGTCGGGGTAACAGTGCAGCTTA
AATGCATAGAAGATTTGGTCCTTGGGGGCACTGTGTCTGTTAAACCCATTTACGGACACTGGACTA
AAGGAAAGAATGCTGTGGACTTCCTATTCTCTGAGATGGACTTGTCTCAGCGCAAAGAAATTGAGA
AATTACGCAAGGAAAACGTTGAGACATTTGATGAGAAAGGAAAGAAGCAGCCACAGGTACAAGTGC
CGCTCAGAGACAAGTTTTCATATGGGGCTGTACAATATTTTGTGATGAATTGGAAGGACGAAGAGC
GACTGTTGGTTTTACCATGCGCACCCTGGTCCGTAAGATTCCCTCAGGGGGCACTGGTACAGGAGG
CCATCACATGCCCATTCATTGATTGGTGCTCTTCCTTCTGTTATTGGTCTGGAAGTCTTGAATACA
CCATTATTGTACATAGAGTGCAGACTTCCAATAACATAGGAGGAGTGCTGAACATCACCTTAGATT
CATCAGGGTACCCTTTTCCTCTTGGAATCTCAAAGGGCACCTATGTTGTCTCTGCTGGTGGAGGAG
CAAAATGGGCTTTCACTTATGGTATGAGCGACAACATCTTTTCTTTTGTGGTGCATGATGATGAGT
TTTTTCctAGaCGCCATACCAAAGCCAGAGCAATAGATCCAAATGCTTCAAGAATAATGACTCTGC
AAGATCGACTAGGAAATCTCATAATAAATTTACCAGCCAAAGATGTGATAAGCTCTCTGGAAATCT
TGGTCAAGCCAGGACCTGATTTCAAATTGCAACTGGCTCAAGCTCCTTCAGCAAATCATGAGAAGC
ATTTGGGTGATATGCAAACGCATACCTACCTTTATACTCCTGATTTTTCAGAACTAAGGAGTTTTG
AAAATTAACTATCCTGTACGTGATATAGGAGCCGTGAGTCCGGCATGTGACTCATCATGTGCAGTT
AACATGTGTACTGTGAATAATGTTAACTGTAAGGATAGTTAATTTTAACGGAGAGTACTGACTTTA
ACTAGTTGGGAGTCCGGCTCCATTTGGAGTACCAATGAATCTACATTGGTTAAAGAGATTTGCACG
CCTCTCTTTAAATATGGATCGTGTACCCTGCTTGGTTAGAAAGTACCTTTACTTAGGTTTACAAAG
TACGGGGAGCACTCCCTGGTTAACATAGTGCAGGTGCTATCCCATGATAGTCCTTTAACTCAAGGG
TTGAGTTCGGTTTGCATCTTTTGCCGTGATGAAAGATGAGGTAGCTTCCCCCTTATTGGGAGGCTG
AAACTACACATATGTAGTGGGTTTGACTGAGTCCTATAATCAGTCCGTTTGAAATTCGATAATTTT
CCGTAGCTTGCGTCAAGCTGCTCACGTTAGGGGCGTGAGTGAAGATGCGCCGTACCACGCCTTCCC
CGGCAATGCCAGTGGTTCAGAGCGGGCCCTCAGAATAGAGGTTAAAACTAGTGTGATGGTGTATAT
CACGATAAAAAGTGACACCCGGGTTGTGCTGCGCCTAGTTAACACGAGCACAGGTCCCACCCTATA
GTGGAAGAAACTTGGTTGAGTTTTAAAGAACAACCCGTTTGAGCGACGACAAAGTTCCGTAGCTTG
CGACAAGCTGTTTGTGTTAGGGGCACAAATGAAGTTATAGCACACCACTTCTTCCCTAGGTTCGTC
CAGTGGTTTCACAGTGCTATCCTCAGAAAAGAGGTTAAATCTAGTGTGATGGTGTATATCACGATA
AAGAATGACACCCGGGATGTGCTTCTCCTAGTTAACTCGAGCACGGTTTTCACACCACAGTGAAAC
TATCTTACTGCTTTAAATGTTGTTTGTTTGTTTTACTTGTTTTATTGAGTGTTTAATATCATGCAT
ATTTGCTGTTGAAGGTTCTGTCGATGAGGTCAAATGGATACTCGGGAACTACAGTAACTTTGCATT
TGAATTGTTTTCAATTCAGTGTGTGAGTTTGAATATGTATTTTAAAAAAAAAAAAAAA

Figure 6

SEQ ID NO:2

(RNA 1 complete sequence)

TTAAAAGAGTTATTTTGAGAATATAACCTACGTCGTTATTCACAGACCAAGTCTCTGTTAATCAAA
ATCTCCCTTTAAAACTCATTCTACTTTTACATTTGGCAACATGTCTTTTTCCAAGATGTTCCCCGG
TTTCAACTCAGTTACTGAAAAGTGCGCTACCAGCTCCTCTGGTTCTTTCTTTTCAGAGCTTACTGC
TAGTATTAGTAATTTCTCCCGCACTCTGTCCAATGTTACCAAGGTTTCATCTCAAATTTCTTCTCA
CATTGAAGATTTGAAGCCTTCAGTTACAGATGCTGCTTCTTCCTTTACCAGCACCTGTAACTCTGT
TACTAAATTGTTAGATAAGATAATGACTTTAATTGAACCCTTCATCAAGGCTTACTCTTTTGTCGC
ATCCATGTACAAATCAATTTGTGATATGGTTGCAAAGATTGTTGCAAGCATCAAAGATAAGTTCAC
ACTTGGTTTTAACTGGGTGTTGGACAAATCTGAGGATGTGGATGTTTTAGTTATAGCTTTTCTTAT
TTTTGCAATTTCTATGTTAATAATTGTTTTCATTTGTCCAAGTAGTGTACTAGATGGAGTTGTACA
GATGACTCACATAGTTTTTAATACAGTAGGTAACTTCTTTTCAGCTTTGTACAAATTAGACTGGTT
ACCGACATGGTCCCAAAAGTTTTCAATGATGGCACAAGCCAATGTTCTACCAGGGGAATCCATGTC
ACACTCACCACTTTCACAAGTGGTAGCATCCCTCATAGCCTTTGGGATTTCTACCCTTGTGTTCGT
GGCTGTACCTGGTAGACCCAATGGTCTATCCAACCCGCTATCAAAAATTCTGTACTCAGCGGGAAG
TGGTGCTCAACAGTGCAATCAATTGTTTACCCTGTTCAGGAATATGAAAGATTGTACTTCCCAGGC
CTTTTCCTGGGTTCTGGAAATAATAGTAGACATTTTTGGTTTTAAGAATCCAGTTTTGTCTGCTAT
TAGTGCCACATTGTCTACGGACTTATTCACGTGGATGGAAGAGGTGGATGCAGTGTGTGATCCAGC
ACATCGCTTGGAAAATTTTGCAAACCCTGCATTCACTATCAAGCTCCAACATCTAAGGGAGCAGGC
TCTTAAAATCTCTGCTTACATTGCTACACATCCTGTAGCAGCCTTTATGAGCCACAGGGTAACGGC
AGCAATARCCCATCTTGATAAGATATATGGGGAGAACTGCCAGCACACTGGCGTGGGCCAATACAG
GGCAGAACCTTTTATGGTTCAATGGTATGGTGCCAGTGGTTGTGGGAAATCCACCAGCATGCGGCT
GTTCATCAATGATGTTTTGGACCGCATGGAAGAGCCAAAGTTGAACAGGCTCTATGCTGTGAGTAA
GCGAGATGCTTACTGGTCAAATTATGCCCATCAAACTGCTATCCTGATGGATGACATGGGCGCTCT
GAGAGATGGGGCAGGGCAATGCCAGGACATTAAGGATTTGATAGATATCAAGTCCACTCAACCAGC
CCCCTTGCCCATGGCAGCAGTGGAGGATAAAGGCCGCCACTTTACCTCCCGATATATATTTGCCAC
ATCCAACCTTATCTCAGCTCCTGCTCAGTGTGGTCTAACCTACCCCGATGCTTTTGAGAGAAGACG
GGATGTTCTTGTGGAGTGCAGGAAGGTGGGTGAGTTTAACACTGATGCTCCCACTTCTCACCTTGA
ATTTGATGTGGTTGAGAGCAAAAGACCCCATGCAATAACACACAGGGGTTTGAGCTATGATGATTT
GCTGGAATATGTGGTTGCCAAGTGCAAGGTTCATGCAGAAATCTCAGGAAAACTGTATGGCGCCAC
ATCAGGCAAGGTGGCACAGGTTGATGTGTCACCTGAGGAAATAATAGCATCCATGGATATGTTGAA
TATCCAAGATACCAAGCAGGATGCTAAGCTTCCCGTGGTTGTTGTAAGTGAAGAGGATAGGGTGGC
CTACTCYCAGGAGTTGACAGTGGAAGCTTTGAAATATGCTTATCAGGGTAGTCTGAATCCCGCAGC
ATATTTCCCTCATGACATGCACAAACAGGCCATATTTGATGTGCTAAGTGAATCCGCCaAAGAAAC
ATTCACCAGGTGGGTTAATGACATGCTGTATCAAGGTTGCTGTAATGAGAACTATCGCTGGCTGAT
AAAGAATATCCCAGCTGATTATATCATGCACTTTAAGAGCTTCATCTACGCTTCCACAATCAATGA
GCGTAGCTTTGACGTTCAGAAGCAGCTGCCTGATGGAATGGCGCACCGTGCCATAGATGCTGATGT
GGACACACTGATATGCGTGGAGCAGATGCCTGCCCACGTACAATTCTTGTACACAGCATTTGTGAG
GTATTGGTGCCGCAGAAAGATGGAACAGCCTAGGCAATCCTGGGTGGTAGTTTGCTACCACAGTAT
TGTGGATTATATCAAGAATGCTTGGTATGATTTACCGTACATCTTGAGAGTTCTGATTAAGGCTGG
CCTTATTTTAATTGCACTCAATGGTGCATTTGGGGCTGTCACAGCATTCTGTGCTTGTTGGCAATC
CAACACTTTCCCTTCAGCAGAAGGAAGAGGAGGGATTACCAACGAGTCAAATAGCATCTCCAGCCG
GAAGAACAAGGGAAAGAGCATCTTTGCTCGATCTTTGCTGGCACAAGCCAAGGGTGATATGCTGGA
GAAATGGGCAAGTGATGATGGCTTCATCAATGAAGGATTGAAGAAAAACCTAGTCGTCTTGAGACT
AGGTGAAGGTGTCTACTTCAGAGGCACCTATGTCTGCTCGGGCTGGGTGATGACAGTGGCTCATGC
TTTTTCAAGCCTCCGTGATGGCACAACTTTCTCAATAATACATGCCCAGTCAATTTCCAAGGTGCA
ATACAATGCCAAAACTGCACGGTTCTTGAAGGAGCAAGATATTGTCCTGCTCAATGTTGGAAACCC
CGATGGTCCCAAGCCTGATATTCGCAAACACTTTCCTGTACGGGATGGTGTTtGTTTTTCTAAGGG

Figure 6

(continued codings a)

SEQ ID NO:2 (continued)

CACTCAAGGGGTATGTGTGAGAGCAGTAGCATCAAAGGATGCTTCGCAAGGAAATCTTGAGTACTT
GCGTTTTAATGTGATGATGTCCAAGGGTTACCTTGAAAAGGTAACGTACCAGATGGACTCTAGTTC
CTTTAAACTGGAGTCTCAAGCATCTTATGAGTATCACATGAATGGTGAAAATGGTGATTGTGGTAC
TCTTCTTCTTTTGCCCAACGTGCAAGACAAACAACCATGCATTGTGGGTATTCATTGTGCTTCTTA
TGATGAAGAAGCTGCGCACAAAGGGTTTGTAGCATCCAATGCTACAGCTATTTTCCGAGATCAGTT
GGAAGATCTTCCGACTGGTCCGGTTAAAGTAGCAATGGTAAGGTGCCAGCTCCTTAAGGATCTACG
AGCCAGGGATGCGGCTCTTTTTGAAGAAAAACAGGTGGCTTTTGTTGGCACATTGCCAGCTGAACA
AGCAGCCACGGTTCCCCACAAAACAACGCTGCGAAGGAGTGGCTTGTTTGAAGCTTTTGGGCCTGC
AGAAACTGCTCCATCTATCATTTCAGCTTCAGACAAACGTGGGGAAGGTTTtGATCCGTACGTGGC
TGGCATACAAAAATACAATGAAACAGCACAAAATTTTGATGAGGACATTGCGAGGCTAGCCTATGA
AGGGCTACGTCAAGCAATTTTGCCTGTGCTGCACTCCCAGCGAGTTCCTTTTGGAAAGCCCGTCAC
ACAGAATGAAGATGTGGTGCTCAATGGTGTTGATGGGTTTGACTATTTTGACGGGATGGAGTTGAG
TACCTCTTGCGGGTATCCGTACAACAAGTTGGGTATGGGCACTAGCAAGAGAGAGTTTGTGGAGCC
AAGTGGAGATGGAGATCGAGTCCAACTCAAAAGGACCACTCCAATTTTTGATGACTGGGAGGCTTT
GGATGTGGAAATTCGCAAAGGAAACTTTGTGGAACTGGTCACCACCCAATGTGCCAAAGATGAGCG
CTTGCCGTTGGAAAAGGtTTTTGGGAAGCGGAAAACCCGTTTGTTTGAAATTCTTCCCTTCCATTA
CAATATGTTGGTTAGGAAGTATTTCCTGGATTTTTCCGCCAGTCTGATGGCATCCCACAATGCTCT
GCCATGCAAAGTGGGCATTAATCCTGGAGGTATTGAATGGACTCTGTTGGCTAATGGCTTCAGAGC
AGTCTCTGATACAGGATTTTCTGCTGACTATTCCAGTTTTGATGGGAGAGCTCCCATCTTTGCCTT
TCAATGGTTTTGTGATCTTGTGGATGACTACTATGGATCACCTCCTGGTTCTCCAGACTCCAATGC
CAGACATGTGCTTCTTATGATGGCTTCATGCCATTATACTATTTGTGAGAACAAGGTTTTTAGGTT
GGTGGGAGGTATGCCTTCAGGATTTGCACTCACCGTTATCTTCAACTCTCTTCTCAATGAGTTTTA
TATGCGTTATGCATTTATTTCTCTATTGAGAAGACCACATATAGCAGCTCAAGCTATAGGGTGCAA
ACCCTCTGATTTCAACAAGCTATTTGTGGCAGTCTATGGTGATGACAATCTAGTTGCAGTTCCCAT
GGAATTGCATTGGTATACTCTGCCAGCTATTGCCCAAGAATTGGAGATGGTGAATGTTATTATAAA
GAATGGCATCGACAAGAACATGGATGTTAGCAGTTCCAAAATGCTAGACTTGTCTGAGCTAACATT
TCTAAGCAGAGGTTTTAAGAGGCACCGTCTAGGATACGTTCAAGCTCCTCTGAAATGGGTATCTAT
CATAGAACCAATGTACTGGATAAGGCCTtCTGTTGGTTGTCCCGATGCTCTCGCTATGTTGGAAAA
CATAGACACGGGAGTTAGAGAGGCATTTCACCATGGGCCTCAGGTTTTTGAAAAGTTGGTGACAGA
TGTTCAAAACGCTCTCAAGGAGCGGTGTTTCCCAGCCACCACATTTCCTACATATTTTGAATTGGA
GCAGGACTGGCTGGTGGAGGTTACAGGAAATCCAGCCATTGGGCTCATCAAGGAACTTCATATTGC
AGCTTCAGCTTTTGTGCCTTTGCCCCCAGGCAATACTGTTCTGAATTTTTCTGATGGAGTGCATAC
TTTTGCTGACCGAGTGAGTTTCTGCTCCTCGCGAACAGCTGCTGCACAGCAGTGGGACACCACCAC
TGTTTTGGTGAACTGCACTGGGGCAAAGAGACCCACATGGGTAAGAGGGCCCACCACATGGAGGGA
CTTTGAAGGGCTTATTTGGCCTTACACAATGGCTGCAATCAAGGACCACATCTGCAGCATTGTAAC
CAAAGGGGTGACCAAACCACATGTGGTTTTTGTTTGTGGCAATGGGTATGCTATTGGTCCAGTGTG
CGCTGCATTGTACTGTCTGTCCACTGGCCAATATTCTTCTCAGGATGTTGTTGTGAGATTGAGAAC
CATAGCAGATGTTACAGATCTCAGTCAATATCCAGGAGGTTGTGCCAAGTATCTTCTGAAATGTGC
TGATACAAGAGAAGAAGAGCTTGCAGATACATGTAAAATTGCACAAGCCAAGGGTGAGACACCAGC
ATACATACCTCAAGGAGGATTTTCCCTTGGTAATTTTAGAATTGTGCAAGGGAGAATTGATCTACA
GTTGGCCCAGCGCTTGCCTTTTACAGTGGGACCTTATGGGGGATGGGGTCAACACACTACTAGAGA
GCTTAAGTTGCTGCTCAAGGACATGGAGAAGATATATCAAATTTTAGTCCAAAGAGAGAGCTTCAT
CACTCTCTACTTTGACTATCTCAGTTCAGAGCAGGTGATGTTGTTGGTTGACTTTCTTAGGCTCCA
AGGGTTTTTTCCYCGCCAAAATGATGTGGATTACTTGCTTAAAGCCTTTAAGCTGAGCAAGCAGAG
GCACAATAAGGAAAACTGTCATACGGTTTACTTTAGAAAGCCTTTTCTCTCAAGGAAAATGACCAT

Figure 6

(continued codings b)

SEQ ID NO:2 (continued)

GGGGTCCAAAGAAATTCTGTCCGCAACAGCTGCTGAGTCATTGTTTGGTATGGATGTTTCCGCTAA
TGTGCTCAAGAGTAGGCTACTTCATCTTCAGAAGCCCATAAAGTGTTCATCCATGGAGTTGGCCTT
TAAAATTTATTGTGTCATCCAGGGCCACCTGAGCAAGGAAGTTGTAACTCACTTCCAACGCATGTA
CCAACAAGATCTGACAGAAGGGATCATAGAGAAAGTGATATTGTGGTTAACCGCCACACTGTCGGA
GAGCTTTCCAGTGGATCTTGTTGATGTACCTTTAGGCTTGGATAACATAGAGATCCAGGATAAAGG
TTTTTCCCTAAATCCAAATAATATAAATATGAATGCATGTGATGCCATCTTGTTTCAACTCACTGA
GTGTTACAACCGATCAACAAAGAAACATGTGTTCTGTCGCTACACGACTGCATCCTCTCTTGTTGT
TGCCTATGTGCTTGCACATAGACATCAGACAATTGATGAGTTGCCGTCCTTCTATGCAACACACCC
AGATGTGTTGCTTTTGACACCAATCCTAACAGGCTACAAAGCGCCTTGAGTCGGGCTAAATGACTC
AGCTTGTACATGCAATATGTGTACTGTGAATAATATTGCATGAGGATTAACGGAGAGTACTGACTT
TTGCTAGTCGGGAGTCCGACCCACTATATGGGTACCTGTGAATCTACACGGGTTAGGAGATTTGCA
CGCCTCTCCATAAATATGGTTCGTGTGCCCTGCCTTGGTTAGACAGCCTTCCATGCCGGAAGTAAA
TGGCCTATAACGGAGAGTACTGACTTTAACTAGTTGGGAGTCCGGCTCCATTTGGAGTACCAATGA
ATTTACATTGGTTAAAGAGATTTGCACGCCTCTCTTTAAATATGGATCGTGTACCCTGCTTGGTTA
GAAAGTTCCTTTACTTAGGTTTACAAAGTACGGGGAGCACTCCCTGGTTAACATAGTGCAGGTGCT
ATCCCATGATAGTCCTTTAACTCAAGGGTTGAGTTCGGTTTGCATCTTTTGCCGTGATGAAAGATG
AGGTAGCTTCCCCCTTATTGGGAGGCTGAAACTACACATATGTAGTGGGTTTGACTGAGTCCTATA
ATCAGTCCGTTTGAAATTCGATAATTTTCCGTAGCTTGCGTCAAGCTGCTCACGTTAGGGGTGTGA
GTGAAGATGCGCCGTACCACGTCTTCCCCGGCAATGCCAGTGGTTCAGAGCGGGCCCTCAGAATAG
AGGTTAAAACTAGTGTGATGGTGTATATCACGATAAAAGTGACACCCGGGTTGTGCTGCGCCTAGT
TAACACGAGCACAGGTCCCACCCTATAGTGGAAGAAACTTGGTTGAGTTTTAAAAGAACAACCCGT
TTGAGCGACGACAAAGTTCCGTAGCTTGCGACGAGCTGTTTGTGTTAGGGGCACAAATGAAGTTAT
AGCACACCACTTCTTCCCTAGGTTCGTCCAGATGGTTTCACAGTGCTATCCTCAGAAAAGAGGTTA
AATCTAGTGTGATGGTGTATATCACGATAAAGAATGACACCCGGGGTGTGCTTCTCCTAGTTAACT
CGAGCACGGTTTTCACACCACAGTGAAACTATCTTATTGCTTTAAATGTTGTTTGTTTGTTTTACT
TGTTTTATTGTGTGTTTAATATCATGCATATTTGCTGTTGAAGGTTCTGTCGATGAGGTCAAATGG
ATACTCGGGAACTACAGTAACTTTGCATTTGAATTGTTTTCAATTCAGTGTGTGAGTTTGAATATG
TATTTTAAAAAAAAAAAAAAA

Figure 8

SEQ ID NO: 15

(RNA 1 ToMarV complete sequence)

```
AAAGAATTATATATCAAGATTGCAACCTACGTCGTTGTTCACAGACTACG      50
CCTCTGTTAATTGATATTTGATTCTTGTAAACTTTTCCAACATCTTCTTC      100
TCTTCTTACTCGACCATTATTTAAACTCCTCAATTTTCCAATGGCTTTTT      150
CAAAGATGTTCTCCAAGGTTGCTGGTGTTGATGACGCCAGTTCTTCTTCC      200
ACCACTTCATTCTTTGGTGAACTTTCAAATTCTATTTCCAAATTTTCAAA      250
AGCGGTTAGTAATATTACCACTATGTCACAGAAGATTTCAGATCATCTTG      300
AGGATCTGAAACCATCTGTGACTGATGTGTCCACATCTTTTGTGGCCACT      350
TGTAGTTCACTTAATAAAGTTTTGGACAAAATTGGTGCACTTATAGATCC      400
ATTTCTTAAAGCGTACTCTTTCTTGTCCACAATGTACAAATCTATCAAGG      450
ATATGGTTTTAAAATTGTTTGAGAGTTTGTCCAATAAAGTTAAATTAGGA      500
TTTGCTTGGGTGTTAAATAAAAGTGAAGATGTAGATATAGTTGTATATGG      550
TTTTCTTGTATTTGCTATAACATTGTTAGTGCTTCTATTTGTTTGTCCTA      600
GTGATATTGTTGAGGGTGTTTCTAACACTGTCAAAAATATCTTTTTGATA      650
GTCGGAAACATGTTTTCAAGTCTATACAATTTAGATTGGTTTCCAAAATG      700
GGCCGAACGATTCACCATGGTGGCCCAAGCTAGTATGCTTCCTGGGGAAT      750
CAGTTTCACATACACCAACGTCTCAGTTGATGTCCACAATATTGGCTTTT      800
GGGATTTCGACGTTGGTGTTCATTGCAGTGCCTGGTAGACCAAATGGCTT      850
GAGCAACCCATTGTCCAAAATTCTCTATTCGACAGGAAGTGGTGCTCAGC      900
AGTGCAATCAACTATTCACTCTTTACCGTAATATGAAAGATTGCACCTCC      950
CAGGCTTTCTCATGGGTTCTTGAAATAATAGTCGGCACCTTTGGATTCAA      1000
AAATCCTGTGTTGTCAGCTATAAGTGCAACGCTGTCCACTGATCTGTTCG      1050
AGTGGATGCAGGAGGTTGATGCAGTGTGTGATCCTGCAACGCGCCTTGAG      1100
AACTTTGCCAATAAGGCTTTCCCTACCAAATTGAACCATCTGAGGGAAGA      1150
AGCTCTCAAGATCTCAGCTTACATTGCAACCCATCCAGTTGCGGCCTTCA      1200
TGAGCCACAGGGTTAGTGCTGCCATTGCGCAGTTAGAAAAAGTTTATGCT      1250
GAAAGTTGTAGGCACATGGGCGTGGGCCAGTATCGTATTGAACCTTTTAT      1300
GGTACAATGGTTCGGGTCCAGTGGGTGTGGTAAATCTACATCCATGCGCT      1350
TATTTATTAATGATGTGTTGGACAGAATGGGTGAGCCAAAACTCAATCGG      1400
CTATATGCAGTAAGTAAGAGGGATGCATATTGGTCCAACTATGCTCACCA      1450
AACTGCTATCCTGATGGATGACATGGGAGCATTGCGAGATGGGGCTGGGC      1500
AGTGCCAAGATATTAAAGATCTGATTGATATCAAATCAACACAACCAGCA      1550
CCCTTACCAATGGCCGCAGTTGAGGACAAAGGCAGGCATTTCACCTCCAA      1600
GTATATATTTGCCACATCCAATCTGATCTCAGCTCCTGCCCAATGTGGTC      1650
TTACATATCCAGATGCTTTTGAGCGGAGAAGGGACATCCTGGTGGAGTGT      1700
ATGAAGGAGGGCGAGTTTTCCACTGAAGATCCTACGGGACATCTCAGATT      1750
TAACATAGTGGAGAGCAGAAGACCTCATGCTATCACTCACAGGAATTtGA      1800
CCTATAGTGATCTTTTGGAGTATGTGGTAGCCAAATGTCAGGTACATGCA      1850
GAAGTATCAAAGCAATTGTTTGAAGCTGAATCTGGCATAAGTCCTAAGAT      1900
AGCTCAGGTTCAAGTTTCTGCAGATGATGTGATAGCGTCTGTGGATGGGG      1950
CTAGATTGCGCACCAAGCAAGATGAACCAATATTGGTGCCCACTGTTGTG      2000
AGTGAAAATGATAGAGTGATCTATGCAAGAGAGCTCACGGTAGAGGCATT      2050
GAAATATGCATACCAGGGCAGTTTGGACCCTGAGGAACTTTTTCCTCATG      2100
ACCATCATAAGCAGGCCATGTATGATTCTCTTGATGATGAACATAAAGAG      2150
ATTTTCAACAAATGGAGAGTCAACATGTTGTATAGAGGAGCAGATGCTGA      2200
ACAGTATCGATGGTTGGTACAAAACATTCCTGATGACTATATAATGCACT      2250
TTAAGAGTTTCATTTATGCATCAACCATCTCTGAGAAGAAACTAGCAGTG      2300
CAGACAGAGATGAGGACTGGATTTGCACATTCTTGCATTGATGCAGATGT      2350
TGACACCCTCATATGTATCGAGCAGATGCCACCCTTTGTTCAGTTTTTAT      2400
ATACAGCATTTGTGAGATACTGGTGCAACAAAGTATCAAAAGAGCCAAAG      2450
GAATCATGGATCAAAATTTGCTACCATAAAATCGTTGAATATATCAAGGA      2500
```

Figure 8
(continued codings a)

SEQ ID NO:15 (continued)

```
TACATGGTGGAGCCTTCCCTATGCACTGAGATTGCTCATCAAAGCAGGTC 2550
TGATTATAATGGCTCTTAATGGAGTTTTTGGAGGCATTACAGCATTTTTG 2600
GCGTGCTGGCAGAGTAACTCTTTCCCCAATGCATCGGGCAGAGGAGGTGT 2650
GACCAATGAATCCAACAGTATATCCAGTAAGAAGAACAAGGGTAATAAGC 2700
TCAGAAATCTTCTCGTTGGTCAAAGTTCTCAATCATTGGCACAAGATTGG 2750
GCTGCTGAAGATGGATTTGTAAATCAGAGCCTCAAGAAAAATTTGGTGGT 2800
GTTAAGACTTGGTGAAGGAGTGTACTTTAGAGGCACCTACGTGTGTTCTG 2850
GTTGGATAATGACCGTAGCTCATGCATTCCACAATGCTCGAGATGGTACT 2900
CCATTTACAATCATCCATGCCAATTCTCGATCTAAAGTTCAATACAACGC 2950
CAGAGAATCAAGGATTATTGAGGGCCAAGACATCATTCTGTTGCGCGTTG 3000
GTGATCCAGATGGTCCAAAGCCTGACATCCGTAAACACTTCCCAAGAAGG 3050
GATGAGGTGTGCTTCACAAAGGGCTCACAAGGATTGTGCTGTAGAGCTGT 3100
TGCGTCTACAGATCCACGTCTTGGCAATTTAGAGTTTCTCAAGATGCCAG 3150
TGATGATGTCAAAGGGATACACAGTTAAAGTGGAATATGAACTGAACTCC 3200
TCCAGTTTTAAGATTTGCTCTCAACAATCTTATGAATACCACATAAATGG 3250
GGAAAATGGTGACTGTGGCACGTTGCTACTGTTACCAAGTGTTCAGAATA 3300
AGCAACCTGTGATCGTTGGCATCCACTGTGCATCATATGATGGCGTAGCA 3350
GCTGAACGTGGATTTATCTCTTCAAATGCTACAGCTATCTACAGGGAACA 3400
ACTAGAGGATTTGCCAACTGGGCCGGTCAAAGCAGCAATGGTACGCTGTG 3450
ATATTCTGAAGTCAATTAGAAGCAGAGAAACACAGCTTTTTGAGGAAAAC 3500
CAAGTGTACTACCTTGGAACAGTTCCACAGGAGTTGGCCGCCACAGTTCC 3550
CCACAAGACCACTCTGCGGAAAAGCCAATTGTTTGAAGCATTCGGACCTG 3600
CAGAGACAGCACCATCCATTCTAACAGTTCATGACAAAAGAGGTGATGGT 3650
TTTGACCCCTATGTGGCTGGGGTAATGAAATACAATGAAACAGCTTGTGG 3700
ATTTGATGATGACATTGCCAAACTAGCATTCGAAAATCTCAAGTGCTCGC 3750
TGCTACCTATCATGCGTAGCCAGAAGATCCCTGGGGGACGTCCATGTGAA 3800
AGGGATGAGGATGTAGTGCTCAATGGAATAGATGGATGTGATTACTATGA 3850
TGGCATGGAGCTGAGCACATCTTGCGGATATCCCTTCAACAAGATGGGGA 3900
TGGGGATGAACAAGAGAGAATTTGTGCAATCCACTGGCGAAGGAGAGAGA 3950
GTGGAACTCAAAAGAGACACTCCTGTATTTGAAGCATGGGAAGAGCTAGA 4000
TGTGCAGATTAGGAAAGGCATCCATGTGGATCTGGTCACCACCCAATGCG 4050
CCAAAGATGAACGCCTCCCACTTGAGAAAATCTATGGCAAGAGAAAGACC 4100
AGGCTCTTTGAGATACTTCCTTTCCATTACAACATGTTGGTCAGGAAGTA 4150
TTTTCTTGATTTCTCAGCCACATTGATGGCTTTGCACAATGCTATACCAT 4200
GCAAAGTTGGTATTGATCCTACAAGTTCTGAGTGGACATTGTTGGCAAAT 4250
GGGTTTAGAGCTGTGTCAGACGTGGGATTTTCAGCTGATTATTCCAGCTT 4300
TGATGGAAGAGCACCTGTTTTTGCTTTTCAGTGGTTTTGTGATTTGGTGG 4350
ATGAATACTACGGATCAAAGCCTGGCAGTCCTGATTCCAATGCTCGACAT 4400
GCACTTTTAATGATGGCATCTTGTCATTACACACTGTGCGAGGATAAAGT 4450
GTTTAGGTTGGTTGGGGGCATGCCATCAGGATTTGCACTAACGGTCATCT 4500
TCAATTCTCTCCTCAATGAGTTTTATATGCGATATGCCTTTATATCATTG 4550
TTAAGAAGACCCCATATTGCTGCCAGGGCTATAGGAGTTAAACCAAGTGA 4600
TTTCAATCAGCTATTCATAGCTGTTTATGGAGATGACAATCTTGTTGCTG 4650
TACCATTACATCTCCAGTGGTATTCTCTGCCAAATATAGCACATGAGTTA 4700
GAACTGGTCAATGTAATCATTAAGAATGGTCTTGACAAATCGATGGATGT 4750
TAATGAGGTACAATTTCAAGATTTGTCTGAGCTAACTTTTCTGAGTAGAG 4800
GTTTTAAACGACATGCTCTTGGATACCACATGGCTCCTCTCAAGTGGGTT 4850
TCAATCATTGAGCCCATGTATTGGATAAGACCTGCCCCAGGTTGTCCTGA 4900
CACTCAGGCCATGATGGAAAATGTGGAAACAGGAATACGTGAAGCTTTCC 4950
ATCACGGTCGTGTGGCTTATGACAAGCTTGTCTTAGATGTTCAGACGGCG 5000
```

Figure 8

(continued codings b)

SEQ ID NO:15 (continued)

```
TTGGATGAAAGGGGTTTCAGAGCTGTGATCTTTCCTTCCTATTTGGAAGT     5050
GGAACAGGAATGGATTGCAAAGGTAaCAGGGGATTCAAGTGCCCTGACAA     5100
TTTGTGAAATGGCAAAAGCAGCTATTTCCTATACGCCATTGGACGCAGGT     5150
GAGAAGATCACAAATTTTGAGCGTGATCTGAATTGGTTTGCACCAAACAT     5200
TGGTTTTTGTTCAGCACGTACTGCAGCCCACTACACGTGGGATGAAGGGT     5250
ACATTATTGTCAACTGTACAGGTGCAAaGAAGTCCAATTGGGTTAGAGGT     5300
CCAGCCAACTGGAAGGACTTTGAAGGGAAAATGTGGCCGTACACTATGTC     5350
AGCTATAATGGATGCCCAAAAGAATGTGTTGGCAGGAGGACATGTAGCAA     5400
CCAATGTCGTTTTTGTGTGTGGAAATGGATATGCTGTCGGCCCAATTTGT     5450
GCAGCGCTGATGGCCTTAGCAACAAGGCAATATTGTGTGGAGGACATAAT     5500
AGTTAGATTGCGCACAATTGGAAATGTGCTTGACCTCAATACCTATCCTG     5550
GAGGCTGTGTGCAGTATTTTCTTCAATGTGTGCCTCATGGAGACAAAGTG     5600
GCTCAAAGTGGTGCATCGCTCCACAGTAGTTTTATGCACCAAGGGTTTGA     5650
ATTGGGCAACCTCCGCATTATACATGGTGATTTAGCAAAACAGACAGCAA     5700
TGCGGATGCCATATGTGGTAGGACCACATGGAGGATGGGGAAATTTTTCC     5750
ACACAGGATCTTGAGAGTTTGCTACACTATTTGGAGCAGGGATATGCAGA     5800
GTTAATTCAAAAGAATACAAAACTAACTCTGTATTTCAAAGAGCTGAGTA     5850
TGGAAAATGTGCAACAACTGATAGATTTTGTTAAGCTTCAGGGGTTTTTC     5900
CCAAAAGAAACTACCATTCAGAAGCTCAAAAATTTTGTTGATGCTGAATG     5950
TCTAACATTCAAAGCAAGGAGCTTTAGGCACGTAGTTTTCAAAAAGAAAC     6000
TTTTGAGTTCCACATGGAAAATGTGTGGTGAAAGTATTGTTGCTTCAAGG     6050
TCTGCAGAGAGTCTATTCCCTGGCAATTTGTCTGCTTCCGTATTGAAAAC     6100
ATTATTGGAAAGACACACAAGAAGCATGAGTTGTCAGAGTATGGAGCTTG     6150
CTCTGAAAATATATCTATTAAACTTCCAAGTAATAACAAGTGAGATATTA     6200
AAGAAGTTTGAAGATATATTTCAGGAGAAGATATCCACCACCCTACTAAT     6250
CAAAGTATTCTTGTGGCTTGAGGAGAGTTATCAGACTGAGATCTGTATAG     6300
ATTCTCAGGTGCTCCAGAGGATAAACTCCCAGAAATTCAGAGTGCAGGAA     6350
GGTGGTTTTTATTTGCATCCTGAAGGAATCAACATGAATGCCGTAGATGC     6400
AATAATATTTTCTCTGTGGGAGTCCTATAGCCGAGATAGTAACTCCTATT     6450
CTGTGTCAACTCCCATCAAACTGGGGTGTTTCATTTTCCTTGTCGTGCTA     6500
GATAGTCAAGGCAAGGAAGATCATCCTGTTCGGAGGTTTTCAACGGTTTT     6550
CCTTAAAAACTGTGAAACCATTCTTACAAATTACAAGGAGCCTTGAGTCA     6600
GGCATTATGACTCAATTTGTGCGATATGCATGTGTACTGTTAGTAATGTA     6650
TATCGTTAGGATGGTTTTGTTAAGGGAGAGTACTGTCTTTTAATAGATGG     6700
GAGTCCCCTCCACTTTATGGAGACCAATGAATCTACATTGGTATAGAGGT     6750
TTGCACGCTCCTCTTTAAATAAGTTTCGTGTGCCCTGCTTGGTTAGAAAG     6800
CATGTGGTGATTAACACTACTCGTTTGGAGTATAAGCAATAGACCTCATG     6850
ATGTCTAACTCATGCGTGATTGCTCATGTACGAAATAAATGAGCCGTTTG     6900
GAACTCGATAATTTCCCTTAGCTGCTGCACAGCTGTCACTATTAGGGGTA     6950
GTGGCGAAGTCGTGAGTCCCCTCTTCCTCCCTAGGTTCGTCCAGAGGGTT     7000
CAAAGATTCACCTTCTTTGTCAAGAAGCAATGAATGACACGTGTTGCGTC     7050
GACAAAGCACCGTTCTACGTGGTTAGTAGAAAGTTATATTATATTAGATT     7100
TGTTAGTCAATTGTGTGATTTCTTTCTTAGATTAGGAAGTTTTCCGTGGC     7150
GATAGGAAGGGTTTGTCCTTTTACCTTCTTTGCTATGCTGGACACAAAAA     7200
GATTTTCTTTTCTTTTATTTTAAAAAAAA
```

Figure 9

SEQ ID NO: 16
(RNA 2 ToMarV complete sequence)

AAAGAATTTTAATATATATCTGTCATGCAACCTACGTCGTTGTGCGATCTACGTCATCGCTCGCAG
ATATAAAATTAAATCCTTTTAGCTTGAGAACTACGTCTTCTCATTTTCTTTTCCTTTGTTTTGTTG
TTCTTTATGTCATTCATTGGGCGTTTGAATACATCTGTAGACGAACAAGCTTTTCATCATCAAGTT
GCCACCTCGAATTGGATTTGTTCTGTTGATGTTGGCACCGGTTTGATAAATAGCAATCCTACCCTT
GACTTCAAAGTTGTTCCTCCATCAGGTGGTGCTGTCTCAGTTTTAACCGTTTCTTGGGAGAATTCA
ACGCCACAATTAGTGCCTGGACACTATTTGTTGCGTAGTGGTAATTGGCCCATTAAGAACGTAAAG
CTTTCTGGTTTACTTGTCCATCGTTCAGTGCGTCTTGAAACAACCAGAAAGGTCCTAGAGGAAAAC
AAGGTTTCTATTTCAGCATCATCTTCATCTTCTCCTTCTTCTTCTGACAGTAAAGGCAAGAGTAAA
GTAGAGCAACCCACACGAGAGGATCTCATTAAAGAAGTTGAGGTTCTCAAACGTGAGTTAGAGAGA
TTTCAGAAAGAGTTGGCAAGTCAAAAATCTGAAAATCAGAAACTACAACTTCAACTCTCCAATCAA
GTTAGTAATAATGACATCTTCTCAGGTTGGACTGAAAGTGGGCCCCAGTAATCACCAGCAGGAGGA
AGCCTCCGAGAGGTTGATATCACAAATAACAGCTGCTGTGGAGGCCGGAAACAAAAATTTGCTCAG
AAAGCTTGGCATGGGTTCCTACGGGGTTCTTTATGGTTCCCAAGAGAAGAGAGCAATGGAGTTRTT
TGACCCAGATGATGTATCAAAGATCACATCCCTTTGGTCAACATTCAAACATAAGTTTGTTGAGTC
TAAGGACCATGCAAACTTGTTTTTTCATCTGTATGGTGTTCTTTTCTTCATGGTCCCACATGTTCA
TAGTGGGGAGGGAAGGGTTAAGATAAGTCTTTGTTCAAGTAATGATCCCCTCTCACCGGTAATACA
AGAAAAGACACTGTCCTTGGCCGATGGAGCGCAGGCAGTTCTCATGAGCCCCAGCATAACATTGCC
CTTTCTCAAAAGAGGGCCCATGTTTTACTACACCCTGGAGTGCCAAAATACCAGGGCACAGATTCC
GTGTTCCGTGGTTGCCATATGGAAACAAAAGATTGACACAAGGAGTGCAGtTTATTCACAGCAAGA
AACAATGTCTTGGGCCATAGAAGCACTCAATCGTCCGCAATTTTTCCAGGATAGACAGGAGGCTGC
TCAATATATAGCTTCTGTTTATTCGAGTGGGCAAAGTACTCAAATGGCTCTTGAAAACAAAGCCTT
TGTTGGAGAACAGCTTGGGGGCACAAGAATGGACGTCATGAATGAAAGCACTATGATCCGGAGTTC
ATCTTTGAGAGTCCCAACTCTCAAAGTGCAGAGCAAGCGCTTCCCGTCCATGGAACTGCCGGCTGT
AAGTACATCATCCTTACTCAGCACACGTGAAGAAACAGTTCATGATGAGGATGATTGTGGGGGATT
GTTTCCAGCACCCAAGAAAAAGGGCCAAGCCTTCAACATGGGTGCCATTTGGGATAATTTGGGCAT
GGAGTCGTTCGCACACATTGATTTCCCAGATGATTGGACAGAACGAACAATAGCTCAGCAGGTACA
ATTTATCCTCTTTAGTGAGGCTAAAAGAGGAAACGTTATTGTGCCAAGACATGTTGCAAAGCGGCA
TCTGCATAATATCAATAGGGAGCACATAACCGAGGACAATTATGTAGAAATACTTGAAGGTTATGG
TGTTACCAATATCCAAGGCTTGACTCGCACTTTCAATTGGTATGCTATGTCTCTCAAGGAGAGAGT
TGTGGAGCTCGTCCATCAAAGAGATCATTCCTTCTATATTCAAGGGCAGACTAACAATCCAATGCC
GAATTTTGACTGCTATGATGGATTAACCTTGAAAGAGCGTCAGTTGATTGTGGAGGAGCAAGTGGC
CCAAAGAAGGTCTGAAAGACAAGCACAGGTGACAGCAAGGGGCATAGCTGAAAGTCAGCCTGAAGA
CAGAGTGACTGATTCCTTTGTGTCAACTACCACGATGGAAGATCCCACCAAGCCAGATAAGATAGA
AATTGTTGCAGAGGGAGCAGAAGAAGAAACTCAACCTGGTGATGTTATTTTTGACTTTGGACCAGA
AATGGACACATCCATGGCAGTTGAACTGGATATGCAGCAACCGGTGTGTGTAGCTAGCAATGATTT
CTTCAATGTTGGAGTTTTTGAATTCGTTTGGGAGAAGTCCGCTAATGTTGCTGAGCAAGTAATGAG
CTTGGCTTTGCCCGCTGCCCTATTCTCAAAAAGCAAAGAAACTTCAATGGGTGCGCAAATGCTTAA
GTATTACGATGCAGCTCTAATCATGTACAAAATAATACTTTATGTTTCTGGAGTTGGAGCTATCTC
TGGTCAACTGGCTTTGGTGTGGGATGAATGTAATGTGCTTAATCGAAAGAAGGAATTCATCAACAT
CGCCACATTGTATGCCAGTAAGCACACATTGGTTTCAGCTTCACAACAGAACAGTGAGGAGTTTTG
CTTTACCCCAACAGGGATAGGCAAGTACGTGCCTCTGGATGAAGGTACAGGAGCCACTGATTTAGG
TAGTGTGAGAGTGTTTGTGACACACCCCTTATCTAGTGCAACTGAGTTGAATAGTGTACCATGCCA
TTTGCACTTACAGTGCAAAGTGTTATCAACCAATATACTTCAACCTCCACGAATGATAGCACAGGC
TCAATATGGCATGAAGGCGGGGCAGACATATTTTCCAAGGTTTCCAACTAATCAGGTTTTGTTACA
TTATAATTGGGGGACATCATCCCCAATGGGAACTACATTGGTAAGCATATTTTCACCATCAGGAAT

Figure 9
(continued codings)

SEQ ID NO:16 (continued)

ATATGAGAGTGATGGCACCTTGCAGCCGTCTTTGCTTGGTAACATAGCCAGGAATTGCAAGTGGTG
GACTGGAACTTGTGTTTTTGAAATTTGCATTGAGAAAACCTTGTTTCATTCAGGTAGTCTGGCAAT
TGGACTTGGAACTCTGAACACCAAAATGACCAATGCTCATGATATATTTAACATGCCACATGTGGT
ATGCAATCTTGAAATGGGTCGAAAATTTCGGTTCCGGTGTTCTATTACAAATTGGAATGGAAAAAA
TTTGCTTTCCACAGGGCGAAAGAGTTCCTTGCCAAGACCACAGCACTTTTCCCACTTGCGCTTGTT
TGCAACGGTAATGAAGCCACTCGTTTCAACGTCCATACATCTGGATTCCGTTGGTGTCACAGTGCA
GTTGAAGTGCCTTGAAAATCTTACTTTGGGTGGCACAGTATCTGTGAAACCAATATATGGGCATTG
GACAAAAGGCAAAAGCTCAGTTGATTTCCTTTTCTCTGAAATGGATTTATCACAGCGTAAGGAAAT
TGAAAAGTTGAGAAAGGACAACATTGAGGAGTACCAGGAGAAAGGCAAAGATCCGCCCAAGAAGGC
TCAAAGTATTCTGTCCATAAGAGAGAAATTTTCCTATGGTGCTGTACAATATTTCTGCATGGGTTG
GAAGGATGACGAAAGATTGTTGGTAATTCCTTGTGCACCATGGTCCATAAGGTTTGAAGGGCACAG
TCCTGTTAAGGAGGCAATCACTTGTCCATTTATAGATTGGTGTACATCATTTTGTTATTGGTCAGG
TAGTTTGAATTATTCAATTGTGATACACAGAGTACAATCCAGTCCTAATGTTGGAGGTGTACTAAA
TGTTGCTTTTGATGCCTCAGGCTATCCTTTTCCAGCTGGGCTTAATAAAGGAAATTATGTGGTATC
AGCAGGTGGAGGCACAAAATGGGATTTTTCATACGGTGTGGCAACAAATACGTTCTCATTCACTGT
GCAAGATGATGAGTTTTTCCCAAGGCGGCATACAAGGATGAGGGAATTCTCAAGCAAGCAATCCCG
CATCATGTCACTACAGGATAGGCTTGGAAATCTGATCATAAATTTGCCTCCTTCCGCCATAGTGAG
TTCCATTGAGATACTTATATCTCCTGGACTTGATTTCAAGTTGGAGTTGGCCCAACCTCCTTCTGC
CAACCATGAAAAATATCTTGGCAATATGCAAACTCACACCTATCAGTATACCTCAGATTTTTCTGA
GCTACGTGATTTTGCGATTTGAAAAAGTACCATGCTACTGGGTATATAGTAGCCAAATACACTTAT
CTACGTGTACTGTTAGTAGTAGCTAAGTGGTGTTTGTTTGCAATGATAAGGGAGAGTTAAGGGAGA
GTACTGTCTTTTAATAGATGGGAGTCCCCTCCACTTCATGGAGACCAATGAATCTACATTGGTATA
GAGGTTTGCACGCTCCTCTTTAAATAAGTTTCGTGTGCCCTGCTTGGTTAGAAAGCATGTGGTGAT
TAACACTACTCGTTTGGAGTATAAGCAATAGACCTCATGATGTCTAACTCATGCGTGATTGCTCAT
GTACGAAATAAATGAGCCGTTTGGAACTCGATAATTTCCTTTAGCTGCTGTACAGCTGTCACTATT
AGGGGTAGTGGCGAAGTTGTGAGTCCCCTCTTCCTCCCTAGGTTCGTCCAGAGGGTTCAAAGATTC
ACCTTCTTTGTCAAGAAGCGATGAATGACACGTGTTGCGTCGACAAAGCACCGTTCTACGTGGTTA
GTAGAAAGTTATATTATATTAGATTTGTTAGTCAATTGTGTGATTTCTTTCCTAGATTAGGAAGTT
TTCCGTGGCGATAGGAAGGGTTTGTCCTTTTACCTTCTTTGCTATGCTGGACACAAAAAGATTTTC
TTTTCTTTTATTTTAAAAAAAA

SEQUENCE LISTING

```
<160> NUMBER OF SEQ ID NOS: 16

<210> SEQ ID NO 1
<211> LENGTH: 5404
<212> TYPE: DNA
<213> ORGANISM: Artificial Sequence
<220> FEATURE:
<223> OTHER INFORMATION: DNA equivalent of the ToTV-E01 RNA 2 genome

<400> SEQUENCE: 1

tttaaaagaa taattttata caatatttat gtgatccaag ccatcacgga acctacgtcg     60
```

-continued

```
ttcctaagat attgtatcaa ttatctttgc tgttaccatt ttgagtgcac cgtcaactga    120
aggaacctac gccgtttcca aggacagtgt atcttttgtt atttattttg gttacatctc    180
tatgtcattt atttctcgtt tgaatacatc tcttgaagag gaggcatttc acaagcaagt    240
tgcagactct cagtgggtgt gttcggttga tacaggctct ggcataataa acagtgatcc    300
aactctagac ttcaagattt gtcccaagac aggtggagca atttctgttc tatctgtttc    360
gtggcaaaac aatagccctc aactggttcc tggtcattat ttactgcgaa gtggaacttg    420
gccaattact ggcgttaagc tatctggctt actagttcat agatcaattc gtttggaaac    480
caccagaaaa cttctagaag ctcagaggat ttctgtatcc cagcaagcat cttcttcctc    540
cgctgctggt gctgcaggaa aacaaccaca agtaacgctt acacaattac aagaggagct    600
tgacgaggcc aaaactcgct tagctctcaa agagaaagag ttacttgaag ctctatccga    660
aatatccaaa ttaagattgc aattgtccaa ccaactaagt aatgatgatg tcttcagtgg    720
ctggacagag gaagggccca agtgataaaa gtgcagctgt atctgagcaa ttaattgctc    780
agattacagc tgcagttgaa gcaggcaaca aaaacctgct tcgcaaactg ggcatgggtt    840
catatgggat tctctatggc gcccaagaga agaaagccat ggaactgttt gaccctgagg    900
atgtacataa tataacctca ttgtggtctt catttaagaa aactttcact tcctcgaggg    960
atcatggaaa tctattcttc catttgtatg gagttatgtt tttcatggtt cctcatgtac   1020
atggtgggga aggtagtgta aaaattagtt tatgttccag taatgatcca accaatcctg   1080
ttctgcagga gaaggttttg tatttttccg ggggggcaca ggcagtgtta atgagtccga   1140
ccattacact acctttttgtt aaaagaggcc ccatgttcta ctacacaatg gagtgccttg   1200
gcactcgggc tcaaattcct tgctcagtag tggccatttg gaaacaaaag attgatatcc   1260
gtagtgccat ttactcaaag caggaaacaa tgtcttgggc tattgaggct cttcaccgac   1320
ctcaattttt ccaggataga caggaggcag cacagtacat atcatcagta tattctaatg   1380
ctacctcctc agcaactgat tcagtgcttc cgtttgtggg agcacagctt ggcgacacaa   1440
agatgaatgt gccaagcgaa gcaagaatga tccggtcctc ctcgctccgg gtgcccatgc   1500
tcaaggtgca gagtaagcgg ttttcctcaa tggaaatacc atctacctca actgcacacc   1560
tccttggcac aacgcgtgat gaaactgtaa tacaggagga aagtaggtac gaagaggagg   1620
gtgatgatgg ggttttgttc cccgttaaaa aggctcaagg tctgaactat tcccatgtgt   1680
gggataatct tggtattgag tcctttgtag atgttgagct gcccgaaaac tgggatgagc   1740
tgtcggtgag acagcaagtt gctgcagcaa tgatagcatt tgcaaacaag ggtgtttgct   1800
tggtcccaaa acatataatc aaccgggaca agcacaatat ccacttggag aatatcaccg   1860
agcacaacta cttggtgata ctggaaaggt acggcattgt gaatgccggc tctctggcca   1920
gaactgaaaa ctggtacaat cttaccttgg cacagagagt ggaagagcta atttatcaaa   1980
gggacgatgc atatttcatg tttggtgata acaccaaccc atatcctccc tttgattgtt   2040
atgatggctt aacgctcaaa gttcgcagtg agctagagcg tgtggcaaag gagcaggcgc   2100
gccaaagatt ttacaaggag gcggccaggg ctcaggtgaa aaacaaggtg gcccaaacta   2160
gtgtggaaga aataccatcc acctcattcg ccacaaaggt tgccatggag agtggcagtg   2220
tggatagcat gaaaattgct attcaagctg aagctgccaa tgaagctgta aggcccaatg   2280
aagttatgtt tgaatttggg caagaaatga ataatgaagg tgcgacagag ctggaattac   2340
aacaaccagc ctgcgtggcc agtaactcct tcttcaatgt tggagttttt gagtttgcat   2400
ggaagaaaag cagttctgtt gctgctgagg tgctatcact ggcgctccct gcggctctct   2460
```

-continued ttggtaaatc caaggagatg tcaatgggat cgcaaatgct aaggtattat gatgccgcat 2520
taattatgta caaggtcatc ttgtatattt ccggcatggg tgcaatttcg ggtcagctgg 2580
ccctggtttg ggatgagtgc aatgtgctca acagaaagaa ggagttcatc aacattgcct 2640
ctctgtatgc cagcaaacat aggctggttt cagcatctga acagagtagt ggggaatttt 2700
gttttacacc tacgggtatc ggcaaattcg ttccacttga tccagcctcg ggggcttatg 2760
atctgggtag catacgggtg tttgtgacgc accccttggc tagtgctact gaattggaga 2820
gcataccttg tcacatccat ctgcagtgta aagtgttgtc gaccaacatc atgcagcctc 2880
ctcgtttgcg agcacaggca caatttggta tgaaaccaga ccagacacac tttccacgat 2940
ttccaacaaa tcaggtactg ttacactaca attggggagt ggctgctagc atgggtacta 3000
ccttagttag catcttctct ccgtcaggca tatatgaaag tgacggtacg ctgcaaccat 3060
ccttgcttgg aaacatagca cgcaattgca aatggtggac tggcacttgc gtgtttgaga 3120
tttgtattga gaagactcag ttccattctg gtagtttggc cattggactg ggtacactga 3180
acacaagcat gtccacccct catgacattt taaatatgcc gcatgttatt tgtaaccttg 3240
agatgggacg aaagttctat ttcaggtgta cgataaccaa ttggaatggg aaaaatcttt 3300
tgaccactgg tcggaagagt tctctaccgc ggcccaagca tatgtctcac atgaggttgt 3360
ttgctacagt cttgaaaccc ctggtatcaa cttcaataca tctagatacg gtcggggtaa 3420
cagtgcagct taaatgcata gaagatttgg tccttggggg cactgtgtct gttaaaccca 3480
tttacggaca ctggactaaa ggaaagaatg ctgtggactt cctattctct gagatggact 3540
tgtctcagcg caaagaaatt gagaaattac gcaaggaaaa cgttgagaca tttgatgaga 3600
aaggaaagaa gcagccacag gtacaagtgc cgctcagaga caagttttca tatggggctg 3660
tacaatattt tgtgatgaat tggaaggacg aagagcgact gttggtttta ccatgcgcac 3720
cctggtccgt aagattccct caggggcac tggtacagga ggccatcaca tgcccattca 3780
ttgattggtg ctcttccttc tgttattggt ctggaagtct tgaatacacc attattgtac 3840
atagagtgca gacttccaat aacataggag gagtgctgaa catcacctta gattcatcag 3900
ggtacccttt tcctcttgga atctcaaagg gcacctatgt tgtctctgct ggtggaggag 3960
caaaatgggc tttcacttat ggtatgagcg acaacatctt ttcttttgtg gtgcatgatg 4020
atgagttttt tcctagacgc cataccaaag ccagagcaat agatccaaat gcttcaagaa 4080
taatgactct gcaagatcga ctaggaaatc tcataataaa tttaccagcc aaagatgtga 4140
taagctctct ggaaatcttg gtcaagccag gacctgattt caaattgcaa ctggctcaag 4200
ctccttcagc aaatcatgag aagcatttgg gtgatatgca aacgcatacc tacctttata 4260
ctcctgattt ttcagaacta aggagttttg aaaattaact atcctgtacg tgatatagga 4320
gccgtgagtc cggcatgtga ctcatcatgt gcagttaaca tgtgtactgt gaataatgtt 4380
aactgtaagg atagttaatt ttaacggaga gtactgactt taactagttg ggagtccggc 4440
tccatttgga gtaccaatga atctacattg gttaaagaga tttgcacgcc tctctttaaa 4500
tatggatcgt gtaccctgct tggttagaaa gtacctttac ttaggtttac aaagtacggg 4560
gagcactccc tggttaacat agtgcaggtg ctatcccatg atagtccttt aactcaaggg 4620
ttgagttcgg tttgcatctt ttgccgtgat gaaagatgag gtagcttccc ccttattggg 4680
aggctgaaac tacacatatg tagtgggttt gactgagtcc tataatcagt ccgtttgaaa 4740
ttcgataatt ttccgtagct tgcgtcaagc tgctcacgtt aggggcgtga gtgaagatgc 4800

```
gccgtaccac gccttccccg gcaatgccag tggttcagag cgggccctca gaatagaggt   4860

taaaactagt gtgatggtgt atatcacgat aaaaagtgac acccgggttg tgctgcgcct   4920

agttaacacg agcacaggtc ccaccctata gtggaagaaa cttggttgag ttttaaagaa   4980

caacccgttt gagcgacgac aaagttccgt agcttgcgac aagctgtttg tgttaggggc   5040

acaaatgaag ttatagcaca ccacttcttc cctaggttcg tccagtggtt tcacagtgct   5100

atcctcagaa aagaggttaa atctagtgtg atggtgtata tcacgataaa gaatgacacc   5160

cgggatgtgc ttctcctagt taactcgagc acggttttca caccacagtg aaactatctt   5220

actgctttaa atgttgtttg tttgttttac ttgttttatt gagtgtttaa tatcatgcat   5280

atttgctgtt gaaggttctg tcgatgaggt caaatggata ctcgggaact acagtaactt   5340

tgcatttgaa ttgttttcaa ttcagtgtgt gagtttgaat atgtatttta aaaaaaaaaa   5400

aaaa                                                                5404
```

```
<210> SEQ ID NO 2
<211> LENGTH: 7809
<212> TYPE: DNA
<213> ORGANISM: Artificial Sequence
<220> FEATURE:
<223> OTHER INFORMATION: DNA equivalent of the ToTV-E01 RNA 1 genome

<400> SEQUENCE: 2

ttaaaagagt tattttgaga atataaccta cgtcgttatt cacagaccaa gtctctgtta     60

atcaaaatct ccctttaaaa ctcattctac ttttacattt ggcaacatgt ctttttccaa    120

gatgttcccc ggtttcaact cagttactga aaagtgcgct accagctcct ctggttcttt    180

cttttcagag cttactgcta gtattagtaa tttctcccgc actctgtcca atgttaccaa    240

ggtttcatct caaatttctt ctcacattga agatttgaag ccttcagtta cagatgctgc    300

ttcttccttt accagcacct gtaactctgt tactaaattg ttagataaga taatgacttt    360

aattgaaccc ttcatcaagg cttactcttt tgtcgcatcc atgtacaaat caatttgtga    420

tatggttgca aagattgttg caagcatcaa agataagttc acacttggtt ttaactgggt    480

gttggacaaa tctgaggatg tggatgtttt agttatagct tttcttattt ttgcaatttc    540

tatgttaata attgttttca tttgtccaag tagtgtacta gatggagttg tacagatgac    600

tcacatagtt tttaatacag taggtaactt cttttcagct ttgtacaaat tagactggtt    660

accgacatgg tcccaaaagt tttcaatgat ggcacaagcc aatgttctac caggggaatc    720

catgtcacac tcaccacttt cacaagtggt agcatccctc atagcctttg ggatttctac    780

ccttgtgttc gtggctgtac ctggtagacc caatggtcta tccaacccgc tatcaaaaat    840

tctgtactca gcgggaagtg gtgctcaaca gtgcaatcaa ttgtttaccc tgttcaggaa    900

tatgaaagat tgtacttccc aggccttttc ctgggttctg gaaataatag tagacatttt    960

tggttttaag aatccagttt tgtctgctat tagtgccaca ttgtctacgg acttattcac   1020

gtggatggaa gaggtggatg cagtgtgtga tccagcacat cgcttggaaa attttgcaaa   1080

ccctgcattc actatcaagc tccaacatct aagggagcag gctcttaaaa tctctgctta   1140

cattgctaca catcctgtag cagcctttat gagccacagg gtaacggcag caatarccca   1200

tcttgataag atatatgggg agaactgcca gcacactggc gtgggccaat acagggcaga   1260

accttttatg gttcaatggt atggtgccag tggttgtggg aaatccacca gcatgcggct   1320

gttcatcaat gatgttttgg accgcatgga agagccaaag ttgaacaggc tctatgctgt   1380

gagtaagcga gatgcttact ggtcaaatta tgcccatcaa actgctatcc tgatggatga   1440
```

-continued

```
catgggcgct ctgagagatg gggcagggca atgccaggac attaaggatt tgatagatat   1500
caagtccact caaccagccc ccttgcccat ggcagcagtg gaggataaag gccgccactt   1560
tacctcccga tatatatttg ccacatccaa ccttatctca gctcctgctc agtgtggtct   1620
aacctacccc gatgcttttg agagaagacg ggatgttctt gtggagtgca ggaaggtggg   1680
tgagtttaac actgatgctc ccacttctca ccttgaattt gatgtggttg agagcaaaag   1740
accccatgca ataacacaca ggggtttgag ctatgatgat ttgctggaat atgtggttgc   1800
caagtgcaag gttcatgcag aaatctcagg aaaactgtat ggcgccacat caggcaaggt   1860
ggcacaggtt gatgtgtcac ctgaggaaat aatagcatcc atggatatgt tgaatatcca   1920
agataccaag caggatgcta agcttcccgt ggttgttgta agtgaagagg atagggtggc   1980
ctactcycag gagttgacag tggaagcttt gaaatatgct tatcagggta gtctgaatcc   2040
cgcagcatat ttccctcatg acatgcacaa acaggccata tttgatgtgc taagtgaatc   2100
cgccaaagaa acattcacca ggtgggttaa tgacatgctg tatcaaggtt gctgtaatga   2160
gaactatcgc tggctgataa agaatatccc agctgattat atcatgcact ttaagagctt   2220
catctacgct tccacaatca atgagcgtag ctttgacgtt cagaagcagc tgcctgatgg   2280
aatggcgcac cgtgccatag atgctgatgt ggacacactg atatgcgtgg agcagatgcc   2340
tgcccacgta caattcttgt acacagcatt tgtgaggtat tggtgccgca gaaagatgga   2400
acagcctagg caatcctggg tggtagtttg ctaccacagt attgtggatt atatcaagaa   2460
tgcttggtat gatttaccgt acatcttgag agttctgatt aaggctggcc ttattttaat   2520
tgcactcaat ggtgcatttg ggctgtcac agcattctgt gcttgttggc aatccaacac   2580
tttcccttca gcagaaggaa gaggagggat taccaacgag tcaaatagca tctccagccg   2640
gaagaacaag ggaaagagca tctttgctcg atctttgctg gcacaagcca agggtgatat   2700
gctggagaaa tgggcaagtg atgatggctt catcaatgaa ggattgaaga aaaacctagt   2760
cgtcttgaga ctaggtgaag gtgtctactt cagaggcacc tatgtctgct cgggctgggt   2820
gatgacagtg gctcatgctt tttcaagcct ccgtgatggc acaactttct caataataca   2880
tgcccagtca atttccaagg tgcaatacaa tgccaaaact gcacggttct tgaaggagca   2940
agatattgtc ctgctcaatg ttggaaaccc cgatggtccc aagcctgata ttcgcaaaca   3000
ctttcctgta cgggatggtg tttgtttttc taagggcact caaggggtat gtgtgagagc   3060
agtagcatca aaggatgctt cgcaaggaaa tcttgagtac ttgcgtttta atgtgatgat   3120
gtccaagggt taccttgaaa aggtaacgta ccagatggac tctagttcct ttaaactgga   3180
gtctcaagca tcttatgagt atcacatgaa tggtgaaaat ggtgattgtg gtactcttct   3240
tcttttgccc aacgtgcaag acaaacaacc atgcattgtg ggtattcatt gtgcttctta   3300
tgatgaagaa gctgcgcaca aagggtttgt agcatccaat gctacagcta ttttccgaga   3360
tcagttggaa gatcttccga ctggtccggt taaagtagca atggtaaggt gccagctcct   3420
taaggatcta cgagccaggg atgcggctct ttttgaagaa aaacaggtgg cttttgttgg   3480
cacattgcca gctgaacaag cagccacggt tccccacaaa acaacgctgc gaaggagtgg   3540
cttgtttgaa gcttttgggc ctgcagaaac tgctccatct atcatttcag cttcagacaa   3600
acgtggggaa ggttttgatc cgtacgtggc tggcatacaa aaatacaatg aaacagcaca   3660
aaattttgat gaggacattg cgaggctagc ctatgaaggg ctacgtcaag caattttgcc   3720
tgtgctgcac tcccagcgag ttccttttgg aaagcccgtc acacagaatg aagatgtggt   3780
```

-continued

```
gctcaatggt gttgatgggt ttgactattt tgacgggatg gagttgagta cctcttgcgg   3840
gtatccgtac aacaagttgg gtatgggcac tagcaagaga gagtttgtgg agccaagtgg   3900
agatggagat cgagtccaac tcaaaaggac cactccaatt tttgatgact gggaggcttt   3960
ggatgtggaa attcgcaaag gaaactttgt ggaactggtc accacccaat gtgccaaaga   4020
tgagcgcttg ccgttggaaa aggtttttgg gaagcggaaa acccgtttgt ttgaaattct   4080
tcccttccat tacaatatgt tggttaggaa gtatttcctg gatttttccg ccagtctgat   4140
ggcatcccac aatgctctgc catgcaaagt gggcattaat cctggaggta ttgaatggac   4200
tctgttggct aatggcttca gagcagtctc tgatacagga ttttctgctg actattccag   4260
ttttgatggg agagctccca tctttgcctt tcaatggttt tgtgatcttg tggatgacta   4320
ctatggatca cctcctggtt ctccagactc caatgccaga catgtgcttc ttatgatggc   4380
ttcatgccat tatactattt gtgagaacaa ggtttttagg ttggtgggag gtatgccttc   4440
aggatttgca ctcaccgtta tcttcaactc tcttctcaat gagttttata tgcgttatgc   4500
atttatttct ctattgagaa gaccacatat agcagctcaa gctatagggt gcaaaccctc   4560
tgatttcaac aagctatttg tggcagtcta tggtgatgac aatctagttg cagttcccat   4620
ggaattgcat tggtatactc tgccagctat tgcccaagaa ttggagatgg tgaatgttat   4680
tataaagaat ggcatcgaca agaacatgga tgttagcagt tccaaaatgc tagacttgtc   4740
tgagctaaca tttctaagca gaggttttaa gaggcaccgt ctaggatacg ttcaagctcc   4800
tctgaaatgg gtatctatca tagaaccaat gtactggata aggccttctg ttggttgtcc   4860
cgatgctctc gctatgttgg aaaacataga cacgggagtt agagaggcat ttcaccatgg   4920
gcctcaggtt tttgaaaagt tggtgacaga tgttcaaaac gctctcaagg agcggtgttt   4980
cccagccacc acatttccta catattttga attggagcag gactggctgg tggaggttac   5040
aggaaatcca gccattgggc tcatcaagga acttcatatt gcagcttcag cttttgtgcc   5100
tttgcccccca ggcaatactg ttctgaattt ttctgatgga gtgcatactt ttgctgaccg   5160
agtgagtttc tgctcctcgc gaacagctgc tgcacagcag tgggacacca ccactgtttt   5220
ggtgaactgc actggggcaa agagacccac atgggtaaga gggcccacca catggaggga   5280
ctttgaaggg cttatttggc cttacacaat ggctgcaatc aaggaccaca tctgcagcat   5340
tgtaaccaaa ggggtgacca aaccacatgt ggtttttgtt tgtggcaatg ggtatgctat   5400
tggtccagtg tgcgctgcat tgtactgtct gtccactggc caatattctt ctcaggatgt   5460
tgttgtgaga ttgagaacca tagcagatgt tacagatctc agtcaatatc caggaggttg   5520
tgccaagtat cttctgaaat gtgctgatac aagagaagaa gagcttgcag atacatgtaa   5580
aattgcacaa gccaagggtg agacaccagc atacatacct caaggaggat tttcccttgg   5640
taattttaga attgtgcaag ggagaattga tctacagttg gcccagcgct tgccttttac   5700
agtgggacct tatgggggat ggggtcaaca cactactaga gagcttaagt tgctgctcaa   5760
ggacatggag aagatatatc aaattttagt ccaaagagag agcttcatca ctctctactt   5820
tgactatctc agttcagagc aggtgatgtt gttggttgac tttcttaggc tccaagggtt   5880
ttttccycgc caaaatgatg tggattactt gcttaaagcc tttaagctga gcaagcagag   5940
gcacaataag gaaaactgtc atacggttta ctttagaaag ccttttctct caaggaaaat   6000
gaccatgggg tccaaagaaa ttctgtccgc aacagctgct gagtcattgt ttggtatgga   6060
tgtttccgct aatgtgctca agagtaggct acttcatctt cagaagccca taaagtgttc   6120
atccatggag ttggccttta aaatttattg tgtcatccag ggccacctga gcaaggaagt   6180
```

-continued

```
tgtaactcac ttccaacgca tgtaccaaca agatctgaca gaagggatca tagagaaagt   6240

gatattgtgg ttaaccgcca cactgtcgga gagctttcca gtggatcttg ttgatgtacc   6300

tttaggcttg gataacatag agatccagga taaaggtttt tccctaaatc caaataaatat   6360

aaatatgaat gcatgtgatg ccatcttgtt tcaactcact gagtgttaca accgatcaac   6420

aaagaaacat gtgttctgtc gctacacgac tgcatcctct cttgttgttg cctatgtgct   6480

tgcacataga catcagacaa ttgatgagtt gccgtccttc tatgcaacac acccagatgt   6540

gttgcttttg acaccaatcc taacaggcta caaagcgcct tgagtcgggc taaatgactc   6600

agcttgtaca tgcaatatgt gtactgtgaa taatattgca tgaggattaa cggagagtac   6660

tgacttttgc tagtcgggag tccgacccac tatatgggta cctgtgaatc tacacgggtt   6720

aggagatttg cacgcctctc cataaatatg gttcgtgtgc cctgccttgg ttagacagcc   6780

ttccatgccg gaagtaaatg gcctataacg gagagtactg actttaacta gttgggagtc   6840

cggctccatt tggagtacca atgaatttac attggttaaa gagatttgca cgcctctctt   6900

taaatatgga tcgtgtaccc tgcttggtta gaaagttcct ttacttaggt ttacaaagta   6960

cggggagcac tccctggtta acatagtgca ggtgctatcc catgatagtc ctttaactca   7020

agggttgagt tcggtttgca tcttttgccg tgatgaaaga tgaggtagct tccccccttat   7080

tgggaggctg aaactacaca tatgtagtgg gtttgactga gtcctataat cagtccgttt   7140

gaaattcgat aattttccgt agcttgcgtc aagctgctca cgttaggggt gtgagtgaag   7200

atgcgccgta ccacgtcttc cccggcaatg ccagtggttc agagcgggcc ctcagaatag   7260

aggttaaaac tagtgtgatg gtgtatatca cgataaaagt gacacccggg ttgtgctgcg   7320

cctagttaac acgagcacag gtcccaccct atagtggaag aaacttggtt gagttttaaa   7380

agaacaaccc gtttgagcga cgacaaagtt ccgtagcttg cgacgagctg tttgtgttag   7440

gggcacaaat gaagttatag cacaccactt cttccctagg ttcgtccaga tggtttcaca   7500

gtgctatcct cagaaaagag gttaaatcta gtgtgatggt gtatatcacg ataaagaatg   7560

acacccgggg tgtgcttctc ctagttaact cgagcacggt tttcacacca cagtgaaact   7620

atcttattgc tttaaatgtt gtttgtttgt tttacttgtt ttattgtgtg tttaatatca   7680

tgcatatttg ctgttgaagg ttctgtcgat gaggtcaaat ggatactcgg gaactacagt   7740

aactttgcat ttgaattgtt ttcaattcag tgtgtgagtt tgaatatgta ttttaaaaaa   7800

aaaaaaaaa                                                           7809
```

```
<210> SEQ ID NO 3
<211> LENGTH: 17
<212> TYPE: DNA
<213> ORGANISM: Artificial Sequence
<220> FEATURE:
<223> OTHER INFORMATION: RT-PCR Primer

<400> SEQUENCE: 3

gagagccggc attcaca                                                    17


<210> SEQ ID NO 4
<211> LENGTH: 17
<212> TYPE: DNA
<213> ORGANISM: Artificial Sequence
<220> FEATURE:
<223> OTHER INFORMATION: RT-PCR Primer

<400> SEQUENCE: 4
```

-continued gcacagcttg gcgacac 17

<210> SEQ ID NO 5
<211> LENGTH: 24
<212> TYPE: DNA
<213> ORGANISM: Artificial Sequence
<220> FEATURE:
<223> OTHER INFORMATION: RT-PCR Primer

<400> SEQUENCE: 5
cccatcatca ccctcctctt cgta 24

<210> SEQ ID NO 6
<211> LENGTH: 22
<212> TYPE: DNA
<213> ORGANISM: Artificial Sequence
<220> FEATURE:
<223> OTHER INFORMATION: RT-PCR Primer

<400> SEQUENCE: 6
ttccagtaat gatccaacca at 22

<210> SEQ ID NO 7
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 7
caagccatca cggaacctac 20

<210> SEQ ID NO 8
<211> LENGTH: 19
<212> TYPE: DNA
<213> ORGANISM: Artificial Sequence
<220> FEATURE:
<223> OTHER INFORMATION: RT-PCR Primer

<400> SEQUENCE: 8
agcatcttct tcctccgct 19

<210> SEQ ID NO 9
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 9
tgctgaggtg ctatcactgg 20

<210> SEQ ID NO 10
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 10
cacactttcc acgatttcca 20

<210> SEQ ID NO 11
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 11
aaaggaaaga agcagccaca 20

<210> SEQ ID NO 12
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 12
ggaaatcttg gtcaagccag 20

<210> SEQ ID NO 13
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 13
gcaatgccag tggttcagag 20

<210> SEQ ID NO 14
<211> LENGTH: 20
<212> TYPE: DNA
<213> ORGANISM: Artificial Sequence
<220> FEATURE:
<223> OTHER INFORMATION: RT-PCR Primer

<400> SEQUENCE: 14
ggtcaaatgg atactcggga 20

<210> SEQ ID NO 15
<211> LENGTH: 7229
<212> TYPE: DNA
<213> ORGANISM: Artificial Sequence
<220> FEATURE:
<223> OTHER INFORMATION: DNA equivalent of the PRI-TMarV0601 RNA 1
genome

<400> SEQUENCE: 15
aaagaattat atatcaagat tgcaacctac gtcgttgttc acagactacg cctctgttaa 60
ttgatatttg attcttgtaa acttttccaa catcttcttc tcttcttact cgaccattat 120
ttaaactcct caattttcca atggcttttt caaagatgtt ctccaaggtt gctggtgttg 180
atgacgccag ttcttcttcc accacttcat tctttggtga actttcaaat tctatttcca 240
aattttcaaa agcggttagt aatattacca ctatgtcaca gaagatttca gatcatcttg 300
aggatctgaa accatctgtg actgatgtgt ccacatcttt tgtggccact tgtagttcac 360
ttaataaagt tttggacaaa attggtgcac ttatagatcc atttcttaaa gcgtactctt 420
tcttgtccac aatgtacaaa tctatcaagg atatggtttt aaaattgttt gagagtttgt 480
ccaataaagt taaattagga tttgcttggg tgttaaataa aagtgaagat gtagatatag 540
ttgtatatgg ttttcttgta tttgctataa cattgttagt gcttctattt gtttgtccta 600
gtgatattgt tgagggtgtt tctaacactg tcaaaaatat ctttttgata gtcggaaaca 660
tgttttcaag tctatacaat ttagattggt ttccaaaatg ggccgaacga ttcaccatgg 720
tggcccaagc tagtatgctt cctggggaat cagtttcaca tacaccaacg tctcagttga 780

-continued

```
tgtccacaat attggctttt gggatttcga cgttggtgtt cattgcagtg cctggtagac    840
caaatggctt gagcaaccca ttgtccaaaa ttctctattc gacaggaagt ggtgctcagc    900
agtgcaatca actattcact ctttaccgta atatgaaaga ttgcacctcc caggctttct    960
catgggttct tgaaataata gtcggcacct ttggattcaa aaatcctgtg ttgtcagcta   1020
taagtgcaac gctgtccact gatctgttcg agtggatgca ggaggttgat gcagtgtgtg   1080
atcctgcaac gcgccttgag aactttgcca ataaggcttt ccctaccaaa ttgaaccatc   1140
tgagggaaga agctctcaag atctcagctt acattgcaac ccatccagtt gcggccttca   1200
tgagccacag ggttagtgct gccattgcgc agttagaaaa agtttatgct gaaagttgta   1260
ggcacatggg cgtgggccag tatcgtattg aacctttat ggtacaatgg ttcgggtcca   1320
gtgggtgtgg taaatctaca tccatgcgct tatttattaa tgatgtgttg gacagaatgg   1380
gtgagccaaa actcaatcgg ctatatgcag taagtaagag ggatgcatat tggtccaact   1440
atgctcacca aactgctatc ctgatggatg acatgggagc attgcgagat ggggctgggc   1500
agtgccaaga tattaaagat ctgattgata tcaaatcaac acaaccagca cccttaccaa   1560
tggccgcagt tgaggacaaa ggcaggcatt tcacctccaa gtatatattt gccacatcca   1620
atctgatctc agctcctgcc caatgtggtc ttacatatcc agatgctttt gagcggagaa   1680
gggacatcct ggtggagtgt atgaaggagg gcgagttttc cactgaagat cctacgggac   1740
atctcagatt taacatagtg gagagcagaa gacctcatgc tatcactcac aggaatttga   1800
cctatagtga tcttttggag tatgtggtag ccaaatgtca ggtacatgca gaagtatcaa   1860
agcaattgtt tgaagctgaa tctggcataa gtcctaagat agctcaggtt caagtttctg   1920
cagatgatgt gatagcgtct gtggatgggg ctagattgcg caccaagcaa gatgaaccaa   1980
tattggtgcc cactgttgtg agtgaaaatg atagagtgat ctatgcaaga gagctcacgg   2040
tagaggcatt gaaatatgca taccagggca gtttggaccc tgaggaactt tttcctcatg   2100
accatcataa gcaggccatg tatgattctc ttgatgatga acataaagag attttcaaca   2160
aatggagagt caacatgttg tatagaggag cagatgctga acagtatcga tggttggtac   2220
aaaacattcc tgatgactat ataatgcact ttaagagttt catttatgca tcaaccatct   2280
ctgagaagaa actagcagtg cagacagaga tgaggactgg atttgcacat tcttgcattg   2340
atgcagatgt tgacaccctc atatgtatcg agcagatgcc accctttgtt cagtttttat   2400
atacagcatt tgtgagatac tggtgcaaca aagtatcaaa agagccaaag gaatcatgga   2460
tcaaaatttg ctaccataaa atcgttgaat atatcaagga tacatggtgg agccttccct   2520
atgcactgag attgctcatc aaagcaggtc tgattataat ggctcttaat ggagtttttg   2580
gaggcattac agcattttg gcgtgctggc agagtaactc tttccccaat gcatcgggca   2640
gaggaggtgt gaccaatgaa tccaacagta tatccagtaa gaagaacaag ggtaataagc   2700
tcagaaatct tctcgttggt caaagttctc aatcattggc acaagattgg gctgctgaag   2760
atggatttgt aaatcagagc ctcaagaaaa atttggtggt gttaagactt ggtgaaggag   2820
tgtactttag aggcacctac gtgtgttctg gttggataat gaccgtagct catgcattcc   2880
acaatgctcg agatggtact ccatttacaa tcatccatgc caattctcga tctaaagttc   2940
aatacaacgc cagagaatca aggattattg agggccaaga catcattctg ttgcgcgttg   3000
gtgatccaga tggtccaaag cctgacatcc gtaaacactt cccaagaagg gatgaggtgt   3060
gcttcacaaa gggctcacaa ggattgtgct gtagagctgt tgcgtctaca gatccacgtc   3120
```

-continued

```
ttggcaattt agagtttctc aagatgccag tgatgatgtc aaagggatac acagttaaag   3180
tggaatatga actgaactcc tccagtttta agatttgctc tcaacaatct tatgaatacc   3240
acataaatgg ggaaaatggt gactgtggca cgttgctact gttaccaagt gttcagaata   3300
agcaacctgt gatcgttggc atccactgtg catcatatga tggcgtagca gctgaacgtg   3360
gatttatctc ttcaaatgct acagctatct acagggaaca actagaggat ttgccaactg   3420
ggccggtcaa agcagcaatg gtacgctgtg atattctgaa gtcaattaga agcagagaaa   3480
cacagctttt tgaggaaaac caagtgtact accttggaac agttccacag gagttggccg   3540
ccacagttcc ccacaagacc actctgcgga aaagccaatt gtttgaagca ttcggacctg   3600
cagagacagc accatccatt ctaacagttc atgacaaaag aggtgatggt tttgacccct   3660
atgtggctgg ggtaatgaaa tacaatgaaa cagcttgtgg atttgatgat gacattgcca   3720
aactagcatt cgaaaatctc aagtgctcgc tgctacctat catgcgtagc cagaagatcc   3780
ctgggggacg tccatgtgaa agggatgagg atgtagtgct caatggaata gatggatgtg   3840
attactatga tggcatggag ctgagcacat cttgcggata tcccttcaac aagatgggga   3900
tggggatgaa caagagagaa tttgtgcaat ccactggcga aggagagaga gtggaactca   3960
aaagagacac tcctgtattt gaagcatggg aagagctaga tgtgcagatt aggaaaggca   4020
tccatgtgga tctggtcacc acccaatgcg ccaaagatga acgcctccca cttgagaaaa   4080
tctatggcaa gagaaagacc aggctctttg agatacttcc tttccattac aacatgttgg   4140
tcaggaagta ttttcttgat ttctcagcca cattgatggc tttgcacaat gctataccat   4200
gcaaagttgg tattgatcct acaagttctg agtggacatt gttggcaaat gggtttagag   4260
ctgtgtcaga cgtgggattt tcagctgatt attccagctt tgatggaaga gcacctgttt   4320
ttgcttttca gtggttttgt gatttggtgg atgaatacta cggatcaaag cctggcagtc   4380
ctgattccaa tgctcgacat gcacttttaa tgatggcatc ttgtcattac acactgtgcg   4440
aggataaagt gtttaggttg gttgggggca tgccatcagg atttgcacta acggtcatct   4500
tcaattctct cctcaatgag ttttatatgc gatatgcctt tatatcattg ttaagaagac   4560
cccatattgc tgccagggct ataggagtta aaccaagtga tttcaatcag ctattcatag   4620
ctgtttatgg agatgacaat cttgttgctg taccattaca tctccagtgg tattctctgc   4680
caaatatagc acatgagtta gaactggtca atgtaatcat taagaatggt cttgacaaat   4740
cgatggatgt taatgaggta caatttcaag atttgtctga gctaactttt ctgagtagag   4800
gttttaaacg acatgctctt ggataccaca tggctcctct caagtgggtt tcaatcattg   4860
agcccatgta ttggataaga cctgccccag gttgtcctga cactcaggcc atgatggaaa   4920
atgtggaaac aggaatacgt gaagctttcc atcacggtcg tgtggcttat gacaagcttg   4980
tcttagatgt tcagacggcg ttggatgaaa ggggtttcag agctgtgatc tttccttcct   5040
atttggaagt ggaacaggaa tggattgcaa aggtaacagg ggattcaagt gccctgacaa   5100
tttgtgaaat ggcaaaagca gctatttcct atacgccatt ggacgcaggt gagaagatca   5160
caaattttga gcgtgatctg aattggtttg caccaaacat tggtttttgt tcagcacgta   5220
ctgcagccca ctacacgtgg gatgaagggt acattattgt caactgtaca ggtgcaaaga   5280
agtccaattg ggttagaggt ccagccaact ggaaggactt tgaagggaaa atgtggccgt   5340
acactatgtc agctataatg gatgcccaaa agaatgtgtt ggcaggagga catgtagcaa   5400
ccaatgtcgt tttgtgtgt ggaaatggat atgctgtcgg cccaatttgt gcagcgctga   5460
tggccttagc aacaaggcaa tattgtgtgg aggacataat agttagattg cgcacaattg   5520
```

gaaatgtgct tgacctcaat acctatcctg gaggctgtgt gcagtatttt cttcaatgtg 5580
tgcctcatgg agacaaagtg gctcaaagtg gtgcatcgct ccacagtagt tttatgcacc 5640
aagggtttga attgggcaac ctccgcatta tacatggtga tttagcaaaa cagacagcaa 5700
tgcggatgcc atatgtggta ggaccacatg gaggatgggg aaatttttcc acacaggatc 5760
ttgagagttt gctacactat ttggagcagg gatatgcaga gttaattcaa aagaatacaa 5820
aactaactct gtatttcaaa gagctgagta tggaaaatgt gcaacaactg atagattttg 5880
ttaagcttca ggggtttttc ccaaaagaaa ctaccattca gaagctcaaa aattttgttg 5940
atgctgaatg tctaacattc aaagcaagga gctttaggca cgtagttttc aaaaagaaac 6000
ttttgagttc cacatggaaa atgtgtggtg aaagtattgt tgcttcaagg tctgcagaga 6060
gtctattccc tggcaatttg tctgcttccg tattgaaaac attattggaa agacacacaa 6120
gaagcatgag ttgtcagagt atggagcttg ctctgaaaat atatctatta aacttccaag 6180
taataacaag tgagatatta aagaagtttg aagatatatt tcaggagaag atatccacca 6240
ccctactaat caaagtattc ttgtggcttg aggagagtta tcagactgag atctgtatag 6300
attctcaggt gctccagagg ataaactccc agaaattcag agtgcaggaa ggtggttttt 6360
atttgcatcc tgaaggaatc aacatgaatg ccgtagatgc aataatattt tctctgtggg 6420
agtcctatag ccgagatagt aactcctatt ctgtgtcaac tcccatcaaa ctggggtgtt 6480 tcatttcct tgtcgtgcta gatagtcaag gcaaggaaga tcatcctgtt cggaggtttt 6540
caacggtttt ccttaaaaac tgtgaaacca ttcttacaaa ttacaaggag ccttgagtca 6600
ggcattatga ctcaatttgt gcgatatgca tgtgtactgt tagtaatgta tatcgttagg 6660
atggttttgt taagggagag tactgtcttt taatagatgg gagtcccctc cactttatgg 6720
agaccaatga atctacattg gtatagaggt ttgcacgctc ctctttaaat aagtttcgtg 6780
tgccctgctt ggttagaaag catgtggtga ttaacactac tcgtttggag tataagcaat 6840
agacctcatg atgtctaact catgcgtgat tgctcatgta cgaaataaat gagccgtttg 6900
gaactcgata atttccctta gctgctgcac agctgtcact attaggggta gtggcgaagt 6960
cgtgagtccc ctcttcctcc ctaggttcgt ccagagggtt caaagattca ccttctttgt 7020
caagaagcaa tgaatgacac gtgttgcgtc gacaaagcac cgttctacgt ggttagtaga 7080
aagttatatt atattagatt tgttagtcaa ttgtgtgatt tctttcttag attaggaagt 7140
tttccgtggc gataggaagg gtttgtcctt ttaccttctt tgctatgctg gacacaaaaa 7200
gattttcttt tcttttattt taaaaaaaa 7229

<210> SEQ ID NO 16
<211> LENGTH: 4906
<212> TYPE: DNA
<213> ORGANISM: Artificial Sequence
<220> FEATURE:
<223> OTHER INFORMATION: DNA equivalent of the PRI-TMarV0601 RNA 2 genome

<400> SEQUENCE: 16
aaagaatttt aatatatatc tgtcatgcaa cctacgtcgt tgtgcgatct acgtcatcgc 60
tcgcagatat aaaattaaat ccttttagct tgagaactac gtcttctcat tttcttttcc 120
tttgttttgt tgttctttat gtcattcatt gggcgtttga atacatctgt agacgaacaa 180
gcttttcatc atcaagttgc cacctcgaat tggatttgtt ctgttgatgt tggcaccggt 240
ttgataaata gcaatcctac ccttgacttc aaagttgttc ctccatcagg tggtgctgtc 300

-continued

```
tcagttttaa ccgtttcttg ggagaattca acgccacaat tagtgcctgg acactatttg    360
ttgcgtagtg gtaattggcc cattaagaac gtaaagcttt ctggtttact tgtccatcgt    420
tcagtgcgtc ttgaaacaac cagaaaggtc ctagaggaaa acaaggtttc tatttcagca    480
tcatcttcat cttctccttc ttcttctgac agtaaaggca agagtaaagt agagcaaccc    540
acacgagagg atctcattaa agaagttgag gttctcaaac gtgagttaga gagatttcag    600
aaagagttgg caagtcaaaa atctgaaaat cagaaactac aacttcaact ctccaatcaa    660
gttagtaata atgacatctt ctcaggttgg actgaaagtg ggccccagta atcaccagca    720
ggaggaagcc tccgagaggt tgatatcaca aataacagct gctgtggagg ccggaaacaa    780
aaatttgctc agaaagcttg gcatgggttc ctacggggtt ctttatggtt cccaagagaa    840
gagagcaatg gagttrtttg acccagatga tgtatcaaag atcacatccc tttggtcaac    900
attcaaacat aagtttgttg agtctaagga ccatgcaaac ttgttttttc atctgtatgg    960
tgttcttttc ttcatggtcc cacatgttca tagtggggag ggaagggtta agataagtct   1020
ttgttcaagt aatgatcccc tctcaccggt aatacaagaa aagacactgt ccttggccga   1080
tggagcgcag gcagttctca tgagccccag cataacattg ccctttctca aaagagggcc   1140
catgttttac tacaccctgg agtgccaaaa taccagggca cagattccgt gttccgtggt   1200
tgccatatgg aaacaaaaga ttgacacaag gagtgcagtt tattcacagc aagaaacaat   1260
gtcttgggcc atagaagcac tcaatcgtcc gcaatttttc caggatagac aggaggctgc   1320
tcaatatata gcttctgttt attcgagtgg gcaaagtact caaatggctc ttgaaaacaa   1380
agcctttgtt ggagaacagc ttgggggcac aagaatggac gtcatgaatg aaagcactat   1440
gatccggagt tcatctttga gagtcccaac tctcaaagtg cagagcaagc gcttcccgtc   1500
catggaactg ccggctgtaa gtacatcatc cttactcagc acacgtgaag aaacagttca   1560
tgatgaggat gattgtgggg gattgtttcc agcacccaag aaaaagggcc aagccttcaa   1620
catgggtgcc atttgggata atttgggcat ggagtcgttc gcacacattg atttcccaga   1680
tgattggaca gaacgaacaa tagctcagca ggtacaattt atcctcttta gtgaggctaa   1740
aagaggaaac gttattgtgc caagacatgt tgcaaagcgg catctgcata atatcaatag   1800
ggagcacata accgaggaca attatgtaga aatacttgaa ggttatggtg ttaccaatat   1860
ccaaggcttg actcgcactt tcaattggta tgctatgtct ctcaaggaga gagttgtgga   1920
gctcgtccat caaagagatc attccttcta tattcaaggg cagactaaca atccaatgcc   1980
gaattttgac tgctatgatg gattaacctt gaaagagcgt cagttgattg tggaggagca   2040
agtggcccaa agaaggtctg aaagacaagc acaggtgaca gcaaggggca tagctgaaag   2100
tcagcctgaa gacagagtga ctgattcctt tgtgtcaact accacgatgg aagatcccac   2160
caagccagat aagatagaaa ttgttgcaga gggagcagaa gaagaaactc aacctggtga   2220
tgttattttt gactttggac cagaaatgga cacatccatg gcagttgaac tggatatgca   2280
gcaaccggtg tgtgtagcta gcaatgattt cttcaatgtt ggagtttttg aattcgtttg   2340
ggagaagtcc gctaatgttg ctgagcaagt aatgagcttg gctttgcccg ctgccctatt   2400
ctcaaaaagc aaagaaactt caatgggtgc gcaaatgctt aagtattacg atgcagctct   2460
aatcatgtac aaaataatac tttatgtttc tggagttgga gctatctctg gtcaactggc   2520
tttggtgtgg gatgaatgta atgtgcttaa tcgaaagaag gaattcatca acatcgccac   2580
attgtatgcc agtaagcaca cattggtttc agcttcacaa cagaacagtg aggagttttg   2640
```

-continued

```
ctttacccca acagggatag gcaagtacgt gcctctggat gaaggtacag gagccactga   2700
tttaggtagt gtgagagtgt ttgtgacaca ccccttatct agtgcaactg agttgaatag   2760
tgtaccatgc catttgcact tacagtgcaa agtgttatca accaatatac ttcaacctcc   2820
acgaatgata gcacaggctc aatatggcat gaaggcgggg cagacatatt ttccaaggtt   2880
tccaactaat caggttttgt tacattataa ttggggggaca tcatccccaa tgggaactac   2940
attggtaagc atattttcac catcaggaat atatgagagt gatggcacct tgcagccgtc   3000
tttgcttggt aacatagcca ggaattgcaa gtggtggact ggaacttgtg tttttgaaat   3060
ttgcattgag aaaaccttgt ttcattcagg tagtctggca attggacttg gaactctgaa   3120
caccaaaatg accaatgctc atgatatatt taacatgcca catgtggtat gcaatcttga   3180
aatgggtcga aaatttcggt tccggtgttc tattacaaat tggaatggaa aaaatttgct   3240
ttccacaggg cgaaagagtt ccttgccaag accacagcac ttttcccact tgcgcttgtt   3300
tgcaacggta atgaagccac tcgtttcaac gtccatacat ctggattccg ttggtgtcac   3360
agtgcagttg aagtgccttg aaaatcttac tttgggtggc acagtatctg tgaaaccaat   3420
atatgggcat tggacaaaag gcaaaagctc agttgatttc cttttctctg aaatggattt   3480
atcacagcgt aaggaaattg aaaagttgag aaaggacaac attgaggagt accaggagaa   3540
aggcaaagat ccgcccaaga aggctcaaag tattctgtcc ataagagaga aattttccta   3600
tggtgctgta caatatttct gcatgggttg gaaggatgac gaaagattgt tggtaattcc   3660
ttgtgcacca tggtccataa ggtttgaagg gcacagtcct gttaaggagg caatcacttg   3720
tccatttata gattggtgta catcattttg ttattggtca ggtagtttga attattcaat   3780
tgtgatacac agagtacaat ccagtcctaa tgttggaggt gtactaaatg ttgcttttga   3840
tgcctcaggc tatccttttc cagctgggct taataaagga aattatgtgg tatcagcagg   3900
tggaggcaca aaatgggatt tttcatacgg tgtggcaaca aatacgttct cattcactgt   3960
gcaagatgat gagtttttcc caaggcggca tacaaggatg agggaattct caagcaagca   4020
atcccgcatc atgtcactac aggataggct tggaaatctg atcataaatt tgcctccttc   4080
cgccatagtg agttccattg agatacttat atctcctgga cttgatttca agttggagtt   4140
ggcccaacct ccttctgcca accatgaaaa atatcttggc aatatgcaaa ctcacaccta   4200
tcagtatacc tcagattttt ctgagctacg tgattttgcg atttgaaaaa gtaccatgct   4260
actgggtata tagtagccaa atacacttat ctacgtgtac tgttagtagt agctaagtgg   4320
tgtttgtttg caatgataag ggagagttaa gggagagtac tgtcttttaa tagatgggag   4380
tcccctccac ttcatggaga ccaatgaatc tacattggta tagaggtttg cacgctcctc   4440
tttaaataag tttcgtgtgc cctgcttggt tagaaagcat gtggtgatta acactactcg   4500
tttggagtat aagcaataga cctcatgatg tctaactcat gcgtgattgc tcatgtacga   4560
aataaatgag ccgtttggaa ctcgataatt tcctttagct gctgtacagc tgtcactatt   4620
aggggtagtg gcgaagttgt gagtcccctc ttcctcccta ggttcgtcca gagggttcaa   4680
agattcacct tctttgtcaa gaagcgatga atgacacgtg ttgcgtcgac aaagcaccgt   4740
tctacgtggt tagtagaaag ttatattata ttagatttgt tagtcaattg tgtgatttct   4800
ttcctagatt aggaagtttt ccgtggcgat aggaagggtt tgtcctttta ccttctttgc   4860
tatgctggac acaaaaagat tttcttttct tttattttaa aaaaaa                  4906
```

PLANT VIRUS DESIGNATED TOMATO MARCHITEZ VIRUS

RELATED APPLICATIONS

This application is a continuation of PCT application number PCT/NL2008/050076 designating the United States and filed Feb. 8, 2008; which claims the benefit of U.S. patent application Ser. No. 11/759,603 filed Jun. 7, 2007 (abandoned); both of which are hereby incorporated herein by reference in their entireties.

FIELD OF THE INVENTION

The present invention is in the field of plant disease. More in particular, the invention relates to a new plant virus isolated from tomato, to methods for detecting said virus, to methods of detecting resistant plants and to methods for producing resistant plants.

BACKGROUND OF THE INVENTION

The tomato *Solanum lycopersicum* (formerly *Lycopersicon esculentum*) is susceptible to a large number of viral species. Some of the most prominent tomato viruses include Tomato spotted wilt virus (TSWV; genus Tospovirus); Pepino mosaic virus (PepMV; genus Potexvirus), and Tomato yellow leaf curl virus (TYLCV; genus Begomovirus). The damage that these diseases inflict on the plant range from discoloration of leaves and necrotic lesions, to severe crop loss and death of the plant.

The ability to provide resistant plants is of utmost importance to commercial breeders, and for some of the economically most damaging viruses, resistant plant varieties have been produced. However, from time to time, new viruses emerge that may inflict considerable damage on crops.

In 1996 a new tomato virus was reported which had infected tomato plants in the USA and Italy since 1993, and was named Tomato infectious chlorosis virus (TICV; genus Crinivirus; Duffus et al., 1996). Another new tomato virus of the same genus was reported in 1998. This virus was shown to have infected tomato plants in the USA since 1989 and was named Tomato chlorosis virus (ToCV; Wisler et al., 1998). Both these new viruses proved to be spread by a whitefly, the insect being a very effective disease-transmission vector.

It is generally believed that the geographic distribution of known viruses will increase and that new viruses will continue to appear, partly as a result of recombination of different viruses to form new strains or new viruses. The development of resistant cultivars can play an important role in the successful management of these diseases.

SUMMARY OF THE INVENTION

Recently, a new virus was discovered on tomato plants from Spain, which caused symptoms that could not be attributed to any known virus. The plants exhibited necrotic lesions on leaves and brown rings on fruits and showed reduced growth. Serological tests (ELISA) indicated the presence of Pepino mosaic virus (PepMV). Electron microscopic investigations indeed revealed the rod-like particles typical for potexviruses. However, also spherically shaped viral particles were found in infected leaf tissue. The inventors were able to separate the new virus from the complex with PepMV. The new virus was tentatively named Tomato torrado virus (ToTV).

Following the discovery of the ToTV virus, a new and very related virus was isolated from a tomato plant from the state of Sinaloa in Mexico. This plant showed symptoms locally known as 'marchitez disease', including severe leaf necrosis, beginning at the base of the leaflets, and necrotic rings on the fruits. (This disease should not be confused with another virus known to cause what is called in Mexico "marchitez manchada del tomate", the causative agent of which is tomato spotted wilt virus (TSWV) or Virus de la Marchitez Manchada del Tomate (VMMT), [see e.g. De La Torre-Almaráz et al. Agrociencia 36: 211-221. 2002]). Virus particles isolated from the infected plants are isometric with a diameter of approximately 28 nm. The viral genome consists of two (+)ss-RNA molecules of 7221 (RNA1) and 4906 nucleotides (RNA2). The viral capsid contains three coat proteins of 35, 26 and 24 kDa respectively. The above mentioned characteristics; symptoms, morphology, number and size of coat proteins, and number of RNAs, are similar to the previously described tomato torrado virus (ToTV). Sequence analysis of the entire viral genome shows that this new virus is related to, but distinct from ToTV and, together with ToTV belongs to a new plant virus genus. For this new virus the name tomato marchitez virus (ToMarV) is proposed.

For being able to trace its origin, monitor its epidemiology and prevent possible spreading of the disease, it is of great importance to be able to recognise the disease in an early stage. Only then sufficient measures can be taken to isolate plants and initiate phytosanitairy precautions. At this moment no diagnostic tools are available. Consequently, there is a need for developing diagnostic tools for this disease. Furthermore, at present there are no plants known that harbour specific resistance to this new virus, while there is a need for developing such resistant plants.

The invention provides in a first aspect a plant virus tentatively named Tomato Marchitez virus (ToMarV), deposited with the Deutsche Sammlung von Mikroorganismen und Zellkulturen (DSMZ) in Braunschweig, Germany, on 10 Jul. 2007 under depositors reference number PRI-TMarV0601 (DSM 19656).

ToMarV is part of a novel genus of plant viruses of which ToTV is the type strain. When reference is made herein to "ToTV", the broad genus of viruses sharing the homology levels as indicated herein is intended, unless otherwise specified. This broad genus includes ToTV-E01 (DSM 16999) as well as PRI-TMarV0601, deposited on Jul. 10, 2007 with the Deutsche Sammlung von Mikroorganismen and Zellkulturen GmbH in Braunschweig, Germany, an International Depository Authority under the Budapest Treaty. The deposited material received the accession number DSM 19656. All restrictions upon the deposit will be irrevocably removed upon the granting of a patent, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

The virus causes disease-symptoms in tomato plants as well as in other plants, and may cause the symptoms by itself, or in a complex with other viruses or diseases.

The first systemic symptoms consist of necrotic spots at the top of the plant, starting at the base of the leaves of a leaflet. Necrotic spots expand and are surrounded by a light-green or yellow area (see FIG. 1). Not all systemic infected leaves show symptoms, however, the virus can be detected in these leaves, for instance by electron microscopy. Fruits infected with ToTV exhibit necrotic rings. The growth of infected plants may be reduced compared to non-infected plants.

The above description relates to plants newly infected with the isolated virus and need not necessarily reflect the exact symptoms encountered in the field. Factors such as plant race or variety, development stage, additional disease pressure, and abiotic factors (e.g. temperature and relative humidity) will eventually determine the expression and characteristics of the symptoms.

The viral particles are spherical (icosahedral) in shape with a diameter of approximately 28 nm (see FIG. 2). Virus particles consist of at least three capsid proteins of approximately 23, 26 and 35 kDa (see FIG. 3). Upon purification, the virus displays at least two visible bands in a cesium sulfate gradient. The upper visible band (virus top fraction) contains an RNA molecule of approximately 5.5 kb (more precisely 5.2 kb) and the lower visible band (bottom fraction) contains an RNA molecule of approximately 8 kb (more precisely 7.7 kb) (see FIG. 4). The inoculation of both bands combined on tobacco plants results in an infection.

ToTV is mechanically transmissible to several *Nicotiana* species. A standard inoculation buffer (e.g. a 0.03 M phosphate buffer at pH 7.7) is suitable. For propagation of ToTV, *N. glutinosa, N. tabacum* and *N. benthamina* are preferred. The tobacco species *N. hesperis* '67A' and *N. occidentalis* 'P1' are very sensitive to ToTV and show systemic symptoms after 3-4 days. These tobacco species become very necrotic in short time and are therefore more suitable for use as an indicator plant than as propagation host. *N. glutinosa* reacts with chlorotic local lesions and a systemic chlorosis and mild deformation of the leaves. *N. benthamiana* does not show local symptoms and reacts with systemic chlorosis and deformation of the leaves.

The invention further provides a virus comprising at least one nucleic acid sequence selected from the group consisting of SEQ ID NO:1 and SEQ ID NO:2 and sequences having a nucleotide sequence homology of at least 30, preferably at least 40, preferably at least 50%, preferably at least 60%, more preferably at least 70%, more preferably at least 80%, still more preferably at least 90%, still more preferably at least 95%, still more preferably at least 98%, and most preferably at least 99% thereto. Such viruses are also encompassed by the term ToTV as used herein.

In a preferred embodiment of a virus of the invention having the above referred sequence homology, said virus is associated with tomato diseases known under the names of "Torrado", "Marchitez" and/or "Chocolate spot disease", and/or said virus shows, based on numerical taxonomic analysis of taxonomic descriptors essentially as defined in Table 1, to be more closely related to the virus as defined in claim 1 than to any other viral isolate available in public collections, and said virus has as an essential characteristic that it is associated with a disease that causes necrotic lesions in tomato.

In another aspect, the invention provides an isolated or recombinant nucleic acid comprising a nucleic acid sequence selected from the group consisting of SEQ ID NO:1, SEQ ID NO:2, sequences having a nucleotide sequence homology of at least 50%, preferably at least 70%, more preferably at least 80%, still more preferably at least 90%, still more preferably at least 95%, still more preferably at least 98%, and most preferably at least 99% to SEQ ID NO:1 or SEQ ID NO:2, and their complementary strands and ToTV-specific fragments thereof. Such a nucleic acid may be obtained from a virus according to the invention.

In another aspect, the invention provides a polynucleotide capable of hybridizing under stringent conditions to the isolated or recombinant nucleic acid of the invention as described above.

In another aspect, the invention provides an isolated or recombinant polypeptide obtainable from a virus according to the invention, or a ToTV-specific fragment thereof. In a preferred embodiment said polypeptide is selected from the group consisting of the 23, 26 and 35 kDa capsid proteins of ToTV and ToTV-specific fragments thereof.

In another aspect, the invention provides an antigen comprising a polypeptide or ToTV-specific fragment thereof according to the invention.

In another aspect, the invention provides an antibody specifically directed against an antigen according to the invention.

In another aspect, the invention provides a method for producing an antibody against ToTV comprising the steps of: a) providing a ToTV virus, or a (recombinant) protein or peptide fragment thereof; b) immunizing an appropriate vertebrate host with said virus, protein or peptide fragment, and c) harvesting from blood (including serum) or splenocytes of said vertebrate host antibodies against said virus, protein or peptide fragment. In a preferred embodiment said method further comprises the steps of d) selecting one antibody-producing splenocyte, e) fusing said splenocyte to an immortalized hybridoma cell line and f) allowing said hybridoma fusion to produce monoclonal antibodies.

In another aspect, the invention provides an antibody obtainable by a method of producing an antibody against ToTV according to the invention.

In another aspect, the invention provides a method for identifying a viral isolate as a ToTV virus comprising reacting said viral isolate or a component thereof with an antibody according to the invention.

In another aspect, the invention provides a method for identifying a viral isolate as a ToTV virus comprising reacting said viral isolate or a component thereof with a polynucleotide according to the invention.

In another aspect, the invention provides a method for detecting the presence of ToTV in a sample comprising determining in said sample the presence of a ToTV virus or component thereof by reacting said sample with a polynucleotide or an antibody according to the invention.

In another aspect, the invention provides a method for identifying a ToTV-resistant plant comprising the steps of: a) exposing a plant or plant part to an infective dosage of ToTV, and b) identifying said plant as a ToTV-resistant plant when, after said exposure, either i) disease-symptoms in said plant or plant part remain absent or are delayed in expression or are at least reduced in severity relative to a susceptible control plant, and/or ii) ToTV virus or ToTV genomic sequences are not present in said plant or plant part or the presence of ToTV virus is at least quantitatively reduced in said plant relative to a susceptible control plant. Step a) includes an incubation period for a duration sufficiently long to allow for the establishment of detectable disease-symptoms in susceptible control plants exposed to a comparable infective dosage of virus. By performing this method all forms of resistance, including full resistance, partial resistance, hypersensitivity and tolerance may be identified in a plant. In order to confirm tolerance, the (systemic) presence of the virus in the plant (cells) must be confirmed. Step b) may involve performing a method for detecting the presence of ToTV in a sample of said plant or plant part according to the present invention wherein use is made of an antibody or polynucleotide according to the invention in standard methods for nucleotide hybridization assays or immunoassays, well known to the skilled person. Alternatively, step b) may comprise contacting a part of said exposed plant with a susceptible indicator plant. In this way, one may detect the presence of a systemic or local infection in said exposed plant through observing the emergence of disease in the indicator plant or even a further contacted indicator plant contacted with said first contacted indicator plant.

In another aspect, the invention provides a method of producing a ToTV-resistant plant comprising the steps of identifying a ToTV-resistant donor plant by performing either of the above methods for identifying a ToTV-resistant plant according to the invention, crossing said ToTV-resistant donor plant with a recipient plant (which recipient plant may be either ToTV-susceptible or ToTV-resistant, but is suitably a ToTV-resistant plant in case the resistant phenotype is brought about by a recessive gene), and selecting from an offspring plant (e.g. an $F_1$, an $F_2$, and a selfed plant) a resistant plant by performing a method for identifying ToTV resistance in a plant as described above. In the instance that the resistance trait is a recessive trait, resistant plants may be found among offspring plants of the selfings of the F1 or F2 or still further generations. In preferred embodiments of this aspect, said ToTV-resistant donor plant and the recipient plant are plants of the family Solanaceae or family Cucurbitaceae. In other preferred embodiments of this aspect, said recipient plant is a tomato plant, eggplant plant, pepper plant, melon plant, watermelon plant or cucumber plant, more preferably a plant of the species *Solanum lycopersicum*, most preferably an *S. lycopersicum* line that possesses commercially desirable characteristics.

In another aspect, the invention provides a ToTV-resistant plant, preferably a tomato plant, eggplant plant, pepper plant, melon plant, watermelon plant or cucumber plant, or part thereof, such as a seed, obtainable by a method of producing a ToTV-resistant plant according to the invention.

In another aspect, the invention provides a diagnostic kit for detecting the presence of ToTV in a sample or for identifying ToTV resistance in a plant comprising a virus, a polynucleotide, a polypeptide, an antigen and/or an antibody according to the invention.

In another aspect, the invention provides the use of a virus, a polynucleotide, a polypeptide, an antigen or an antibody according to the invention for the production of a diagnostic composition.

In another aspect, the invention provides a diagnostic composition comprising a virus, a polynucleotide, a polypeptide, an antigen or an antibody according to the invention.

In another aspect, the invention provides the use of ToTV, or parts of the ToTV viral genome, as an expression vector.

In another aspect, the invention provides the use of ToTV, or parts of the ToTV viral genome, for producing pathogen-derived resistance in plants.

In another aspect, the invention relates to the use of an attenuated form of a ToTV virus, or its genome, or parts thereof, for premunition of a plant.

DETAILED DESCRIPTION OF THE INVENTION

Definitions

As used herein the term "ToTV", is to be interpreted as referring to the new genus of viruses sharing the RNA homology levels as indicated herein, unless expressly stated or intended otherwise (for instance when ToMarV and ToTV are compared, the term ToTV should be interpreted as referring to the species ToTV-E01. This broad genus includes at least the species ToTV-E01 (DSM 16999) as well as the PRI-TMarV0601. The genus is defined by the homology levels between RNA sequences of the viral genome (or translated into DNA sequences); or the homology levels between amino acid sequences of open reading frames within the viral genome.

As used herein the term "ToTV-resistant", is to be interpreted as referring to the resistance of a plant, in particular a tomato plant to the establishment of an infection, or the establishment of a disease caused by a viral species of the new genus of viruses sharing the RNA homology levels as indicated herein, unless expressly stated or intended otherwise.

The term "ToTV-specific fragment" as used herein refers to a nucleic acid fragment having a sequence that is specific for the genus of viruses comprising ToTV and ToMarV as described herein, With the term "specific" is meant that the nucleic acid is capable of hybridizing specifically under stringent hybridization conditions to the nucleic acid of said virus.

As used herein the term "ToMarV" is to be interpreted as referring to a species within the new genus of ToTV viruses which genus shares the RNA homology levels as indicated herein, unless expressly stated or intended otherwise (for instance when ToMarV and ToTV are compared herein, the term ToMarV should be interpreted as referring to the species PRI-TMarV0601). The term "ToMarV" is also to be interpreted as referring to a virus belonging to this novel species within the new genus of ToTV viruses which genus wherein said novel species shares homology levels on nucleotide or amino acid sequence levels generally accepted among virologists to indicate different isolates (strains) belonging to the same species. Such intraspecific homologly levels are usually above 80 to 90%, for instance above 93% for nucleotide sequences, and possibly even higher for amino acid sequences.

As used herein, the term "plant part" indicates a part of a plant, including single cells and cell tissues such as plant cells that are intact in plants, cell clumps and tissue cultures from which plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

The term "sample" includes a sample from a plant, from a plant part or from a transmission vector, or a soil, water or air sample.

The term "transmission vector" as used herein refers to the disease-spreading agent or substance. Transmission vectors of ToTV in the field may comprise, but are not limited to animals such as Arthropoda (in particular those of the classes Insecta and Arachnida), Nematoda (in particular those of the class Adenophorea), but also larger animals such as for instance birds, rabbits and mice, fungi (i.e. phylum Eumycota, in particular fungi of the class Phycomycota), (parasitic) plants (including members of the family Cuscutaceae), pollen, seed, water, soil particles, and even human hands, equipment and shoes.

The term "offspring" plant refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The term "resistant", as used herein, refers to a plant that is capable of resisting the multiplication in its cells and/or the (systemic) movement of the virus to other cells and/or the development of disease symptoms after infection with said virus, which virus is capable of infecting and multiplying in corresponding non-resistant or susceptible varieties of said plant. The term is used to include such separately identifiable forms of resistance as "full resistance", "immunity", "partial resistance", "hypersensitivity" and "tolerance".

"Full resistance" is referred to as complete failure of the virus to develop after infection, and may either be the result of failure of the virus to enter the cell (no initial infection) or may be the result of failure of the virus to multiply in the cell and infect subsequent cells (no subliminal infection, no spread). The presence of full resistance may be determined by establishing the absence of viral particles or viral RNA in cells of the plant, as well as the absence of any disease symptoms in said plant, upon exposure of said plant to an infective dosage of virus (i.e. after 'infection'). Among breeders, this phenotype is often referred to as "immune". "Immunity" as used herein thus refers to a form of resistance characterized by absence of viral replication even when virus is actively transferred into cells by e.g. electroporation.

An "infective dosage" is defined as a dosage of viral particles or virus nucleic acid capable of infecting a plant, which dosage may vary between plants and between ToTV-isolates tested. Theoretically, an amount of about 1 to 10 to an amount of about 500-5000 viral particles of said virus or the nucleic acids thereof will be sufficient. Infection in this way may be achieved by mechanical inoculation of purified virus particles or virus nucleic acid on plants.

"Partial resistance" is referred to as reduced multiplication of the virus in the cell, as reduced (systemic) movement of the virus, and/or as reduced symptom development after infection. The presence of partial resistance may be determined by establishing the systemic presence of low titres of viral particles or viral RNA in the plant and the presence of decreased or delayed disease-symptoms in said plant upon exposure of said plant to an infective dosage of virus. Virus titres may be determined by using a quantitative detection method (e.g. an ELISA method or a quantitative reverse transcriptase-polymerase chain reaction [RT-PCR]). Among breeders, this phenotype is often referred to as "intermediate resistant".

The term "hypersensitive" refers to a form of resistance whereby the infection remains local and does not systemically spread, for instance due to local necrosis of infected tissue or lack of systemic movement beyond inoculated tissue. Hypersensitive plants show local, but severe disease symptoms and the local presence of the virus can be established in such plants.

"Tolerant" is used herein to indicate a phenotype of a plant wherein disease-symptoms remain absent upon exposure of said plant to an infective dosage of virus, whereby the presence of a systemic or local viral infection, virus multiplication, at least the presence of viral genomic sequences in cells of said plant and/or genomic integration thereof can be established. Tolerant plants are therefore resistant for symptom expression but symptomless carriers of the virus. Sometimes, viral sequences may be present or even multiply in plants without causing disease symptoms. This phenomenon is also known as "latent infection". Some DNA and RNA viruses, may become undetectable following a primary infection only to reappear later and produce acute disease. In latent infections, the virus may exist in a truly latent non-infectious occult form, possibly as an integrated genome or an episomal agent (so that viral particles cannot be found in the cytoplasm, while PCR protocols may indicate the present of viral nucleic acid sequences) or as an infectious and continuously replicating agent. A reactivated virus may spread and initiate an epidemic among susceptible contacts. The presence of a "latent infection" is indistinguishable from the presence of a "tolerant" phenotype in a plant.

The term "susceptible" is used herein to refer to a plant having no resistance to the virus resulting in entry of the virus into the plant's cells and multiplication and systemic spread of virus, resulting in disease symptoms. The term "susceptible" is therefore equivalent to "non-resistant". A susceptible plant exhibits normal virus titres in its cells upon infection. Susceptibility may thus be determined by establishing the presence of normal (i.e. relative to other viral infections in plants) titres of viral particles or of viral RNA in cells of the plant and the presence of normal disease symptoms (i.e. relative to the disease symptoms as herein described for the plant from which ToTV was first isolated) in said plant upon exposure of said plant to an infective dosage of virus.

The term "sensitive" reflects the symptomatic reaction of a susceptible plant upon virus infection. The reaction or symptoms can be more or less severe depending on the level of sensitivity of the plant. If the plant is injured or even killed by the virus, said plant is qualified as "sensitive".

Plants artificially inoculated with attenuated virus strains are subsequently protected from closely related virulent viruses. As protective viruses, either naturally occurring mild strains or an attenuated strain (an artificially-induced mild mutant) may be used. Preferably, in order to attain premunition of a plant against ToTV, an attenuated strain of ToTV may be used that is symptomless or that shows at least reduced symptom expression in an infected plant, relative to a virulent strain of ToTV. Methods of producing attenuated virus may for instance include random mutagenesis of the ToTV genome and screening for strains with symptom attenuation. Express reference is made to the methods for producing attenuated plant viruses as described in the articles of Takeshita et al., 2001; Lu et al., 2001; Hagiwara, et al., 2002; and Hirata et al., 2003.

As used herein, the term "tomato" means any plant, line or population of *Lycopersicon* or *Solanum* that includes, but is not limited to, those presented in the Listing below. Recently, nomenclature of *Lycopersicon* has been changed.

The new nomenclature for *Lycopersicon* is provided in the following Listing (from: Peralta, Knapp & Spooner, unpublished monograph (see: World Wide Website sgn.cornell.edu "Guide to revised *Solanum* nomenclature")).

| Name in tomato monograph (Peralta et al., in preparation for publication in Systematic Botany Monographs) | *Lycopersicon* equivalent |
|---|---|
| *Solanum juglandifolium* Dunal | *Lycopersicon juglandifolium* (Dunal) J. M. H. Shaw |
| *Solanum ochranthum* Dunal | *Lycopersicon ochranthum* (Dunal) J. M. H. Shaw |
| *Solanum sitiens* I. M. Johnst. | *Lycopersicon sitiens* (I. M. Johnst.) J. M. H. Shaw |
| *Solanum lycopersicoides* Dunal | *Lycopersicon lycopersicoides* (Dunal in DC.) A. Child ex J. M. H. Shaw |
| *Solanum pennellii* Correll | *Lycopersicon pennellii* (Correll) D'Arcy |
| *Solanum habrochaites* S. Knapp & D. M Spooner | *Lycopersicon hirsutum* Dunal |

-continued

| Name in tomato monograph (Peralta et al., in preparation for publication in Systematic Botany Monographs) | *Lycopersicon* equivalent |
|---|---|
| *Solanum* '*N peruvianum*' to be described by Peralta (4 geographic races: humifusum, lomas, Marathon, Chotano-Yamaluc) | Part of *Lycopersicon peruvianum* (L.) Miller (incl. var. *humifusum* and Marathon races) |
| *Solanum* 'Callejon de Huaylas' to be described by Peralta | Part of *Lycopersicon peruvianum* (L.) Miller (from Ancash, alogn Rio Santa) |
| *Solanum neorickii* D. M. Spooner, G. J. Anderson & R. K. Jansen | *Lycopersicon parviflorum* C. M. Rick, Kesicki, Fobes & M. Holle |
| *Solanum chmielewskii* (C. M. Rick, Kesicki, Fobes & M. Holle) D. M. Spooner, G. J. Anderson & R. K. Jansen | *Lycopersicon chmielewskii* C. M. Rick, Kesicki, Fobes & M. Holle |
| *Solanum corneliomuelleri* J. F. Macbr. (1 geographic race: Misti nr. Arequipa) | Part of *Lycopersicon peruvianum* (L.) Miller; also known as *Lycopersicon glandulosum* C. F. Mull. |
| *Solanum peruvianum* L. | *Lycopersicon peruvianum* (L.) Miller |
| *Solanum chilense* (Dunal) Reiche | *Lycopersicon chilense* Dunal |
| *Solanum cheesmaniae* (L. Riley) Fosberg | *Lycopersicon cheesmaniae* L. Riley (published as *cheesmanii*) |
| *Solanum galapagense* S. Darwin & Peralta | Part of *Lycopersicon cheesmaniae* L. Riley (previously known as forma or var. minor) |
| *Solanum lycopersicum* L. | *Lycopersicon esculentum* Miller |
| *Solanum pimpinellifolium* L. | *Lycopersicon pimpinellifolium* (L.) Miller |

An "expression vector" is defined as a nucleic acid molecule containing a gene, usually a heterologous gene, that is expressed in a host cell. Typically, this gene comprises a protein encoding sequence. Gene expression is always placed under the control of a promoter, and such a gene is said to be "operably linked to" the promoter. The term "heterologous" refers to a DNA molecule, or a population of DNA molecules, that does not exist naturally within a given host cell.

The term "polynucleotide" as used herein, is interchangeable with the term "nucleic acid", and refers to a nucleotide multimer or polymeric form of nucleotides having any number of nucleotides, e.g., deoxyribonucleotides or ribonucleotides, or compounds produced synthetically (e.g. PNA as described in U.S. Pat. No. 5,948,902 and the references cited therein) and can be either double- or single-stranded. A polynucleotide can hybridize with naturally occurring polynucleotides in a sequence specific manner analogous to that of two naturally occurring polynucleotides, e.g. can participate in Watson-Crick base pairing interactions. The term also includes modified, for example by methylation and/or by capping, and unmodified forms of the polynucleotide.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" refers to a short sequence of nucleotide monomers (usually 6 to 100 nucleotides) joined by phosphorous linkages (e.g., phosphodiester, alkyl and arylphosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming secondary structures (e.g., stem-loop, pseudo knots and kissing loop structures).

The term "nucleotide sequence homology" as used herein denotes the presence of homology between two polynucleotides. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST) (Altschul et al., 1990; Altschul et al., 1997) and ClustalW programs, both available on the internet. Other suitable programs include, but are not limited to, GAP, BestFit, PlotSimilarity, and FASTA in the Wisconsin Genetics Software Package (Genetics Computer Group (GCG), Madison, Wis., USA) (Devereux et al., 1984).

As used herein, "substantially complementary" means that two nucleic acid sequences have at least about 65%, preferably about 70%, more preferably about 80%, even more preferably 90%, and most preferably about 98%, sequence complementarity to each other. This means that primers and probes must exhibit sufficient complementarity to their template and target nucleic acid, respectively, to hybridise under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

The term “hybrid” in the context of nucleic acids refers to a double-stranded nucleic acid molecule, or duplex, formed by hydrogen bonding between complementary nucleotide bases. The terms “hybridise” or “anneal” refer to the process by which single strands of nucleic acid sequences form double-helical segments through hydrogen bonding between complementary bases.

The term “hybrid” in the context of plant breeding refers to a plant that is the offspring of genetically dissimilar parents produced by crossing plants of different lines or breeds or species.

The term “probe” refers to a single-stranded oligonucleotide sequence that will recognize and form a hydrogen-bonded duplex with a complementary sequence in a target nucleic acid sequence analyte or its cDNA derivative.

The term “primer” as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

It will be understood that “primer”, as used herein, may refer to more than one primer, particularly in the case where there is some ambiguity in the information regarding the terminal sequence(s) of the target region to be amplified. Hence, a “primer” includes a collection of primer oligonucleotides containing sequences representing the possible variations in the sequence or includes nucleotides which allow a typical base pairing.

The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in e.g. U.S. Pat. No. 4,458,066. The primers may be labeled, if desired, by incorporating means detectable by for instance spectroscopic, fluorescence, photochemical, biochemical, immunochemical, or chemical means.

Template-dependent extension of the oligonucleotide primer(s) is catalyzed by a polymerizing agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, T4 DNA polymerase, and Taq DNA polymerase. The reaction conditions for catalyzing DNA synthesis with these DNA polymerases are known in the art.

The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a “short” product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method is well described in handbooks and known to the skilled person.

After amplification by PCR, the target polynucleotides may be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions will be used. If some mismatching is expected, for example if variant strains are expected with the result that the probe will not be completely complementary, the stringency of hybridization may be lessened. However, conditions are chosen which rule out nonspecific/adventitious binding. Conditions which affect hybridization, and which select against nonspecific binding are known in the art, and are described in, for example, Sambrook et al., (2001). Generally, lower salt concentration and higher temperature increase the stringency of binding. For example, it is usually considered that stringent conditions are incubations in solutions which contain approximately 0.1×SSC, 0.1% SDS, at about 65° C. incubation/wash temperature, and moderately stringent conditions are incubations in solutions which contain approximately 1-2×SSC, 0.1% SDS and about 50°-65° C. incubation/wash temperature. Low stringency conditions are 2×SSC and about 30°-50° C.

The terms “stringency” or “stringent hybridization conditions” refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridises to a perfectly matched probe or primer. Typically, stringent conditions will be those in which the salt concentration is less than about 1.0 M $Na^+$ ion, typically about 0.01 to 1.0 M $Na^+$ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001.

The term "antigen" refers to a substance capable of triggering an immune response in a vertebrate, resulting in production of an antibody as part of the defence against said substance. Antigens can be virus proteins that can provoke the antibody production in for instance blood cells, cells of lymph nodes, and spleen of vertebrates.

The term "antibody" includes reference to antigen binding peptides and refers to antibodies, monoclonal antibodies, to an entire immunoglobulin or antibody or any functional fragment of an immunoglobulin molecule. Examples of such peptides include complete antibody molecules, antibody fragments, such as Fab, $F(ab')_2$, complementarity determining regions (CDRs), VL (light chain variable region), VH (heavy chain variable region), and any combination of those or any other functional portion of an antibody peptide. The term "antibody" refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The terms "substantially pure" and "isolated", are used interchangeably and describe a protein, peptide or nucleic acid which is substantially separated from other (sub)cellular components which naturally accompany it. The term embraces a nucleic acid or protein which has been removed from its naturally occurring environment, and includes recombinant or cloned DNA isolates and chemically synthesized analogues or analogues biologically synthesized by heterologous systems. Generally, the term refers to a purified protein and nucleic acid having a purity of at least about 75%, for example 85%, 95% or 98% by weight. Minor variants or chemical modifications typically share the same polypeptide or nucleotide sequence. A substantially pure protein or nucleic acid will typically comprise about 85 to 100% (w/w) of a protein or nucleic acid sample, more usually about 95%, and preferably will be over about 99% pure. Protein or nucleic acid purity or homogeneity can be indicated by a number of means well known in the art, such as polyacrylamide gel electrophoresis of a protein sample, followed by visualizing a single polypeptide band on a polyacrylamide gel upon staining, or by agarose gel electrophoresis of a nucleic acid sample, followed by visualizing a single polynucleotide band on an agarose gel upon staining. "Staining" may either refer to the use of a-specific peptide or nucleic acid stains such as silver and Coomassie stains, or ethidium bromide and SYBR® stains, or may refer to the use of specific peptide or nucleic acid stains such as contacting the peptide with an antibody and visualizing the antibody using a labeled secondary antibody (e.g. conjugated to alkaline phosphatase) in the case of proteins or peptides, or contacting the nucleic acid with a complementary probe labelled for visualizing the presence of hybridization between the nucleic acid and the probe. For certain purposes higher resolution can be provided by using high performance liquid chromatography (HPLC) or a similar means for purification. Such methods are in the area of common general knowledge (see e.g. Katz, et al., 1998)

Identification and Taxonomy

The invention provides an isolated virus comprising at least one nucleic acid sequence according to SEQ ID NO:1 and/or SEQ ID NO:2 and sequences having a nucleotide sequence homology of at least 30%, 35%, 40%, 45%, 50%, 55%, 60% or preferably 65% thereto. As stated above, polynucleotides have "homologous" sequences if the sequence of nucleotides in the two sequences is the same when aligned for maximum correspondence. BLAST searches using nucleotide sequences obtained from the ToTV virus isolate previously revealed no significant homologies with any of the known viral or non-viral sequences in the GenBank and EMBL databases. Highest percentage homology found thus far was 46.5% between the helicase motifs in ORF1 on SEQ ID NO:2 corresponding to ToTV RNA1 with helicase motifs of other plant viruses. (see Examples below).

ToMarV shares virion characteristics and its genome organization with ToTV-E01, but based on levels of nucleotide and amino acid sequence identities the two viruses are related but distinct. BLAST searches in the GenBank and EMBL databases recently revealed a significant homology with another recently isolated virus. Remarkably high levels of identities are observed between ToMarV RNA1 and RNA2 and partial sequences of RNA1 and RNA 2 of a virus of which the sequence was deposited on 16 Oct. 2006 in the NCBI database under the name of tomato apex necrosis virus (Genbank accessions EF063641 and EF063642; hereinafter ToANV). This virus appears also to be obtained from the Culiacan area (Sinaloa, Mexico). No additional data on the virus from which these partial sequences were derived are available. However, the relative low levels of nucleotide sequence identities (less than 90%) in the 3'-NTRs of both RNA1 and RNA2 (88.5% and 85.6% respectively), as well less then 90% aa identity (89%) in the largest putative CP (Vp36) between ToMarV and ToANV, suggests that the two viruses are not identical and may be strains or isolates of the same virus. Additional biological and molecular data on the virus from which the ToANV sequence was derived will be needed to determine its precise relationship to ToMarV.

Phylogenetic analysis based the aa region between the CG protease motif [Bazan J F, Fletterick R J (1988) Proc Natl Acad Sci USA 85: 7872-7876] and the GDD RdRp active site [Argos P (1988) Nucleic Acids Res 16: 9909-9916] in the RNA1-ORF were performed to determine the relationships between tomato marchitez virus, ToTV and other viruses from the genera Sadwavirus, Cheravirus and the families Sequiviridae, Comoviridae, Dicistroviridae and Picornaviridae. This region is proposed to be a good taxonomic predictor for classifying picorna-like viruses [Ikegami M, et al. (2002) Taxonomy of recognized and putative species in the family Comoviridae. XIIth IDMS Virology meeting Paris, France, 27 Jul.-12 Aug. 2002]. The resulting dendrogram (FIG. 13) shows that ToMarV virus clusters with ToTV and ToANV and confirms the separate taxonomic position of these viruses from the genus Cheravirus. A similar phylogenetic analysis on basis of the helicase region between the motifs A and C [Gorbalenya A E, Koonin E V, Wolf Y I (1990) FEBS Lett 262: 145-148](aa 397-494) confirms the taxonomic positions of ToMarV (FIG. 13). For this motif these viruses seem to be more closely related to the genera Waikavirus and Sequivirus.

Tomato marchitez virus (ToMarV) is a new picorna-like plant virus, related to, but distinct from, tomato torrado virus (ToTV). ToMarV and ToTV clearly separate from other plant picorna-like viruses but based on standard virological criteria, they belong to the same genus. ToTV is the tentative new type species of a novel genus of plant viruses: Torradovirus.

It should be understood that homologies may be large when two sequences are compared over a small comparison window since local regions of sequence similarity can often be found when two long nucleotide sequences are compared. However, the skilled person is aware that sequence homology requires the establishment of common motifs between the sequences, among which the sequence identity may locally be as high as 35 to 100%, but may be as low as 10-20% in other parts of the genomic sequence of the same ORF. Thus, when reference is made herein that a sequence has a nucleotide sequence homology of at least 50% to SEQ ID NO:1 or SEQ ID NO:2, this may refer to the sequence homology between regions amongst common motifs, where homology is greatest, but also between the coding sequence of two homologous proteins. Note that sequence homologies may differ between the various genes in the genome (see Examples).

As an indication of the relatedness between the newly identified ToTV virus isolate and other viruses (including viruses to be compared therewith) a phylogenetic analysis may normally be performed based on (part of the) the genomic sequence information of the viruses.

Several such analyses are presented in the Examples below. The information obtained thus far indicates that ToTV shows the highest level of homology with viruses from the genera Sequivirus and Waikavirus (Sequiviridae) and the genera Cheravirus and Sadwavirus. Viruses from these genera are distinguished on the basis of the number of viral RNAs—Sequiviridae have 1 RNA while Cheraviruses and Sadwaviruses have two RNAs and the number of capsid proteins—Sadwaviruses have two CPs, Cheraviruses have three CPs. These criteria suggest that Tomato torrado virus is most likely to group within the genus Cheravirus, However, phylogenetic analyses using several different motifs from the putative RdRp and helicase proteins, position ToTV clearly separate from the genera Cheravirus and Sadwavirus and in fact suggest that it is more closely related to the Sequiviridae. Unfortunately, full sequences from only one Cheravirus (CRLV) and two Sadwaviruses (SDV and SMoV) are currently available. Preliminary data on vector transmission suggest that ToTV might be transmitted by whiteflies while the natural vectors of CRLV and Sadwaviruses are unknown. On the basis of the presently available information, including sequence information as well as additional taxonomical information as presented in Table 1, below, the newly found virus is most likely a novel genus.

TABLE 1

Taxonomic descriptors for the newly discovered ToTV virus (as listed by the Internationally accepted methods from the handbook "Matthew's Plant Virology" ("Matthew's Plant Virology", Fourth Edition, Roger Hull (ed.) Academic Press, San Diego, p 15, Table 2.1 therein) (The numbering of the Table in Matthews' is adhered to in Table 1 below).

I Virion Properties
A. Morphological properties of virions
  1. 28 nm in size
  2. Spherical (icosahedral) in shape
  3. Envelop absent
B. Physical properties of the virions
  (not investigated)
C. Properties of the genome
  1. RNA type nucleic acid
  2. Single stranded RNA
  3. Linear RNA
  4. Positive sense coding
  5. At least 2 segments (RNA 2; SEQ ID NO: 1 and RNA 1; SEQ ID NO: 2)
  6. 5.5 kb (more precisely 5.2 kb or 5389 nucleotides excluding the poly(A)tail) and 8 kb (more precisely 7.7 kb or 7793 nucleotides excluding the poly(A)tail)
  7. 5' terminal cap unknown
  8. 5' terminalcovalently linked polypeptide unknown
  9. Poly(A) tract present at both segments
  10. Nucleotide sequence comparisons:
    RNA 1 contains an ORF1 with motifs typical of helicase (Hel), Protease and RNA-dependent RNA polymerase (RdRp). Level of homology with helicase and RdRp motifs of other viruses is described in detail in the Examples.
    RNA 2 contains two ORFs of which one has at its N-terminus a motif typical of putative movement protein (MP) and which contains at the C-terminus the sequences of the three capsid (coat) proteins (CP). The level of homology with capsid proteins of other viruses is described in detail in the Examples.

TABLE 1-continued

Taxonomic descriptors for the newly discovered ToTV virus (as listed by the Internationally accepted methods from the handbook "Matthew's Plant Virology" ("Matthew's Plant Virology", Fourth Edition, Roger Hull (ed.) Academic Press, San Diego, p 15, Table 2.1 therein) (The numbering of the Table in Matthews' is adhered to in Table 1 below).

D. Properties of the proteins
1. 3 × CP; Hel; RdRp; Protease; putative MP
2. CPs: 35, 26 and 23 kDa
3. (For functional activities, see above and Examples below)
4. (For amino acid sequence comparison see Examples below)

II. Genomic organization and replication
1. Genomic organization see FIG. 7
6. Cytopathology: At least the epidermis of mesophyl cells or accompanying cells of phloem III. Antigenic properties.
1. No known serological relationships IV. Biological properties
1a. Natural host range: Tomato;
1b. Experimental host range:

| Tested alternative host plants for ToTV | Local symptoms/ systemic symptoms |
|---|---|
| *Chenopodium quinoa* | —/— |
| *Gomphrena globosa* | —/— |
| *Nicotiana benthamiana* | —/c |
| *Nicotiana clevelandii* | —/c |
| *Nicotiana glutinosa* | —/c |
| *Nicotiana hesperis* 67A | nl/c, n, mf |
| *Nicotiana occidentalis* P1 | nl/c, n, mf |
| *Nicotiana rustica* | —/—(la) |
| *Nicotiana tabacum* 'White Burley' | —/—(la) |
| *Physalis floridana* | nl/c, n, mf, do |

2. Pathogenicity
Symptoms on natural host plant: Necrotic lesions finalizing in burn-like, full necrosis of plant material and death of the plant; concentric rings of necrotic spots on fruits.
Association with disease: Torrado; presumably also Chocolate spot; presumably also Marchitez
3. Tissue trophism: At least the epidermis of mesophyl cells or accompanying cells of phloem
4. Mode of transmission in nature unknown
5. Vector relationships: Presumably white fly
6. Geographical distribution: Mediterranean; America's (Central America, Mexico and Southern part of North America)

c = chlorosis;
n = necrosis;
l = lesions;
mf = malformation;
do = die off;
la = latent infection,
— = no symptoms.

It was recently found by the present inventors that genomic sequences of the associated virus of a tomato disease in Central America (e.g. Mexico and Guatemala) by the name of "Chocolate spot disease", "Chocolate" or "Marchitez" were identical to those of the herein described ToTV (see Example 2). Therefore, the causal agent associated with this disease is an aspect of the present invention.

As more viral sequences become available, both from non-ToTV viruses that may or may not be closely related thereto, or from viruses closely related to or essentially resembling the ToTV virus, phylogenetic analysis will prove a valuable way of determining the breadth of the taxon or Glade of ToTV based on phylogenetic relatedness between isolates.

Phylogenetic relatedness may for instance be determined based on any one or all of the nucleotide sequences of RNA 1 and/or RNA 2 of the viral genome or on capsid protein (gene) sequence data. Phylogenetic analyses are well known to the skilled person and may for instance comprise analysis by distance-based tree-reconstruction (e.g. neighbor joining), maximum likelihood or parsimony analysis methods by using such programs as ClustalX (Thompson et al., 1997), PAUP (Swofford, 2000) or PHYLIP (Felsenstein, 1989).

In order to perform an analysis of phylogenetic relatedness between a novel isolate, the sequence of ToTV as provided herein, and reference sequences from viral strains from, for instance, GenBank, EMBL, or DDBJ databases, genomic RNA from said novel isolate may be extracted directly from infected plants and genomic sequences may be amplified therefrom. Reverse transcription with PCR amplification methods (RT-PCR) may for instance be conducted using degenerate oligonucleotide primers, such primers being for instance capable of acting as amplification primer for amplification of nucleic acid sequences from the genomes of divergent ToTV isolates as well as from the genomes of closely related viral species. Preferably, but not necessarily full-length genomic amplification products may thus be obtained from reference strains (e.g. divergent isolates), test-strains (ToTV-suspected isolates) and closely related species. Preferably, specific genetic regions of interest are amplified for comparison. The amplification products (DNA) may then be sequenced by for instance direct double-stranded nucleotide sequencing using fluorescently labeled dideoxynucleotide terminators (Smith et al., 1986) with the degenerate oligonucleotide primers used for RT-PCR. Nucleotide sequence editing, analysis, optional prediction of amino acid sequences, and alignments may be conducted with software packages available, such as with the LaserGene sequence analysis package version 5 (DNASTAR, Inc., Madison, Wis.) and IntelliGenetics GeneWorks version 2.5.1 (IntelliGenetics, Mountain View, Calif.) software. Phylogenetic analyses may then be completed with phylogenetic analysis using for instance parsimony (PAUP) software with a neighbor-joining algorithm using absolute distances following a heuristic search and 1,000 bootstrap replicates, and a phylogenetic tree may be generated by parsimony analysis of the aligned contiguous nucleotide or amino acid sequences, whereby in such trees the numbers generally represent bootstrap confidence levels. Following 1,000 replications, a confidence level of above 60%, preferably above 70%, more preferably above 80%, 90%, 95% or 98%, within a phylogenetic tree, are to be considered sufficient proof of correct phylogenetic inference (placement of isolates in a certain Glade), provided that the tree is sufficiently branched whereby optionally branching may be improved by rooting to a suitably out-group species. In this way it can be determined which isolates are most closely related to the ToTV sequences as provided herein. Relatedness is generally expressed in terms of percentage sequence similarity, herein termed sequence homology.

Although phylogenetic analyses provide a convenient method of identifying a virus in case of sufficient nucleic acid homology, with known viruses several other possibly more straightforward albeit somewhat more coarse methods for identifying said virus or viral proteins or nucleic acids from said virus are herein also provided. As a rule of thumb, a ToTV virus can be identified by the percentages of homology of the viral proteins or nucleic acids to be identified in comparison with viral proteins or nucleic acids identified herein by sequence. It is generally known that virus species, especially RNA virus species, often constitute a quasi species wherein a cluster of said viruses displays heterogeneity among its members. Thus it is expected that each isolate may have a somewhat different percentage homology with the sequences of the isolate as provided herein. Therefore, other viral isolates that exhibit sufficient sequence homology to ToTV (e.g. more than 30%, 40%, 50%, 60%, 70%, 80%, 90%, 95%, 98%, or 99% sequence homology) are considered to belong to the same virus. The ToTV virus of the present invention is therefore a virus having at least 50 or 60% homology, preferably at least 70%, more preferably at least 80%, still more preferably at least 90%, still more preferably at least 95%, still more preferably at least 98%, and most preferably at least 99% homology to the protein or nucleic acid sequences provided herein and causes ToTV-induced disease-symptoms in Solanaceae, more particularly in *Solanum* and *Nicotiana*, which disease-symptoms may or may not be similar to those described herein. In Cucurbitaceae the virus appears not to cause visible symptoms although the virus is capable of propagation in the plants.

When one wishes to compare a separate virus isolate with the protein or nucleic acid sequences described herein, the invention provides an isolated virus (ToTV) identifiable as phylogenetically corresponding to ToTV by determining a protein or nucleic acid sequence of said separate virus isolate and determining that said protein or nucleic acid sequence has a percentage sequence homology of at least 60%, preferably at least 70%, more preferably at least 80%, still more preferably at least 90%, still more preferably at least 95%, still more preferably at least 98%, and most preferably at least 99% to the sequences as listed herein.

Viral isolates having individual proteins or nucleic acids with higher homology than these mentioned maximum values are considered as phylogenetically corresponding and thus taxonomically corresponding to ToTV virus, and generally the proteins will be encoded by a nucleic acid sequence structurally corresponding with a sequence listed herein. Herewith the invention provides a virus phylogenetically corresponding to the isolated virus of which the sequences are listed herein.

It should be noted that, similar to other viruses, a certain degree of variation can be expected to be found between ToTV-viruses isolated from different sources.

Also, the nucleotide or amino acid sequence of the ToTV virus or fragments thereof as provided herein for example show less than 95%, preferably less than 90%, more preferably less than 80%, more preferably less than 70% and most preferably less than 60% nucleotide sequence homology, or less than 95%, preferably less than 90%, more preferably less than 80%, more preferably less than 70% and most preferably less than 60% amino acid sequence homology with the respective nucleotide or amino acid sequence of any non-ToTV virus or closest relative.

Sequence divergence of ToTV strains around the world may be somewhat higher, in analogy with other plant viruses.

The invention provides an isolated virus (ToTV) identifiable as phylogenetically corresponding thereto by determining a nucleic acid sequence of a suitable fragment of the genome of said virus and testing it in phylogenetic analyses wherein maximum likelihood trees are generated using for instance 1000 bootstraps as described above and finding it to be phylogenetically more closely related to a virus isolate comprising the sequences of SEQ ID NO:1 or SEQ ID NO:2, as listed herein for ToTV than it is related to a virus isolate of a non-ToTV reference strain or closest relative.

Suitable nucleic acid genome fragments each useful for such phylogenetic analyses are for example any portion of nucleic acid sequences of the 5.5 kb or 8 kb RNA fragments (respectively termed herein RNA2 and RNA1) as described in the Example.

With the provision of the sequence information of this ToTV virus, the invention provides diagnostic means and methods to be employed in the detection of ToTV virus in a sample. Preferably, the detection of ToTV virus is performed with reagents that are most specific for ToTV virus. This by no means however excludes the possibility that less specific, but sufficiently cross-reactive reagents are used instead, for example because they are more easily available and sufficiently address the task at hand.

The invention for example provides a method for detecting the presence of ToTV in plants, preferably in tomato plants, more preferably in plants of *S. lycopersicum*. Said method may for instance comprise determining in said sample the presence of a ToTV virus or component thereof by reacting said sample with a ToTV specific nucleic acid or antibody according to the invention. Although contact-infection of an indicator plant is also a suitable method for detecting the presence of virus in a test plant.

The invention provides the partial nucleotide sequence of a novel isolated virus (herein also called ToTV virus) and ToTV virus-specific components or synthetic analogues thereof. Additional genomic sequences of the ToTV virus to those provided herein may be determined by sequencing methods known to the skilled person. Genomic sequence determination is well within reach of the skilled person now that the present invention provides the ToTV virus, as well as partial genomic sequences thereof. These methods comprise for instance those described in the Example below. In general such sequencing methods include the isolation of the viral genome nucleic acids by nucleic acid isolation procedures, and the determination of the nucleotide sequence of the isolated nucleic acid, for instance by dideoxy chain termination methods (Sanger et al., 1977) optionally preceded by reverse transcription of RNA into DNA.

The invention provides among others an isolated or recombinant nucleic acid or virus-specific functional fragment thereof obtainable from a virus according to the invention. The isolated or recombinant nucleic acids comprise the sequences as listed herein or sequences of homologues, which are able to hybridise with those under stringent conditions. In particular, the invention provides primers and/or probes suitable for identifying a ToTV virus nucleic acid. Additional probes and primers capable of hybridising to a nucleic acid sequence of the ToTV virus may be developed by methods known to the skilled person.

Expression Vectors and Expression of Viral Encoding Genes

Furthermore, the invention relates to an expression vector comprising a nucleic acid according to the invention. To begin with, expression vectors such as plasmid vectors containing (parts of) a double stranded sequence of the ToTV viral genome, viral vectors containing (parts of) the genome of ToTV (for example, but not limited to vaccinia virus, retroviruses, baculovirus), or ToTV virus containing (parts of) the genome of other viruses or other pathogens are part of the present invention.

The expression vector may comprise a ToTV genomic sequence or part thereof that is under control of or operatively linked to a regulatory element, such as a promoter. The segment of DNA referred to as the promoter is responsible for the regulation of the transcription of DNA into mRNA. The expression vector may comprise one or more promoters suitable for the expression of the gene, preferably for the expression of viral protein-encoding gene, in plant cells, fungal cells, bacterial cells, yeast cells, insect cells or other eukaryotic cells. Expression vectors of the invention are very useful to provide antigens of the virus in gene expression systems.

Also, the invention pertains to a host cell comprising a nucleic acid or an expression vector according to the invention. Plasmid or viral vectors containing the nucleic acids encoding protein components of ToTV virus may be generated in prokaryotic cells for the expression of the components in relevant cell types (plant cells, fungal cells, bacteria, insect cells, plant cells or other eukaryotic cells). Plasmid or viral vectors containing full-length or partial copies of the ToTV virus genome may be generated in prokaryotic cells for the expression of viral nucleic acids in vitro or in vivo.

Methods for Isolation and Purification of ToTV

The ToTV virus may be isolated from infected plants or other sources by any method available. Isolation may comprise purifying or partially purifying ToTV viral particles from a suitable source. A wide range of methods is available for virus isolation and purification (for instance, see Dijkstra and De Jager, 1998). Purification of ToTV may for instance be performed by using standard procedures for e.g. nepoviruses or luteoviruses (with the aid of organic solvents) (see e.g. Walker, 2004). Although such protocols may result in loss of infectivity of the virus, these procedures may still be useful to obtain virus material for other purposes.

Preferably, in order to maintain viral integrity, a mild purification method is used to purify ToTV. Such a mild purification method may for instance comprise homogenizing infected material of a plant (such as leaves) in a homogenization buffer (comprising for instance 0.1 M TRIS-HCl buffer at a pH of about 8, about 20 mM of sodium sulphite [$Na_2SO_3$], about 10 mM of sodium diethyldithiocarbamate [Na-DIECA] and about 5 mM of sodium ethylenediaminetetraacetate (Na-EDTA)), separating the debris by centrifugation (for instance for 30 min. at 49,000 g), placing the supernatant on a suitable sucrose cushion (e.g. 20%) and pelleting the viral particles (for instance by centrifuging for 1.5 h at 70,000 g). Thereafter, the pellet comprising the viral particles may be resuspended in a suitable buffer (e.g. in TRIS-HCl, pH 8), and the virus-containing fraction may be separated from the remainder of the suspension by using density centrifugation in a sucrose gradient (e.g. 10-40% sucrose in homogenization buffer centrifuged for 2 h at 110,000 g). The virus-containing fraction may be determined by using infection experiments. Further purification may occur by using density centrifugation in a cesium sulfate gradient (e.g. 10-40% cesium sulfate gradient in TRIS-HCl, pH 8, centrifuged for 16 h at 125,000 g). Enriched viral bands may then be collected from the gradient and further concentrated by centrifugation or dialysis (e.g. against 0.1 M TRIS-HCl, pH 8).

Infectivity of ToTV after purification may be checked by inoculation onto a sensitive plant (e.g. *N. hesperis* '67A').

Methods for Purification of ToTV Associated Proteins and Amino Acid Sequencing Having prepared purified or partially purified ToTV virus it is possible to prepare a substantially pure preparation of a viral-associated protein (e.g. virus-encoded proteins). Although numerous methods and strategies for protein purification are known in the art it will be most convenient to purify ToTV viral proteins, such as viral coat proteins, by either electrophoresis using for instance a sodium dodecylsulphate-polyacrylamide gel (SDS-PAGE) or by affinity chromatography. Each of these methods will be described below.

Proteins of interest of ToTV may be separated by electrophoresis using for instance Tricine-SDS-PAGE (Schagger and Von Jagow, 1987) or Glycine-SDS-PAGE (Laemmli, 1970). Other electrophoresis systems that are capable of resolving the various proteins comprised in the virus isolate, or transcribed from its genome and expressed in a suitable expression system, may of course also be employed, such as non-denaturing gel electrophoresis. The area of the PAGE gel including the target protein may be excised and the target polypeptides may be eluted therefrom, for instance by using an Elutrap® device (Schleicher & Schuell, Dassel, Germany). A target protein may be identified by its mobility relative to reference polypeptides in a gel. To increase purity the eluted protein may be run on a second SDS-PAGE gel and eluted a second time. The protein or peptide contained in the excised gel fragment may then be eluted again and is suitable for use in immunization or in protein sequencing.

Proteins of interest of ToTV may also be purified by affinity chromatography using an antibody (such as a monoclonal antibody) that specifically binds to a ToTV protein. The antibody may be covalently coupled to solid supports such as celluloses, polystyrene, polyacrylamide, cross-linked dextran, beaded agarose or controlled pore glass using bifunctional coupling agents that react with functional groups on the support and functional groups (i.e., reactive amino acid side chains) on the antibody molecule. Such methods are readily available to the skilled person. The resulting antibody-bearing solid phase is contacted with purified or partially purified virus under reducing conditions using pH, ionic strength, temperature and residence times that permit the protein of interest to bind to the immobilized antibody. The virus or protein is eluted from the column by passing an eluent that dissociates hydrogen bonds through the bed. Buffers at specific pH or NaCl solutions above about 2 M are commonly used eluents.

Methods for carrying out affinity chromatography using antibodies as well as other methods for immunoaffinity purification of proteins (such as viral capsid proteins) are well known in the art (see e.g., Harlow and Lane, 1988).

With the teachings provided herein, the skilled person is capable of isolating a virus-specific protein of ToTV, determining the amino acid sequence of for instance the N-terminal part of said protein, designing a set of degenerate probes (for the degeneracy of the genetic code) to hybridise with the DNA coding for a region of said protein, using these probes on an array of genes in a genomic library produced from the virus, obtaining positive hybridisations and locating the corresponding genes. The skilled person is then capable of identifying the structural region of the gene and optionally upstream and downstream sequences thereof. Thereafter the skilled person is capable of establishing the correct sequence of the amino acid residues that form the protein.

Antibody Production

Antibodies, either monoclonal or polyclonal, can be generated to a purified or partially purified protein or peptide fragment of the ToTV virus in a variety of ways known to those skilled in the art including injection of the protein as an antigen in animals, by hybridoma fusion, and by recombinant methods involving bacteria or phage systems (see Marks et al., 1992a; Marks et al., 1992b; Lowman et al., 1991; Lerner et al., 1992, each of which reference discloses suitable methods).

Antibodies against viral particles, proteins or peptides of the virus may be produced by immunizing an appropriate vertebrate, preferably mammalian host, e.g., rabbits, goats, rats, chicken and mice with the particles, proteins or peptides alone or in conjunction with an adjuvant. Usually two or more immunizations will be involved, and the blood or spleen will be harvested a few days after the last injection. For polyclonal antisera, the immunoglobulins may be precipitated, isolated and (affinity) purified. For monoclonal antibodies, the splenocytes will normally be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing (monoclonal) antibodies and methods for their preparation and use in various procedures are well known in the literature (see e.g. U.S. Pat. Nos. 4,381,292, 4,451,570, and 4,618,577; Harlow and Lane, 1988; Ausubel, et al., 1998; Rose et al., 1997; Coligan et al., 1997). Typically, an antibody directed against a virus-associated protein will have a binding affinity of at least $1\times10^5$-$1\times10^7$ $M^{-1}$.

A recombinant protein derived from the ToTV virus, such as may be obtained by expressing a protein-encoding genomic sequence of the virus in a suitable expression system, is preferred as the antigen. However, purified proteins may also be used. Antigens suitable for antibody detection include any ToTV protein that combines with any ToTV-specific antibody of a mammal exposed to or infected with ToTV virus. Preferred antigens of the invention include those that bring about the immune response in mammals exposed to ToTV, which therefore, typically are recognised most readily by antibodies of a mammal Particularly preferred antigens include the capsid proteins of ToTV. Structural proteins from purified virus are the most preferred.

Methods for cloning genomic sequences, for manipulating the genomic sequences to and from expression vectors, and for expressing the protein encoded by the genomic sequence in a heterologous host are well-known, and these techniques can be used to provide the expression vectors, host cells, and the cloned genomic sequences encoding antigens, which sequences are to be expressed in a host to produce antibodies for use in diagnostic assays (see for instance Sambrook et al., 2001 and Ausubel, et al., 1998).

A variety of expression systems may be used to produce ToTV antigens. For instance, a variety of expression vectors suitable to produce proteins in *E. coli, B. subtilis*, yeast, insect cells, plant cells and mammalian cells have been described, any of which might be used to produce a ToTV antigen suitable to produce an anti-ToTV antibody or fragment thereof. Of course ToTV itself may also be used as an expression vector for this purpose.

One use of antibodies of the invention is to screen cDNA expression libraries for identifying clones containing cDNA inserts that encode proteins of interest or structurally-related, immuno-cross-reactive proteins. Such screening of cDNA expression libraries is well known in the art (see e.g. Young and Davis, 1983), to which reference is made in this context, as well as other published sources. Another use of these antibodies is for use in affinity chromatography for purification of ToTV proteins. These antibodies are also useful for assaying for ToTV infection.

The present invention thus provides a ToTV-specific viral protein or a fragment thereof hereinafter termed proteinaceous molecule. Useful proteinaceous molecules are for example derived from any of the genomic sequences or fragments thereof derivable from a virus according to the invention. Such proteinaceous molecules, or antigenic fragments thereof, as provided herein, are for example useful in diagnostic methods or kits and in diagnostic compositions. Particularly useful are those proteinaceous molecules that are encoded by recombinant nucleic acid fragments that are identified for eliciting ToTV virus specific antibodies, whether in vivo (e.g. for providing diagnostic antibodies) or in vitro (e.g. by phage display technology or another technique useful for generating synthetic antibodies or parts thereof).

Also provided herein are antibodies, be it natural polyclonal or monoclonal, or synthetic antibodies (e.g. (phage) library-derived binding molecules) that specifically react with an antigen comprising a proteinaceous molecule or ToTV virus-specific functional fragment thereof, such as a capsid protein according to the invention.

Methods for Identifying a Viral Isolate as a ToTV Virus

Apart from the detection of ToTV virus, which involves diagnostic methods, the present invention also relates to methods for identification, i.e. confirmation that the isolate is ToTV. Such methods may be based on phylogenetic inference as described above, and determining the level of nucleotide or amino acid sequence homology between an unidentified viral isolate and one or more reference strains of confirmed ToTV virus and non-ToTV virus. Such methods may for instance comprise sequencing (part of) the genome of a viral isolate or of a capsid protein and comparing the level of homology of that sequence to the sequences as provided herein for ToTV. An isolate having more than 50% sequence homology with SEQ ID NO:1 or SEQ ID NO:2 as provided herein is considered taxonomically corresponding to ToTV or belonging to the ToTV viral taxon. Such a virus is part of the present invention.

In order to identify a virus as a Tomato torrado virus (ToTV), one may also make use of the taxonomic descriptors as presented in Table 1 above, and find by comparison that a new isolate belongs to the presumptive novel genus, of which the ToTV strain identified by the nucleic acid sequences of SEQ ID NOs: 1 and 2 provided herein, and deposited with the Deutsche Sammlung von Mikroorganismen and Zellkulturen GmbH on 24 Nov. 2004 under depositors reference number ToTV-E01 (DSM 16999) may be assigned as the type species. Thus, it is not essential that a sequence comparison is performed in order to assess that a virus is ToTV. Rather, a method of identifying a virus as a Tomato torrado virus (ToTV) may comprise the steps of assessing the presence of the combination of taxonomic descriptors selected from the group consisting of a) morphological descriptors, such as spherical, non-enveloped virion particles of approximately 28 nm in diameter;
b) genome properties descriptors, such as having single stranded linear positive sense RNA virus properties based on two RNA segments that comprise poly(A)-tails, that encode polyproteins of 5.5 and 8 kDa, respectively, and that comprise coding regions or motifs for 3 capsid proteins, helicase, protease, RdRP and putative movement protein and which RNA segments and/or polyproteins and/or motifs have homologies based on sequence comparison essentially as described herein, and
c) biological properties descriptors, such as producing the necrotic lesions and burn-like symptoms in tomato, having a host range, vector relationship and/or geographical distribution essentially as described herein, and being associated with the diseases of tomato plants locally known under such names as torrado, marchitez and/or chocolate spot.

The combination of taxonomic descriptors that results in a positive identification of a virus isolate as being a Tomato torrado virus (ToTV) is that combination which shows the isolate as being more closely related (based on numerically taxonomic methods well known to the skilled artisan) to ToTV as described herein, than to other viruses, and wherein said isolate preferably produces the disease symptoms in tomato typical of torrado as described herein.

Thus, a virus which, based on numerical taxonomic analysis of taxonomic descriptors essentially as defined in Table 1, shows to be more closely related to the virus as defined in claim 1 herein than to any other virus known at the time of filing of the present application, and which virus is associated with a disease that causes necrotic lesions in tomato, is considered herein to be a ToTV and falls within the scope of the present invention.

In this way the invention provides a viral isolate identifiable with a method according to the invention as a plant virus taxonomically corresponding to a virus identifiable as likely belonging to the ToTV viral taxon. Depending upon the phylogenetic relatedness, or distinctness with other viral taxa, the ToTV viral taxon may be an isolate, a species, a genus or even a family of virus.

Alternatively, methods for identifying a viral isolate as a ToTV virus may be based on symptomatology, i.e. recognition of the virus by its disease-symptoms.

However, in a preferred embodiment, antibodies of the invention are used in a method for identifying a viral isolate as a ToTV virus, provided cross-reactivity of such antibodies with related non-ToTV strains has been effectively ruled out. Such methods comprise the step of reacting said viral isolate or a component thereof with an antibody as provided herein. Reacting is herein referred to as allowing the occurrence of antibody-antigen bonding. This can for example be achieved by using purified or non-purified ToTV virus or parts thereof (proteins, peptides). Preferably, infected cells or cell cultures are used to identify viral antigens using any suitable immunological method. Specifically useful in this respect are antibodies raised against ToTV viral capsid proteins.

Other preferred methods for identifying a viral isolate as a ToTV virus comprise reacting said viral isolate or a component thereof with a virus specific polynucleotide according to the invention, which polynucleotide is capable of hybridizing under stringent conditions to a nucleic acid sequence selected from the group consisting of SEQ ID NO:1, SEQ ID NO:2, sequences having a nucleotide sequence homology of at least 60% to SEQ ID NO:1 or SEQ ID NO:2, and their complementary strands and ToTV-specific fragments thereof. Such a hybridization reaction may be performed in any format available to the skilled person and will generally involve tissue printing, dot blot methods, Southern/Northern blotting or hybridization, in situ hybridization, PCR, RT-PCR and the like.

Immunological Detection Methods

Methods of the invention in which antigens are detected can in principle be performed by using any immunological method, such as for instance classical immunofluorescence (IF), immunohistochemical techniques or comparable antigen detection assay formats. Preferred ToTV detection methods based on detection of the viral coat protein may for instance comprise such methods as precipitation and agglutination tests, radio-immunoassay (RIA), immunogold labeling, immunosorbent electron microscopy (ISEM), enzyme-linked immunosorbent assay (ELISA), Western blotting and immunoblotting. Examples of types of immunoassays that can utilize antibodies of the invention are competitive and non-competitive immunoassays in either a direct or indirect format. Antibodies can be utilized in immunoassays in the liquid phase or bound to a solid phase carrier. In addition, the antibodies in these immunoassays can be detectably labeled in various ways. Those skilled in the art will know, or can readily discern, suitable immunoassay formats without undue experimentation. Assay formats are well known in the literature and are described, for example, in Harlow and Lane (1988).

A variety of immunoassay formats may be used to select antibodies specifically reactive with a particular polypeptide according to the invention, such as ToTV viral coat proteins. For example, solid-phase ELISA immunoassays are routinely used for this purpose. See Harlow and Lane (1988), for a description of immunoassay formats and conditions that can be used to determine selective binding.

Antibodies can be bound to many different carriers and used to detect the presence of the target molecules. Alternatively, antigens may be bound to many different carriers and used to detect the presence of the antibody. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such using routine experimentation.

Western blot assays are described generally in Harlow and Lane (1988). According to this method the viral proteins (and other proteins in the virus preparation) are separated by gel electrophoresis and transferred to a solid phase (i.e., a membrane such as nitrocellulose). The immobilized antigen is subsequently reacted with an antibody and detection system (e.g., an alkaline phosphatase-conjugated second antibody). As will be apparent to those of skill, it will be advantageous to include appropriate negative and positive control materials (such as substantially purified antigen or ToTV virus) in the assay.

Enzyme-Linked Immuno-Sorbent Assays (ELISA) are described generally in Harlow and Lane (1988). The assay involves the reaction of a viral component (e.g., a capsid protein) with an antibody. In one embodiment the sample may comprise a plant tissue which is ground and reacted to the antibody that has been coated onto a solid phase such as a test plate. If the virus is present in the sample, an enzyme-labeled specific antibody will bind to the antibody-virus complex, and it will be detected by an enzyme substrate reaction that produces a color reaction. Preferred methods of ELISA analysis are direct double antibody sandwich (DAS) ELISA (Clark and Adams, 1977), DAS indirect ELISA (Vela et al. 1986), or TAS-ELISA. It will be apparent to those skilled in the art that in an ELISA or any other type of assay it will sometimes be desirable to determine the presence of more than one viral capsid protein in a single reaction, for example by mixing two or more antibodies with different specificities and assaying for either or all of the protective capsid-associated proteins of the invention.

Nucleic Acid Based Detection Methods

ToTV is composed of at least two ribonucleic acids (RNAs). There are strong indications for the presence of three protective capsid proteins. The methods described above are focused on immunological detection of viral proteins for the detection of the virus. By recombinant DNA technology it is possible to produce probes that directly or indirectly hybridize to the viral RNAs (or their complement), or cDNA produced therefrom by reverse transcription, and which can be used in assays for the detection of the virus. Nucleic acid amplification techniques allow the amplification of fragments of viral nucleic acids, which may be present in very low amounts.

In order to develop nucleic acid-based detection methods, virus-specific sequences must be determined for which primers or probes may then be developed. To detect ToTV by nucleic acid amplification and/or probe hybridization, the capsid protein of ToTV may be sequenced or, alternatively, the viral genomic RNA may be isolated from purified virus, reverse transcribed into cDNA and directly cloned and/or sequenced. Using either the cloned nucleic acid as a hybridization probe, using sequence information derived from the clone, or by designing degenerative primers based on the amino acid sequence of the ToTV protein, nucleic acid hybridization probes and/or nucleic acid amplification primers may be designed an used in a detection assay for detecting the presence of the virus in a sample as defined herein.

Methods of the invention in which nucleic acids are detected can in principle be performed by using any nucleic acid amplification method, such as the Polymerase Chain Reaction (PCR; Mullis and Faloona, 1987; U.S. Pat. Nos. 4,683,195; 4,683,202; and 4,800,159) or by using amplification reactions such as Ligase Chain Reaction (LCR; Barany, 1991; EP 0 320 308), Self-Sustained Sequence Replication (35R; Guatelli et al., 1990), Strand Displacement Amplification (SDA; Walker et al., 1992; U.S. Pat. Nos. 5,270,184 and 5,455,166), Transcriptional Amplification System (TAS; Kwoh et al., 1989), Q-Beta Replicase (Lizardi et al., 1988), Rolling Circle Amplification (RCA; U.S. Pat. No. 5,871,921), Nucleic Acid Sequence Based Amplification (NASBA; Compton, 1991), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of nucleic acids.

Since the virus is an RNA virus (i.e. the sequences of FIGS. 5 and 6 are the DNA equivalent of the viral RNA genome), a suitable detection method may comprise isolating the viral nucleic acids from a sample, for instance from an infected plant, by using methods known per se to the skilled person (e.g. Chomczynski and Sacchi, 1987; Boom et al., 1990) or commercially available systems (e.g. the RNeasy total RNA isolation kit or RNeasy plant RNA isolation kit from QIAGEN GmbH, Hilden, Germany, or the High-Pure-RNA-Isolation-Kit® (Roche Diagnostics, a division of F. Hoffmann-La Roche Ltd, Basel, Switzerland).

Total RNA may for instance be extracted from leaf material or protoplasts of plant cells and the total RNA, or specifically the viral genomic RNA, or a part thereof, may then be reverse transcribed into cDNA by using for instance an Avian myeloblastosis virus (AMV) reverse transcriptase or Moloney murine leukemia virus (M-MuLV) reverse transcriptase. A suitable method may for instance include mixing into a suitable aqueous buffering system (e.g. a commercially available RT buffer) a suitable amount of total RNAs (e.g. 1 to 5 μg), a suitable amount (e.g. 10 pmol) of a reverse transcription primer, a suitable amount of dNTPs and the reverse transcriptase, denaturing the nucleic acids by boiling for 1 min, and chilling them on ice, followed by reverse transcription at for instance 45° C. for 1 h as recommended for the specific reverse transcriptase used, to obtain cDNA copies of the viral sequences.

As a reverse transcription primer a polynucleotide according to the present invention may be used, for instance an 18-25-mer oligonucleotide comprising a nucleotide sequence complementary to the ToTV genomic sequence or preferably at least capable of hybridizing under stringent conditions to the nucleic acid sequence of SEQ ID NO:1 or SEQ ID NO:2, or a ToTV-specific fragment thereof. Alternatively, an a-specific polyT primer (oligo dT primer) may be used in order to start reverse transcription from polyA RNA motifs.

Following the RT-step, the cDNA obtained may be PCR amplified by using for instance Pfu and Taq DNA polymerases and amplification primers specific for the viral genomic cDNA sequences. Also complete commercially available systems may be used for RT-PCR (e.g. the Access and AccessQuick™ RT-PCR Systems of Promega [Madison Wis., USA], or the Titan™ One Tube RT-PCR System or two-step RT-PCR systems provided by Roche Diagnostics [a division of F. Hoffmann-La Roche Ltd, Basel, Switzerland]).

In order to amplify a nucleic acid with a small number of mismatches to one or more of the amplification primers, an amplification reaction may be performed under conditions of reduced stringency (e.g. a PCR amplification using an annealing temperature of 38° C., or the presence of 3.5 mM $MgCl_2$). The person skilled in the art will be able to select conditions of suitable stringency.

The primers herein are selected to be "substantially" complementary (i.e. at least 65%, more preferably at least 80% perfectly complementary) to their target regions present on the different strands of each specific sequence to be amplified. It is possible to use primer sequences containing e.g. inositol residues or ambiguous bases or even primers that contain one or more mismatches when compared to the target sequence. In general, sequences that exhibit at least 65%, more preferably at least 80% homology with the target DNA or RNA oligonucleotide sequences, are considered suitable for use in a method of the present invention. Sequence mismatches are also not critical when using low stringency hybridization conditions.

The detection of the amplification products can in principle be accomplished by any suitable method known in the art. The amplified fragments may be directly stained or labelled with radioactive labels, antibodies, luminescent dyes, fluorescent dyes, or enzyme reagents. Direct DNA stains include for example intercalating dyes such as acridine orange, ethidium bromide, ethidium monoazide or Hoechst dyes.

Alternatively, the DNA or RNA fragments may be detected by incorporation of labelled dNTP bases into the synthesized fragments. Detection labels which may be associated with nucleotide bases include e.g. fluorescein, cyanine dye, digoxigenin (DIG) or bromodeoxyuridine (BrdUrd).

When using a probe-based detection system, a suitable detection procedure for use in the present invention may for example comprise an enzyme immunoassay (EIA) format (Jacobs et al., 1997). For performing a detection by manner of the EIA procedure, either the forward or the reverse primer used in the amplification reaction may comprise a capturing group, such as a biotin group for immobilization of target DNA PCR amplicons on e.g. a streptavidin coated microtiter plate wells or streptavidin coated Dynabeads® (Dynal Biotech, Oslo, Norway) for subsequent EIA detection of target DNA-amplicons. The skilled person will understand that other groups for immobilization of target DNA PCR amplicons in an EIA format may be employed.

Probes useful for the detection of the target nucleic acid sequences as disclosed herein preferably bind only to at least a part of the nucleic acid sequence region as amplified by the nucleic acid amplification procedure. Those of skill in the art can prepare suitable probes for detection based on the nucleotide sequence of the target nucleic acid without undue experimentation as set out herein. Also the complementary nucleotide sequences, whether DNA or RNA or chemically synthesized analogues, of the target nucleic acid may suitably be used as type-specific detection probes in a method of the invention, provided that such a complementary strand is amplified in the amplification reaction employed.

Suitable detection procedures for use herein may for example comprise immobilization of the amplicons and probing the nucleic acid sequences thereof by e.g. Northern and Southern blotting. Other formats may comprise an EIA format as described above. To facilitate the detection of binding, the specific amplicon detection probes may comprise a label moiety such as a fluorophore, a chromophore, an enzyme or a radio-label, so as to facilitate monitoring of binding of the probes to the reaction product of the amplification reaction. Such labels are well known to those skilled in the art and include, for example, fluorescein isothiocyanate (FITC), β-galactosidase, horseradish peroxidase, streptavidin, biotin, digoxigenin, $^{35}S$, $^{14}C$, $^{32}P$ or $^{125}I$. Other examples will be apparent to those skilled in the art.

Detection may also be performed by a so called reverse line blot (RLB) assay, such as for instance described by Van den Brule et al. (2002). For this purpose RLB probes are preferably synthesized with a 5' amino group for subsequent immobilization on e.g. carboxyl-coated nylon membranes. The advantage of an RLB format is the ease of the system and its speed, thus allowing for high throughput sample processing.

The use of nucleic acid probes for the detection of RNA or DNA fragments is well known in the art. Mostly these procedures comprise the hybridization of the target nucleic acid with the probe followed by post-hybridization washings. Specificity is typically the function of post-hybridization washes, the critical factors being the ionic strength and temperature of the final wash solution. For nucleic acid hybrids, the Tm can be approximated from the equation of Meinkoth and Wahl (1984): Tm=81.5° C.+16.6 (log M)+0.41 (% GC)−0.61 (% form)−500/L; where M is the molarity of monovalent cations, % GC is the percentage of guanosine and cytosine nucleotides in the nucleic acid, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, the hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, 1993; Ausubel et al., 1998.

In another aspect, the invention provides oligonucleotide probes for the detection of ToTV RNA or cDNA. The detection probes herein are selected to be "substantially" complementary to a single stranded RNA molecule, or to one of the strands of the double stranded nucleic acids generated by an amplification reaction of the invention. Preferably the probes are substantially complementary to the, optionally immobilized (e.g. biotin labelled) antisense strands of the amplicons generated from the target RNA or DNA.

It is allowable for detection probes of the present invention to contain one or more mismatches to their target sequence. In general, sequences that exhibit at least 65%, more preferably at least 80% homology with the target oligonucleotide sequences are considered suitable for use in a method of the present invention.

ToTV Resistant Plants

The invention further relates to a method for identifying a ToTV-resistant plant, or part thereof. There are various possibilities of identifying ToTV-resistant plants. In a first set of embodiments of such a method, active/infectious virus or full-length infectious clones may be used, whereas in an alternative embodiment only virus-detection means are used.

A first step of a method for identifying a ToTV-resistant plant using active/infectious virus comprises exposing a plant or plant part, such as a leaf or stem segment, to a infective dosage of ToTV, the aim of which is to achieve an infection. The exposure may in many cases involve the establishment of physical contact. An infective dosage may vary between plants and between ToTV-isolates tested. Theoretically, an amount of about 1 to 10 to an amount of about 500-5000 viral particles of said virus or the nucleic acids thereof will be sufficient. Infection in this way may be achieved by mechanical inoculation of purified virus particles or virus nucleic acid on healthy plants.

Alternatively, infection may be achieved by, for instance:

growing a healthy scion on a ToTV-infected rootstock, or vice versa;

exposing a healthy plant to transmission vectors containing the virus (including infected plants, e.g. parasitic plants like *Cuscuta* spp.);

introducing into a healthy plant an expression vector harbouring a coding region of the ToTV virus genome;

the use of agro-infectious clones, such as *Agrobacterium tumefaciens* strains containing an expression vector harbouring a coding region of the ToTV virus genome.

In the context of the present invention, methods for exposing a plant or plant part to an infective dosage of ToTV are not limited to any particular method.

As stated, infection may comprise mechanical inoculation of the virus on healthy plants. For instance, a portion of a diseased leaf may be rubbed directly onto a leaf of a plant that is to be infected. In an alternative procedure, an inoculum may for instance be prepared by grinding virus-containing plant tissue, preferably young leaves showing symptoms, with a mortar and pestle, or any other suitable type of homogeniser, in for instance a buffer suitable for inoculation (e.g. a 0.03 M phosphate buffer, pH 7.7). After grinding, the obtained homogenate (the sap) is preferably filtered, e.g. through cheese cloth. The sap may then be inoculation, for instance by gently contacting leaves with an amount of the sap. The leaves are preferably pre-treated in order to damage the lower epidermis and enhance entry of the virus. This may for instance be achieved by pre-dusting the leaves with carborundum powder. Excessive wounding is preferably avoided. Preferably a carborundum powder is used having microscopically small angular particles of silicon carbide (400-500 mesh). Carborundum powder may also be added directly to the sap, in which case the pre-treatment is omitted. The sap may, for instance, be applied by the forefinger, a pad of sap-soaked foam or fabric, or even with the pestle used for grinding, a glass spatula, a stiff brush, or a spray gun. After inoculation, the leaves are preferably immediately washed with water.

A second step of a method for identifying a ToTV-resistant plant comprises identifying said plant as a ToTV-resistant plant when, after said exposure, either i) disease-symptoms in said plant or plant part remain absent or are delayed in expression or are at least reduced in severity or are localized relative to a susceptible and/or sensitive control plant, and/or ii) ToTV virus or ToTV genomic sequences are not present in said plant or plant part or the presence of ToTV virus is at least quantitatively reduced in said plant relative to a susceptible control plant. As used herein the term localized means limited to the inoculated leaf.

Determining the development of ToTV-induced disease-symptoms in infected plants may be performed by quantitative methods, e.g. wherein the period required for the development of discernible (e.g. visible) disease-symptoms is noted, or by qualitative methods wherein, after a certain period has lapsed, the plant is inspected for symptom expression and the presence or severity of the symptoms is indicated.

In addition to determining the development of ToTV-induced disease-symptoms or as an alternative thereto, depending on the type of ToTV-resistance to be detected, the presence of the virus is detected in the plant or plant part. In order to detect the absence of virus in the test plants, any method may in principle be used. For instance, a method may be employed wherein a ToTV specific antibody, primer-set or probe according to the present invention is used. Alternatively, a portion of the test plant may be brought into contact with a susceptible indicator plant (e.g. *N. hesperis* '67A') to establish whether virus is present or absent in the test plant. The skilled person will understand that for such methods it is important to decontaminate the surface of the test plant, in order to distinguish between a transmission vector, a tolerant test-plant and a resistant test plant, since only the presence of virus in the plant cells needs to be established.

In performing the second step of a method for identifying a ToTV-resistant plant, the following results may be obtained. If, after successful inoculation (e.g. after the establishment of a plant-virus contact under conditions that would result in infection in a susceptible and sensitive control plant):

i) disease-symptoms remain absent; or viral particles, or viral RNA cannot be detected: the plant is resistant;
ii) disease-symptoms are delayed or reduced in severity; or systemic low titres of viral particles or viral RNA can be detected: the plant is partially resistant;
iii) disease-symptoms are severe, but remain local, limited to the inoculated leaf and do not systemically spread beyond inoculated tissue; or viral particles, or viral RNA can only be detected locally: the plant is hypersensitive;
iv) if disease-symptoms remain absent; and viral particles, or viral RNA can be detected: the plant is tolerant.
v) if the plant develops disease-symptoms and has high systemic virus titres, then the plant is susceptible and sensitive. Examples of such plants are the plants from which the virus of the present invention was isolated. These plants may serve as suitable control plants in methods of the present invention.

For the purpose of producing resistant plants, and from a viewpoint of phytosanitation, only outcome i), ii) and iii) may be considered of interest. For the purpose of obtaining plants suitable for the production of symptomless crops and products, outcome iv) may also be of particular commercial interest.

In an alternative embodiment of a method for identifying a ToTV-resistant plant only virus-detection means are used. For instance, a ToTV-resistant plant may be identified in the field by observing or identifying a symptomless plant among symptomatic plants and determining the absence of virus in said plant by performing any of the virus detection methods according to the present invention. In fact, this corresponds to a method for identifying a ToTV-resistant plant wherein step a) of exposing a plant or plant part to a infective dosage of ToTV, is performed passively (e.g. naturally). When such a method is performed it is preferred that a method for detecting the presence of ToTV in a sample according to the present invention is used wherein the presence of a ToTV virus or component thereof is performed by reacting said sample with a polynucleotide or an antibody according to the present invention. Preferably, a method of identifying a ToTV-resistant plant requires the use of either the virus of the present invention or a polynucleotide or antibody according to the present invention.

The invention further relates to a method of producing a ToTV-resistant plant, or part thereof. Once a ToTV-resistant plant has been identified, this plant may serve as a donor plant of genetic material which is to be transferred from said donor plant to a recipient plant in order to provide said recipient plant with the genetic material. Transfer of genetic material from a donor plant to a recipient plant may occur by any suitable method known in the art. The genetic material will in most cases be genomic material. It is important however, that at least the resistance-conferring parts of the donor plant's genome are transferred. In the absence of methods for determining which parts of the donor plant's genome confer the ToTV resistance, the transfer may suitably occur by transferring complete chromosomes. Preferably, the ToTV-resistant plant serves as a male or female parent plant in a cross for producing resistant offspring plants, the offspring plant thereby receiving genomic material from the resistant donor and acting as the recipient plant. Although a susceptible parent in crosses is sensu stricto not necessarily a recipient plant, such a susceptible parent will herein also be included in the term recipient plant.

In a method for producing a ToTV-resistant plant, protoplast fusion can also be used for the transfer of resistance-conferring genomic material from a donor plant to a recipient plant, i.e. as a manner of crossing said plants. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbred in nature, is tissue cultured into a hybrid plant exhibiting the desirable combination of traits. More specifically, a first protoplast can be obtained from a tomato plant or other plant line that exhibits resistance to infection by ToTV. For example, a protoplast from a ToTV-resistant (tomato, eggplant, pepper, melon, watermelon or cucumber) line may be used. A second protoplast can be obtained from a susceptible second plant line, optionally from another plant species or variety, preferably from the same plant species or variety, that comprises commercially desirable characteristics, such as, but not limited to disease resistance, insect resistance, valuable fruit characteristics, etc. The protoplasts are then fused using traditional protoplast fusion procedures, which are known in the art to produce the cross.

Alternatively, embryo rescue may be employed in the transfer of resistance-conferring genomic material from a donor plant to a recipient plant i.e. as a manner of crossing said plants. Embryo rescue can be used as a procedure to isolate embryo's from crosses wherein plants fail to produce viable seed. In this process, the fertilized ovary or immature seed of a plant is tissue cultured to create new plants (this method is described in detail in Pierik, 1999).

A method of producing a ToTV-resistant plant thus comprises in one embodiment the steps of identifying a ToTV-resistant donor plant as described herein above and crossing said ToTV-resistant donor plant with a recipient plant, as described above, thereby producing resistant offspring plants.

A method of producing a ToTV-resistant plant further comprises the step of selecting from offspring plants a resistant plant by performing a method for identifying a ToTV-resistant plant as described earlier.

Preferably, said ToTV-resistant donor plant is a plant of the family Solanaceae or Cucurbitaceae, even more preferably a tomato plant, an eggplant plant, a pepper plant, melon plant, watermelon plant or a cucumber plant.

Preferably, said recipient plant is a plant of the family Solanaceae or Cucurbitaceae, even more preferably a tomato plant, an eggplant plant, a pepper plant, a melon plant, a watermelon plant or a cucumber plant. Still more preferably, said recipient plant is a tomato plant of the species *Solanum lycopersicum*, more preferably an *S. lycopersicum* plant that possess commercially desirable characteristics. The recipient plant may be a ToTV-susceptible plant, a ToTV sensitive plant or a ToTV resistant recipient plant. As explained above, the choice of the plant will primarily be determined by whether the resistance trait is dominant or recessive. The skilled person is aware of the various methodologies available to resolve such issues.

Also an aspect of the present invention is a ToTV-resistant plant, or a part thereof, obtainable by a method of the invention.

As stated, a preferred embodiment of a method for producing a ToTV-resistant plant comprises the transfer by introgression of said resistance-conferring nucleic acid sequence from a ToTV-resistant donor plant into a recipient plant by crossing said plants. Resistant plants developed according to this preferred embodiment can advantageously derive a majority of their traits from the recipient plant, and derive ToTV-resistance from the donor plant.

In one method, which is referred to as pedigree breeding, a donor plant that exhibits resistance to ToTV is crossed with a recipient plant that preferably exhibits commercially desirable characteristics, such as, but not limited to, disease resistance, insect resistance, valuable fruit characteristics, etc. The resulting plant population (representing the $F_1$ hybrids) is then self-pollinated and allowed to set seed ($F_2$ seeds). The $F_2$ plants grown from the $F_2$ seeds are then screened for resistance to ToTV. The population can be screened in a number of different ways, preferably by performing a method of the present invention for visual inspection.

Because the identification of ToTV-resistant plants has only at first been possible by the present invention, the method for producing the resistant plant is an aspect of the invention. Also an aspect of the present invention is a ToTV-resistant plant, or a part thereof, obtainable by a method of the invention.

The present invention provides for methods of preventing the spreading of ToTV infection in tomato plants by providing resistant tomato plants as well as by eliminating plants that carry the ToTV virus. These measures may form a part of a general strategy to improve phytosanitation in relation to ToTV virus. Tolerant plants may thus be identified and eliminated in order to eliminate such sources of the ToTV virus.

In one embodiment of a method for producing a ToTV-resistant plant, or part thereof, the present invention provides a method of producing a ToTV-tolerant plant. A tolerant plant may provide valuable crop, fruits and seeds, since, although the plant may harbour the virus, it does not exhibit disease symptoms. Such a method will involve the identification of tolerant plants, and the use of such tolerant plants as sources or donors of the desired genetic material. The aim is not to provide a plant capable of withstanding entry or multiplication of the virus in its cells, but to provide a plant which does not suffer from symptoms.

Thus, the present invention relates to a method for identifying a ToTV-tolerant plant, comprising the steps of a) exposing a plant or plant part to a infective dosage of ToTV, and b) identifying said plant as a ToTV-tolerant plant when, after said exposure, disease-symptoms in said plant or plant part remain absent, and ToTV is present in said plant or plant part.

Determining the development of ToTV-induced disease-symptoms in infected plants may be performed by quantitative methods, e.g. wherein the period required for the development of discernible (e.g. visible) disease-symptoms is noted, or by qualitative methods wherein, after a certain period has lapsed, the plant is inspected for the absence of symptom expression or the reduction in severity of the symptoms is indicated.

In a preferred embodiment, the presence of ToTV in said plant or plant part is determined in step b) by performing a method comprising determining in said plant or plant part the presence of a ToTV virus or component thereof by reacting said plant or plant part with a polynucleotide according to the invention or an antibody according to the invention.

Diagnostic Kits

Methods and means provided herein are particularly useful in a diagnostic kit for diagnosing a ToTV virus infection by virological diagnosis. Such kits or assays may for example comprise a virus, a nucleic acid, a proteinaceous molecule or fragment thereof, and/or an antibody according to the invention.

The invention also provides a diagnostic kit for diagnosing a ToTV infection comprising a ToTV virus, a ToTV virus-specific nucleic acid, proteinaceous molecule or fragment thereof and/or an antibody according to the invention, and preferably a means for detecting said ToTV virus, ToTV virus-specific nucleic acid, proteinaceous molecule or fragment thereof and/or an antibody, said means for example comprising an excitable group such as a fluorophore or enzymatic detection system used in the art (examples of suitable diagnostic kit format comprise IF, ELISA, neutralization assay, RT-PCR assay, hybridisation assays). Suitable detection assays include direct and indirect assays, sandwich assays, solid phase assays such as those using plates or beads among others, and liquid phase assays. Assays suitable include those that use primary and secondary antibodies, and those that use antibody binding reagents such as protein A. Moreover, a variety of detection methods can be used in the invention, including colorimetric, fluorescent, phosphorescent, chemiluminescent, luminescent and radioactive methods.

To determine whether an as yet unidentified virus component or synthetic analogue thereof such as nucleic acid, proteinaceous molecule or fragment thereof can be identified as ToTV-virus-specific, it suffices to analyse the nucleic acid or amino acid sequence of said component, for example for a stretch of said nucleic acid or amino acid, preferably of at least 10, more preferably at least 25, more preferably at least 40 nucleotides or amino acids (respectively), by sequence homology comparison with the provided ToTV viral sequences and with known non-ToTV viral sequences (preferably the closest phylogenetic relative of ToTV is used) using for example phylogenetic analyses as provided herein. Depending on the degree of relationship with said ToTV or non-ToTV viral sequences, the component or synthetic analogue can be identified.

A kit for detecting a ToTV virus may, depending on the assay format, include one or more antibodies specific for a protein, preferably specific for at least one capsid protein of ToTV, and preferably also includes a substantially purified ToTV protein or anti idiotypic antibody for use as a positive control.

Antiviral Agents

The invention also provides methods to obtain an antiviral agent useful in the treatment of ToTV infection in plants comprising establishing a cell culture or experimental plant comprising a virus according to the invention, treating said culture or plant with an candidate antiviral agent, and determining the effect of said agent on said virus or its infection of said culture or plant. An example of such an antiviral agent comprises a ToTV-neutralising antibody, or functional component thereof, as provided herein, but antiviral agents of other nature may be obtained as well.

There are different antiviral agents used in plants, such as chemical products, bacteria, fungus, insects and virus. Most of them are related to systemic acquired resistance (SAR). The present invention contemplates the use of the ToTV genome or a part thereof as an inductor of systemic acquired resistance in plants. The systemic acquired resistance may be directed to ToTV or to other diseases. In this aspect, ToTV, its genome, or resistance-conferring parts thereof can be used as antiviral agent.

The invention also provides use of an antiviral agent according to the invention for the preparation of a treatment composition, in particular for the treatment of ToTV infection in plants, and provides a pharmaceutical composition comprising an antiviral agent according to the invention, useful in a method for the treatment or prevention of a ToTV virus infection, said method comprising providing such a treatment composition to an individual plant.

The invention also relates to a plant model usable for testing of treatment methods and/or compositions. It has appeared that several *Nicotiana* species can be infected with the ToTV virus, thereby showing disease-symptoms dissimilar to those found in tomato plants suffering from the ToTV virus. Subjecting plants of *Nicotiana* to an antiviral treatment either before or during infection with the virus may have predictive value for application of such an antiviral agent in tomato plants.

The invention also relates to the use of ToTV, or parts of the ToTV viral genome, as expression vector, for instance for use in virus-induced gene silencing (VIGS). VIGS is a technology that exploits an RNA-mediated antiviral defence mechanism in plants. In plants infected with unmodified viruses the mechanism is specifically targeted against the viral genome. By using viral expression vectors carrying inserts derived from host genes the mechanism can also be used to target against the corresponding plant RNAs. VIGS has been used widely in plants for analysis of gene function and has been adapted for high-throughput functional genomics. Until now most applications of VIGS have been in *Nicotiana benthamiana*. However, the present invention contemplates the use of ToTV as new expression vector systems that allows for the analysis of gene function in other plants, such as tomato or other species of the family Solanaceae, such as pepper and potato and in species of the family Cucurbitaceae.

The invention is further explained in the Example without limiting it thereto.

EXAMPLES

Example 1

Isolation and Characterization of ToTV from Tomato Plants

Methods

Introduction

Samples of tomato plants from Spain were received for diagnostic research. Symptoms on tomato plants consisted of necrotic spots and chlorosis on the leaves and brown rings on the fruits. Serological tests (ELISA) pointed out the presence of Pepino mosaic virus (PepMV), but, considering the symptoms, it was likely that another, still undefined, agent was present.

Spherical virus particles were found in electron microscopic studies of infected leaf tissue.

Subsequently an infection test was conducted and multiple accessions of tomato were found to be susceptible for ToTV, several of which reacted with clear symptoms (necrosis of the leaves, beginning at the base of the individual leaflets (see FIG. 1).

Virus Transmission and Propagation

ToTV was isolated as described below from a diseased plant obtained from Spain. ToTV was mechanically transmissible to several *Nicotiana* species. A standard inoculation buffer (e.g. 0.03 M phosphate buffer, pH 7.7) proved suitable. Throughout this Example, ToTV was mechanically inoculated onto and propagated in *N. glutinosa* or *N. benthamiana*. Virus purification was carried out approximately 14 days after inoculation.

Virus Purification

Several attempts were made to purify ToTV according standard protocols for e.g. nepoviruses or luteoviruses (with the aid of organic solvents). These protocols resulted always in loss of infectivity of the virus. Moreover, ToTV tended to aggregate when low temperatures were used in centrifugation steps (below 5° C.).

Eventually a very mild purification method resulted in reasonable clean virus preparations on which further experiments could be carried out.

The following procedure was used to purify ToTV (all centrifugation steps were performed at 6° C.). Infected leaves of *N. glutinosa* or *N. benthamiana* were homogenized in 5 parts of 0.1 M TRIS-HCl (pH 8) plus 20 mM $Na_2SO_3$, 10 mM Na-DIECA en 5 mM Na-EDTA (homogenization buffer) and the homogenate was centrifuged for 30 min. at 49,000×g. The supernatant was placed on a 20% sucrose cushion and centrifuged for 1.5 h at 70,000×g. The pellet was resuspended in 2 ml TRIS-HCl, pH 8, and the suspension was placed onto a sucrose gradient (10-40% sucrose in homogenization buffer) and centrifuged for 2 h at 110,000×g. Since a virus band was not visible, the gradient was aliquoted into discrete fractions and the presence of virus in each fraction was determined by inoculation of a portion of said fraction on leaves of *N. hesperis* '67A' as described herein and observing the occurrence of infection. The virus-containing fraction was placed onto a 10-40% cesium sulfate gradient (in TRIS-HCl, pH 8) and centrifuged for 16 h at 125,000×g. The virus bands were collected and concentrated by centrifugation or dialyzed against 0.1 M TRIS-HCl, pH 8.

Infectivity of ToTV after each purification step was checked by inoculation onto *N. hesperis* '67A' (cesium sulfate gradient fractions were dialyzed against TRIS-HCl, pH 8, prior to inoculation).

Electron Microscopy

Virus suspensions were "mounted" on a grid coated with Formvar®, otherwise known as polyvinyl formal, stained with 2% uranylacetate and examined in a Philips CM12 electron microscope.

PAGE Analysis

Viral proteins were separated by 12% denaturing polyacrylamide gel electrophoresis (SDS-PAGE, Laemmli, 1970) and silver-stained.

Nucleic Acid Isolation and Evaluation

Purified virus was concentrated by centrifugation (2 h at 115,000 g). Pellets were subjected to RNA extraction according to the Qiagen RNeasy MinElute Cleanup procedure (Qiagen, Hilden, Germany). RNA concentration was determined in a UV-spectrophotometer (Beckman Coulter, Inc., Fullerton, USA).

RNA integrity was checked by agarose gel electrophoresis. After electrophoresis for 2 hrs at 60V, the RNA was stained using orthotoluidine blue.

cDNA Synthesis and Cloning cDNA was synthesised using the Invitrogen Superscript Choice system (Invitrogen, Breda, The Netherlands) for cDNA synthesis according to the manufactures instructions. First strand cDNA was primed using either Oligo-d(T) or random hexamer primers. After second strand synthesis, EcoRI adapters were ligated to facilitate cloning. Following phosphorylation of the EcoRI-adapted cDNA, unligated linkers were removed by column chromatography. The resulting cDNA was ligated in pBluescript II EcoRI pre-digested expression vector (Stratagene, La Jolla, USA) and the ligation mix transformed to Top10 competent cells (Invitrogen).

The 5' terminal end of the ToTV sequence was determined using the 5'RACE System for Rapid Amplification of cDNA Ends (LifeTechnologies) using dCTP according to the manufacturer's instructions.

Analysis of cDNA

Upon transformation recombinant clones were analysed for the presence of inserts by PCR using both T3 and T7 specific primers. PCR products were analysed for size on a 1% agarose gel. Clones containing inserts of about 1500 nucleotides were used for further sequence analysis. Resulting sequence data were analysed using the DNASTAR program package.

Determination of Amino Acid Sequences of the Three Capsid Proteins of ToTV.

Purified ToTV particles were loaded onto a denaturing PAGE gel and capsid proteins were separated. Separated capsid protein bands were isolated from the gel, treated with trypsin and the digests were analyzed using a tandem mass spectrometer (MSMS) using essentially the method as described by Kinter & Sherman, 2000. This resulted in amino acid (AA) sequences of small peptides each of which showed homology with the amino acid sequence predicted from the RNA2 nucleotide sequence of ToTV. Comparison with other virus sequence data was done with programs from the PHYLIP package.

Results

Virus Transmission and Propagation

For ToTV propagation *N. glutinosa* and *N. benthamina* could be used. The tobacco species *N. hesperis* '67A' and *N. occidentalis* '*P*1' are very susceptible to ToTV and showed symptoms after 3-4 days. These tobacco species became very necrotic in short time and were therefore considered more suitable as indicator plant than as propagation host. *N. glutinosa* and *N. benthamiana* react with chlorotic local lesions and a systemic chlorosis and mild deformation of the leaves.

Virus Purification

Purification of virions from infected leaf tissue turned out to be rather difficult. ToTV cannot resist organic solvents and tends to aggregate when centrifuged at low temperatures. The purification protocol used (see 1.2.) resulted in two visible virus-containing bands in the cesium sulfate gradient. The bands appeared in the bottom part of the gradient, indicating a rather high buoyant density in $Cs_2SO_4$ of equal to or greater than 1.4 g/cm$^2$.

The infectivity of ToTV is affected by cesium sulphate, but not completely lost when the virus concentration in the starting material was high. Fractions of the cesium sulphate-gradient containing both virus bands were infectious. Infectivity of individual bands was not determined.

Electron Microscopy

The two bands were examined by electron microscopy and both contained virus particles of about 28 nm in diameter (FIG. 2).

PAGE Analysis

Polyacryl Amide Gel Electrophoresis (PAGE) of purified virus fractions, followed by silver-staining of the gel showed three capsid proteins (CP) of approximately 23, 26 and 35 kDa (see FIG. 3, indicating purified virus top (TAgV-T) and bottom (TAgV-B) fractions).

Nucleic Acid Isolation and Analysis of cDNA

RNA isolation of both virus bands together revealed two RNA's: approximately 5.5 kb and 8 kb (see FIG. 4). RNA isolation of the upper band resulted in a 5.5 kb RNA fragment only.

The 5.5 kb RNA from the top band was used as the template for cDNA synthesis and cloning. Sequence reactions were performed using forward and reverse sequence primers (T3/T7 or M13F/M13R) on different clones. A 5' Rapid Amplification of cDNA Ends (RACE) was performed to determine the exact 5'-end of the RNA. Analysis of the resulting sequence data, using the Lasergene® software package (DNASTAR, Inc., Madison, Wis., USA), resulted in the complete sequence of RNA2 of the virus (SEQ ID NO:1; see FIG. 5). The size of the RNA is 5389 nucleotides excluding the poly A tail. On the RNA two open reading frames (ORF's) are found. ORF1 is located from nucleotide 182 to 742, is 561 nucleotides in length, and codes for a protein of 187 amino acids. No homologies were found for this sequence in the NCBI databases on protein and nucleotide level.

ORF2 stretches from nucleotide 702 to 4298, is 3597 nucleotides in length, and encodes a protein of 1199 amino acids. After a BLAST search in the NCBI database, low homologies were found with several viral polyproteins. For the found homologies, the accession numbers from the NCBI database are provided together with the virus name and the type of protein. Both the nucleic acid sequences and derived amino acid sequences in all three reading frames were used in a BLAST analysis. MAPDRAW from Lasergene® software package was use to identify the ORFs.

ORF Maps of Both RNA's:

RNA1

RNA1 contains one ORF (ORF1) with motifs typical of helicase, RNA dependent RNA polymerase (RdRp). In addition a low level of amino acid (aa) sequence homology was observed with a protease co-factor (Pro-Co) of Patchouli mild mosaic virus (PatMMV) (NP647592.1), for the amino acid positions 106-338, with an identity of 22%.

Typical Helicase motifs A (GKS), B (D), C(N) were identified at aa positions 398-400, 444 and 495 of the putative polypeptide.

For the helicase region the closest identities were found with Rice tungro spherical virus (RTSV; 42% identical in 140 aa overlap), Maize chlorotic dwarf virus (MCDV; 43% identical in 137 aa overlap), Strawberry mottle virus (SMoV; 42% identical in 135 aa overlap) and Parsnip yellow fleck virus (PYFV; 42% in 138aa overlap). In the putative VpG region no sequence similarity with other viruses was found.

The highest similarity in protease is found for aa 1000-1100, 25% identity is found with Potato virus V (PVV; NIa protease in 86 aa overlap).

The RdRp region between motifs I (KDE) to VII (FLSR) was found between aa 1303-1554 (Koonin 1991).

The closest identities of the polyprotein sequence were found with: Rice tungro spherical virus (RTSV) with 29% identity in a 751 aa overlap, Maize chlorotic dwarf virus (MCDV) with 28% identity in a 742 aa overlap, Parsnip yellow fleck virus (PYFV) with a 33% identity in 501 aa, Apple latent spherical virus (ALSV) with 32% identity in 472 aa, Strawberry mottle virus (SMoV) with 30% identity in 680 aa and Cherry rasp leaf virus (CRLV) with 33% in 465 aa

TABLE 2

Overall levels of homology (in %) between the RdRp motifs in ORF1 on ToTV RNA1 with RdRp motifs of other plant viruses.

| | NIMV | PYFV | RTSV | SDV | SMoV | ToTV | ALSV | CRLV | MCDV |
|---|---|---|---|---|---|---|---|---|---|
| NIMV | 100 | 32.7 | 33.9 | 88.6 | 49.4 | 33.1 | 39.6 | 39.6 | 35.1 |
| PYFV | | 100 | 43.7 | 33.2 | 32.0 | 35.2 | 36.4 | 36.0 | 42.9 |
| RTSV | | | 100 | 34.3 | 32.7 | 35.1 | 37.5 | 35.1 | 69.4 |
| SDV | | | | 100 | 50.2 | 33.1 | 38.4 | 38.4 | 36.7 |
| SMoV | | | | | 100 | 35.7 | 40.6 | 38.5 | 38.5 |
| ToTV | | | | | | 100 | 38.1 | 38.1 | 33.7 |
| ALSV | | | | | | | 100 | 79.5 | 35.5 |
| CRLV | | | | | | | | 100 | 35.1 |
| MCDV | | | | | | | | | 100 |

NIMV = Navel orange Infectious mottling virus (Sadwa);
PYFV = Parsnip yellow fleck virus (Sequivirus);
RTSV = Rice tungro sperical virus (Waikavirus);
SDV = Satsumae dwarf virus (Sadwavirus);
SMoV = Strawberry mottle virus (Sadwavirus);
ToTV—Tomato torrado virus (genus proposed);
ALSV = Apple latent spherical virus (Cheravirus);
CRLV = Cherry rasp leaf virus (Cheravirus);
MCDV = Maize chlorotic dwarf virus (Waikavirus)

TABLE 3

Overall levels of homology (in %) between the helicase motifs in ORF1 on ToTV RNA1 with helicase motifs of other plant viruses.

| | SDV | SMoV | ToTV | ALSV | CRLV | MCDV | PYFV | RTSV |
|---|---|---|---|---|---|---|---|---|
| SDV | 100 | 42.5 | 37.2 | 31.9 | 33.6 | 39.8 | 39.8 | 38.1 |
| SMoV | | 100 | 42.5 | 31.0 | 31.9 | 32.7 | 33.6 | 32.7 |
| ToTV | | | 100 | 36.0 | 34.2 | 46.5 | 40.4 | 44.7 |
| ALSV | | | | 100 | 86.7 | 34.5 | 31.0 | 30.1 |

TABLE 3-continued

Overall levels of homology (in %) between the helicase motifs in ORF1 on ToTV RNA1 with helicase motifs of other plant viruses.

| | SDV | SMoV | ToTV | ALSV | CRLV | MCDV | PYFV | RTSV |
|---|---|---|---|---|---|---|---|---|
| CRLV | | | | | 100 | 34.5 | 30.1 | 31.0 |
| MCDV | | | | | | 100 | 39.8 | 69.0 |
| PYFV | | | | | | | 100 | 42.5 |
| RTSV | | | | | | | | 100 |

PYFV = Parsnip yellow fleck virus (Sequivirus);
RTSV = Rice tungro sperical virus (Waikavirus);
SDV = Satsumae dwarf virus (Sadwavirus);
SMoV = Strawberry mottle virus (Sadwavirus);
ToTV—Tomato torrado virus (genus proposed);
ALSV = Apple latent spherical virus (Cheravirus);
CRLV = Cherry rasp leaf virus (Cheravirus);
MCDV = Maize chlorotic dwarf virus (Waikavirus)

RNA2;

RNA2 contains two potential ORFs (FIG. 7). ORF1 encodes a predicted protein of 187 aa with a molecular weight of 20 kDa. Sequence analysis revealed no homologies with any protein from the EMBL databases. It is not known whether this ORF codes for an actual protein.

The second ORF which partially overlaps with ORF1 starts with three ATG start codons in frame. It encodes a putative protein of 1198 aa with a predicted molecular weight of 134 kDa. Protein identification by mass spectrometry of the isolated coat proteins clearly maps the three coat protein cistrons at the C-terminus of RNA2-ORF2.

The N-terminal region of the RNA2-ORF2 polyprotein most likely codes for the putative movement protein (MP) since a motif LRVPML highly similar to the proposed movement protein consensus sequence LxxPxL (Mushegian, 1994) was found at aa position 262-267. No other sequence homologies were found in the N-terminus of the RNA2 ORF2.

ORF2 putatively encodes four proteins which are must be cleaved from the polyprotein precursor by proteolytic cleavage. However, no apparent homologies with known polyprotein cleavage sites could be identified. The exact positions of these cleavage sites remain to be determined.

For CP1 polyprotein sequence we found only any homology with Human parechovirus (HPeV) with 21% identity in 103 aa.

The closest identities of the CP2 polyprotein sequence were found with: Rhopalosiphum padi virus (RhPV) with 25% identity in 168aa, Avian encephalomyeliltis virus (AEV) with 33% in 74 aa, Black queen cell virus (BQCV) with 43% identity in 37 aa and Solenopsis invicta virus (SINV-1) with 30% indentity in 51 aa. With the CP3 polyprotein sequence no homologies were found.

Untranslated Regions (UTRs)

The 3'UTRs of RNA1 and RNA2 are 1210 nt and 1092 nt respectively. There is 98% identity in the final 988 nucleotides of both RNA's. To confirm that the 3'-regions of the UTRs of both RNAs are identical, RT-PCRs were performed on total viral RNA with one reverse primer derived from the identical 3'-UTR region and two RNA specific forward primers. Resulting PCR products were sequenced.

From these results, the following was concluded: The virus isolated from tomato plants and tentatively named Tomato torrado virus (ToTV) has spherical (icosahedral) particles of approximately 28 nm in diameter. Upon purification the virus displays at least two bands in a cesium sulphate-gradient. Both bands combined are infectious when inoculated on tobacco plants. Virus particles appear to consist of at least three capsid proteins of approximately 23, 26 and 35 kDa.

The cesium sulphate-gradient top fraction of the virus contains an RNA molecule of approximately 5.5 kb (RNA 2; SEQ ID NO:1) and the bottom fraction an RNA molecule of approximately 8 kb (RNA 1; SEQ ID NO:2).

cDNA synthesis and cloning, using the 5.5 kb RNA from the viral top fraction, and subsequent analysis of sequence information, resulted in the compilation of several contigs into SEQ ID NO: 1. Two contigs clearly contained a poly-A tail suggesting the viral RNA has a poly-A tail. BLAST analysis of the nucleotide and derived amino acid sequences did not reveal any significant homology with any known virus from the EMBL database.

The information above indicates that ToTV is a new and so far undescribed virus. The information obtained so far does not yet allow a grouping of the virus in a particular virus family or genus.

For virus detection and identification purposes two RT-PCR-primer sets have been designed (Table 4) on the basis of the sequence of SEQ ID NO:1.

TABLE 4

RT-PCR primers for the detection of ToTV.

| | length/ temp | Sequence | SEQ ID No. |
|---|---|---|---|
| Primer set A: | | | |
| forward primer | 17-mer | 5'-GAGAGCCGGCATTCACA-3' | SEQ ID NO: 3 |
| reverse primer | 17-mer | 5'-GCACAGCTTGGCGACAC-3' | SEQ ID NO: 4 |
| Product length | 493 bp | | |
| Optimal annealing temp. | 54.8° C. | | |

TABLE 4-continued

RT-PCR primers for the detection of ToTV.

| | length/ temp | Sequence | SEQ ID No. |
|---|---|---|---|
| Primer set B: | | | |
| forward primer | 24-mer | 5'-CCCATCATCACCCTCCTCTTCGTA-3' | SEQ ID NO: 5 |
| reverse primer | 22-mer | 5'-TTCCAGTAATGATCCAACCAAT-3' | SEQ ID NO: 6 |
| Product length | 585 bp | | |
| Optimal annealing temp. | 54.9° C. | | |

A suitable RT-PCR Protocol would comprise the following. Total RNA is isolated and purified from about 100 μg of infected leaf material using a RNA purification kit, such as for instance Qiagen RNA-Easy. Of this total RNA, an amount of about 1 μg of is used in a 50 μl reaction mixture of the Superscript One-Step RT-PCR reaction (Invitrogen), which reaction mixture further comprises 25 μl 2× reaction mix, 1 μl (100 ng) of both upper primer and down primer, 1 μl of RT/Taq mix and 22 μl of MilliQ water. In order to reverse transcribe the RNA into cDNA and amplify this cDNA the following RT-PCR programme may be used: Step 1: 30 min @ 50° C. (Reverse transcription reaction); Step 2: 3 min @ 94° C. (activation of Taq Polymerase); Step 3: 30 sec @ 94° C.; Step 4: 30 sec @ 55° C.; Step 5: 1 min @ 72° C.; Step 6: Repeat steps (3 to 5) 40×; Step 7: 10 min @ 72° C.; Step 8: 10° C. as long as needed. PCR products may be analysed on a 1% agarose gel in TAE or TBE buffer.

2.6. Determination of Amino Acid Sequences of the Three Capsid Proteins of ToTV.

Fragments of the largest coat protein (CP1: approximately 35 kDa) could be aligned with parts of an area in the ORF2 of RNA2 (AA 487-729). Fragments of the middle coat protein band (CP2: app. 26 kDa) could be aligned with an area of ORF2 of RNA2 between AA 730 and 983.

Fragments of the smallest coat protein (CP3: app. 23 kDa) could be aligned with the C-terminus of ORF2 of RNA2 (AA 984-1195). From these results it can be concluded that the coding sequences of the three capsid proteins are located on the ORF2 of RNA2 (5.5 kb) of ToTV, and thus that the isolated viral RNA molecules are part of the ToTV virus particles.

Example 2

Isolation and Characterization of the Causal Agent of Marchitez

In 2003, tomato plants grown in Central America (Mexico and Guatemala) with symptoms similar to symptoms of ToTV were found. The causal agent was suspected to be viral. The disease is locally known under the names "Chocolate", "Marchitez (virus)" or "Chocolate spot disease". Susceptible plants grown in the field become heavily infected from 2003 onwards.

The goal of the present investigation was to compare the sequence of the so-far unknown virus causing the "Chocolate spot disease" to the sequence of ToTV as isolated in Example 1.

Methods

RNA was isolated from about 100 μg of "Chocolate spot disease" infected leaf material using the Total RNA Isolation System (Promega SV 96). Two μl of the total RNA was used in a 50 μl reaction mixture of the Superscript One-Step RT-PCR reaction (Invitrogen), which reaction mixture further comprises 25 μL 2× reaction mix, 1 μl (100 ng) of both forward primer and reverse primer, 1 μl of RT/Taq mix and 22 μl of MilliQ water. In order to reverse transcribe the RNA into cDNA and amplify this cDNA the following RT-PCR program was used: Step 1: 30 min @ 50° C. (reverse transcription reaction); Step 2: 3 min @ 94° C. (activation of Taq Polymerase); Step 3: 30 sec @ 94° C.; Step 4: 30 sec @ 55° C.; Step 5: 1 min @ 72° C.; Step 6: Repeat steps (3 to 5) 40×; Step 7: 10 min @ 72° C.; Step 8: 10° C. as long as needed. PCR products were analysed on a 1% agarose gel in TAE or TBE buffer.

Different primer sets were used in the RT-PCR, which were known to anneal at different locations with the RNA1 or RNA2 of the ToTV genome.

TABLE 5

RT-PCR primers based on the RNA-2 sequence of ToTV used for the characterization of the casual virus of Chocolate spot disease as used in Example 2 and as indicated in FIG. 7.

| | Sequence | SEQ ID No. |
|---|---|---|
| Primer set P1048/1049: | | |
| forward primer | 5'-CAAGCCATCACGGAACCTAC-3' | SEQ ID NO: 7 |
| reverse primer | 5'-AGCATCTTCTTCCTCCGCT-3' | SEQ ID NO: 8 |
| Product length | From base 36 - 544 = 508 bases | |

TABLE 5-continued

RT-PCR primers based on the RNA-2 sequence of ToTV used for the characterization of the casual virus of Chocolate spot disease as used in Example 2 and as indicated in FIG. 7.

| Sequence | SEQ ID No. |
|---|---|
| Primer set P1056/1057: | |
| forward primer 5'-TGCTGAGGTGCTATCACTGG-3' | SEQ ID NO: 9 |
| reverse primer 5'-CACACTTTCCACGATTTCCA-3' | SEQ ID NO: 10 |
| Product length From base 2422 - 2955 = 523 bases | |
| Primer set P1060/1061: | |
| forward primer 5'-AAAGGAAAGAAGCAGCCACA-3 | SEQ ID NO: 11 |
| reverse primer 5'-GGAAATCTTGGTCAAGCCAG-3' | SEQ ID NO: 12 |
| Product length From base 3599 - 4170 = 571 bases | |
| Primer set P1064/1065: | |
| forward primer 5'-GCAATGCCAGTGGTTCAGAG-3' | SEQ ID NO: 13 |
| reverse primer 5'-GGTCAAATGGATACTCGGGA-3' | SEQ ID NO: 14 |
| Product length From base 4820 - 5327 = 507 bases | |

Results

The primer sets used promoted the amplification of part of the ToTV sequence as expected, but the use of four different primer sets based on the RNA-2 sequence (P1048/1049, P1056/1057, P1060/1061 and P1064/1065) in the RT-PCR resulted also in amplification of part of the "Chocolate spot disease" genome. The site of annealing of these primer sets is illustrated in FIG. 1.

The RT-PCR-product of the four primer sets that amplified fragments of "Chocolate spot disease" were sequenced, and showed 100% identity with the corresponding parts of the sequence of the viral genome of the virus as described in Example 1.

Example 3

Isolation and Characterization of the Causal Agent of Marchitez

Following the Experiments described in Example 2, additional diseased planbt material from the same location in Mexico (Sinaloa) was investigated. The disease referred to is locally known as "Marchitez", meaning wilted or withered. Because of the resemblance in leaf symptoms, it was assumed that Marchitez disease was caused by ToTV and initial experiments described in Example 2 confirmed this notion. However, testing of further material, ToTV could not be detected using PCT with ToTV-specific primers. In the further tested material, a spherical virus was found that shared characteristics with ToTV. In this Example we describe and characterize this new virus, related to but distinct from ToTV. This new virus is tentatively named tomato marchitez virus (ToMarV).

Material and Methods

Virus Transmission and Propagation

ToMarV was isolated in 2005 from a tomato plant from Culiacán, Sinaloa, Mexico, that showed severe necrosis. The isolate was designated PRI-TMarV0601. Using a 0.03 M sodium/potassium phosphate buffer, pH 7.7, the virus was mechanically inoculated to and maintained in *Nicotiana glutinosa* 'PRI', *Physalis floridana* or *N. benthamiana.*

Virus Purification

All centrifugation steps were carried out at 6° C. Systemically infected leaves of *N. benthamiana* were harvested approximately 14 days post inoculation and homogenized in 5 volumes (W/V) extraction buffer (0.1 M Tris-HCl, pH8+20 mM $Na_2SO_3$, 10 mM Na-DIECA en 5 mM Na-EDTA) and squeezed through cheesecloth. Three volumes of an 1:1 mixture of Chloroform/Butanol were added and after mixing, the suspension was centrifuged at 16,500 g for 10 min. 1% Triton X-100 was added to the water phase and stirred for 30 min. 5% PEG 6000 and 2.3% NaCl was added and the suspension was stirred for 1 h. The suspension was left to settle for 1 h and centrifuged for 15 min at 21,500 g. The pellets were resuspended in a total of 80 ml extraction buffer, centrifuged for 10 min at 15,000 g and the supernatant was placed on a 30% sucrose cushion. After centrifugation for 3 h at 70,500 g, the pellets were resuspended in a total of 2 ml Tris buffer pH 8.0 and centrifuged for 2 min at 14,000 g. The virus suspension was loaded onto a 10-40% Cesium sulfate gradient and centrifuged for 16 h at 126,000 g. Virus bands were collected and dialyzed against 0.1 M Tris-HCl, pH 8.0.

Electron Microscopy

Virus suspensions were mounted on formvar-carbon coated grids, stained with 2% uranyl acetate and examined in a Philips CM12 electron microscope.

Polyacrylamide Gel Electrophoresis

Viral proteins were separated by subjecting purified virus particles to 12% denaturing polyacrylamide gel electrophoresis (SDS-PAGE) [Laemmli UK (1970) Nature 277: 680-685], and visualized by silver staining.

Nucleic Acid Isolation and Evaluation

Purified virus was concentrated by centrifugation (at 115,000 g for 2 h). RNA was extracted from pelleted virus particles using a Qiagen RNeasy kit (Qiagen) according to the manufacturer's instructions.

RNA concentration was determined in a Beckmann UV-spectophotometer. Viral RNA integrity and size was checked on a 1% agarose gel using a formaldehyde/formamide/HEPES buffer system. After electrophoresis, the RNA was stained using ortho-toluidine blue.

Total RNA for RT-PCRs, was isolated with the RNeasy plant mini kit (Qiagen) from ToMarV infected *Nicotiana* occidentalis 'P1' plants.

RT-PCR and 5' RACE

PCR fragments were obtained by one-tube RT-PCR (Access RT-PCR system, Promega). RT-PCRs were initiated using a universal oligo dT primer [Van der Vlugt et al. (1999). *Phytopathology* 89: 148-155] and various primers derived from the ToTV RNA 1 and RNA 2 sequences (respectively GenBank accession numbers DQ388879 and DQ388880 The 5' regions of the ToMarV RNAs were determined by walking towards the 5' end of the viral genome through repeated use of a 5' RACE kit (Roche) in combination with the Expand high fidelity PCR system (Roche), essentially as described previously [Ongus J R, et al. (2004). *J Gen Virol* 85: 3747-3755, Valles S M, et al. (2004) *Virology* 328: 151-157]. cDNA primers for the 5'-RACE strategy and primer sets for additional RT-PCR reactions were based on newly obtained ToMarV sequence data.

Nucleotide Sequencing and Sequence Analysis

All PCR products the 5' RACE) were purified using the QIAquick PCR Purification Kit (Qiagen) and directly sequenced.

Sequence analysis was performed with an Applied Biosystems 3100 Genetic Analyser, using the DYEnamic ET Terminator Cycle Sequencing Kit (Amersham) and the primers that were used for amplification. For longer PCR fragments ToMarV specific primers were used for primer walking sequencing.

Nucleotide and amino acid sequence data were analyzed and assembled using the DNASTAR package (Lasergene).

Sequence comparisons with other viruses were performed with programs from the PHYLIP package. Multiple alignments and phylogenies were performed with the CLUSTAL X program after bootstrapping in 1000 replicates. Neighbour-joining concensus phylogenies were viewed by the NJplot program [Thompson J D, et al. (1997) *Nucleic Acids Res* 25: 4876-4882] and printed by using TreeView [Page RDM (1996) *Computer Applications in the Biosciences* 12: 357-358].

Results and Discussion

Virus Characterization

ToMarV was easily transmitted to a number of indicator plants by mechanical inoculation. In table 1 an overview is given of the indicator plants used and their reactions to ToMarV and ToTV. Most symptoms of ToMarV and ToTV in indicator plants resemble each other, except for the reactions in *P. floridana* and *Chenopodium* quinoa. ToTV causes severe necrosis and die off in *P. floridana*, where ToMarV induces only occasionally necrosis in the local infected leaves and a systemic mottle. *C. quinoa* shows no reaction when inoculated with ToTV, but ToMarV induces necrotic pin point lesions in the inoculated leaves.

Electron microscopical studies in tomato showing Marchitez symptoms and in systemically infected leaves of *Nicotiana occidentalis* 'P1' revealed the presence of spherical virus particles with a diameter of 28-30 nm. The particles of ToMarV clearly resemble the particles of ToTV in shape and size.

In initial attempts to purify ToMarV the purification protocol designed for ToTV was used (see Example 1). This protocol did not lead to visible virus bands in the final cesium sulfate ($CsSO_4$) gradient. Electron microscopical analysis of gradient fractions revealed that virus particles were present in the bottom part of the gradient. However, this part of the gradient contained also plant components, veiling the virus bands. Therefore another purification protocol was designed in which the separation of the virus from plant components was aided by the use of a chloroform-butanol mixture. This protocol resulted in one diffuse band in the $CsSO_4$ gradient. This result is in contract with that obtained for ToTV purifications, which always yielded two distinct bands in $CsSO_4$ gradient centrifugation. The ToMarV band was collected from the gradient and checked by electron microscopy. Virions of the expected size of 28 nm were present in the collected band, and were infectious when mechanically transmitted to test plants. Purified virions were also mechanically transmitted to tomato plants, which showed characteristic symptoms of Marchitez disease two weeks after inoculation. Presence of ToMarV in these plants was confirmed by electron microscopy and RT-PCR.

Purified virions were subjected to SDS-PAGE and three viral proteins were detected with estimated sizes of 35, 26 and 24 kDa, named respectively Vp35, Vp26 and Vp24 (FIG. 11A). The number and estimated molecular sizes of the viral coat proteins of ToMarV are the same as previously found for ToTV (see Example 1).

Purified virus preparations of tomato marchitez virus showed two RNA molecules on a denaturing RNA-gel:RNA1 with an estimated size of 7.5 kb and RNA2 with an estimated size of 4 kb (FIG. 11B). The number of RNAs found is in accordance with ToTV, but their estimated sizes are smaller (8.5 and 5.5 kb for ToTV RNA1 and RNA2 respectively).

Viral RNA Analysis

Based on biological and structural data like indicator plant symptoms, particle sizes and morphology, number and sizes of coat proteins, and number of RNAs obtained for ToMarV, a possible relationship with ToTV was suspected. Therefore different upstream primers based on the ToTV RNA1 and RNA2 sequences (DQ388879 and DQ388880) in combination with a general oligo-dT primer, were used to perform RT-PCR reactions. This resulted in a limited number of PCR fragments indicating possible differences in RNA sequences between the two viruses. Sequence analyses of these fragments revealed low levels of homology with the ToTV RNAs 1 and 2. Based on the obtained sequence information new cDNA primers were generated and used to obtain additional sequence information in a 5'-RACE sequence walking strategy.

ToMarV specific primers were used for RT-PCRs to confirm sequences of both RNAs in two orientations.

RNA1

RNA1 (FIG. 8) consists of 7221 nucleotides (nts), without poly(A) tail and contains one open reading frame (RNA1-ORF1) of 6453 nts encoding a predicted polyprotein of 2151 amino acids (aa) with a molecular mass of 237 kDa (FIG. 12). The first in-frame AUG is found at nt positions 141-143. The ORF has an UGA stop codon at positions 6594-6596. The putative polyprotein sequence contains several conserved regions with motifs typical for a protease co-factor, helicase, protease and RNA-dependent RNA polymerase (RdRp).

Typical helicase motifs A (GKS), B (D), C(N) were identified at aa positions 397-399, 443 and 494 of the putative protein. The RdRp region could be identified between aa 1305 and 1553 by the presence of the typical motifs I (KDE) to VII (FLSR) [Koonin EV (1991). *J Gen Virol* 72: 2197].

The ORF1 encoding region shows 65% overall identity with the ToTV-RNA1 (DQ388879) at both the nucleotide level (6474 nts) and the amino acid level (2158 aa).

The helicase region between motifs A and C [Gorbalenya A E, et al. (1990). *FEBS Lett* 262: 145-148] in the C-terminal part of RNA1-ORF1 showed 95.6% aa identity with the corresponding region from ToTV and significantly lower levels of identity with other viruses ranging from 46.9% for maize chlorotic dwarf virus (MCDV, genus Waikavirus, AAV86083) to 25.4% for acute bee paralysis virus (ABPV, unassigned species in the family Dicistroviridae, NP_066241).

Levels of aa identity for the RdRp motif in ORF1 of RNA1 were relatively high with ToTV (78.2%) and significantly lower with other viruses, ranging from 15.3% for avian encephalomyelitis virus (AEV, genus Hepatovirus, NP_653151) to 25.9% for strawberry latent ringspot virus (SLRSV, genus Sadwavirus, NC_006764). These levels of identity indicate a close level of relationship between ToMarV and ToTV.

A BLAST search with our available data also revealed a remarkably high level of overall sequence homology (95%) with a partial sequence in the NCBI data base of tomato apex necrosis virus (ToANV, Genbank accession number EF063641) which became only available during the course of our work. In the coding region of RNA1 the overall level of identity between ToMarV and ToANV is 96% at the nt level and 99% at the protein level with levels of aa identity of 99.3 and 100% for the RdRp and Helicase motifs respectively. These percentages suggest a close level of relationship between ToMarV and the partial virus sequence submitted under the name of apex necrosis virus (ToANV).

RNA2

RNA2 (FIG. 9) consists of 4906 nt, and in analogy with ToTV, contains two open reading frame (RNA2-ORF1 and RNA2-ORF2) encoding two predicted polyproteins (FIG. 12). The overall level of sequence identity between RNA2-ORF1 of ToMarV and ToTV is 62.1%.

The highest sequence identity (80%) was found with the published partial sequence of ToANV-RNA2 (Gen bank accession no. EF063642). In the coding region the identity is 78% at nt level and 90% at protein level.

In analogy with ToTV, the N-terminal region of the RNA2-ORF1 polyprotein most likely codes for the putative MP since a motif <u>L</u>RV<u>P</u>T<u>L</u> highly similar to the prosposed movement protein consensus sequence LxxPxL [Mushegian AR (1994). *Arch Virol* 135: 437-441] was found.

The sequence of the putative movement protein region of ToANV is not available.

The relative order of the three putative coat proteins of tomato marchitez virus on the RNA2-ORF2 was derived from direct sequence comparisons with the ToTV CPs. No obvious homologies could be identified with regions which were identified earlier as putative CP cleavage sites for ToTV CPs [Verbeek M, et at (2007). Arch Virol 152:881-890].

For ToTV the coat proteins were sequenced to locate the coat protein genes on the RNA2 sequence. The amino acid sequences of the individual coat proteins of ToMarV, ToTV and ToANV are compared.

ToMarV-Vp35 shows 89% and 72% identity to ToANV and ToTV.

ToMarV-Vp26 shows 98% and 86% identity to ToANV and ToTV.

ToMarV-Vp24 shows 94% and 71% identity to ToANV and ToTV.

5'- and 3'-Untranslated Regions (UTRs)

The 5'-UTR size of RNA1 is 140 nt. That of RNA2 could not yet be reliably determined. The 3'-UTRs of RNA1 and RNA2 are 628 nt and 655 nt, respectively, in length and share an overall level of identity of 91%. The 553 most 3'-terminal nucleotides of both RNAs are almost perfectly conserved (99% identity). The near identical regions in the 3'-part of both 3'-UTRs is a characteristic that tomato marchitez virus shares with ToTV. However direct sequence comparisons between the total 3'-UTRs of RNA1 and RNA2 of ToMarV and ToTV reveals only 49.0% and 48.9. % sequence identity respectively between the two viruses.

A comparison to the 3'-UTRs of ToANV with respective lengths of 630 nts and 650 nts for RNA1 and RNA2, shows 88.5% and 85.6% sequence identity with RNA1 and RNA2 of ToMarV. This is significantly lower then the levels of identity observed in the Helicase and CG-GDD regions found in the ORF encoded on RNA1.

Taxonomic Position of ToMarV

Tomato marchitez virus shares virion characteristics and its genome organization with ToTV but based on levels of nt and aa sequence identities the two viruses are related but distinct. Remarkably high levels of identities are observed between ToMarV RNA1 and RNA2 and a sequence deposited in the NCBI database under the name of tomato apex necrosis virus (ToANV). No additional data on the virus from which these partial sequences were derived are available. However, the relative low levels of nucleotide sequence identities (less than 90%) in the 3'-NTRs of both RNA1 and RNA2 (88.5% and 85.6% respectively), as well less then 90% aa identity (89%) in the largest putative CP (Vp36) between the two viruses, suggests that the two viruses are not identical and may be strains or isolates of the same virus. Additional biological and molecular data on the virus from which the ToANV sequence was derived will be needed to determine its precise relationship to ToMarV.

Phylogenetic analysis based the aa region between the CG protease motif [Bazan J F, Fletterick R J (1988). *Proc Natl Acad Sci USA* 85: 7872-7876] and the GDD RdRp active site [Argos P (1988). *Nucleic Acids Res* 16: 9909-9916] in the RNA1-ORF were performed to determine the relationships between tomato marchitez virus, ToTV and other viruses from the genera Sadwavirus, Cheravirus and the families Sequiviridae, Comoviridae, Dicistroviridae and Picornaviridae. This region is proposed to be a good taxonomic predictor for classifying picorna-like viruses [Ikegami M et al. (2002) Taxonomy of recognized and putative species in the family Comoviridae. XIIth IDMS Virology meeting Paris, France, 27 Jul.-12 Aug. 2002]. The resulting dendrogram (FIG. 13A) shows that ToMarV virus clusters with ToTV and ToANV and confirms the separate taxonomic position of these viruses from the genus Cheravirus. A similar phylogenetic analysis on basis of the helicase region between the motifs A and C [Gorbalenya A E, et al. (1990). *FEBS Lett* 262: 145-148] (aa 397-494) confirms the taxonomic positions of ToMarV, ToTV and ToANV (FIG. 13B). For this motif these viruses seem to be more closely related to the genera Waikavirus and Sequivirus.

The data we present in this Example describe Tomato marchitez virus (ToMarV) as a new picorna-like plant virus, related to but distinct from tomato torrado virus (ToTV) [Verbeek M, et al. (2007) *Arch Virol* 152:881-890] ToMarV and ToTV clearly separate from other plant picorna-like viruses and are likely to belong to the same yet unnamed new genus.

BRIEF DESCRIPTION OF THE FIGURES

The patent or application file contains at least one drawing executed in color. Copies of this patent or application publication with color drawing(s) will be provided by the Office upon request and payment of the necessary fee.

FIG. 5 shows the complete sequence of the ToTV-E01 RNA 2 molecule (SEQ ID NO:1).

FIG. 6 shows the complete sequence of the ToTV-E01 RNA 1 molecule (SEQ ID NO:2)

FIG. 8 shows the complete sequence of the PRI-TMarV0601 RNA 1 molecule (SEQ ID NO:15).

FIG. 9 shows the complete sequence of the PRI-TMarV0601 RNA 2 molecule (SEQ ID NO:16)

REFERENCES

Figure 1:
FIG. 1 shows a photograph of symptoms of the ToTV-disease on leaves of a tomato plant caused by ToTV-E01.
Figure 2:
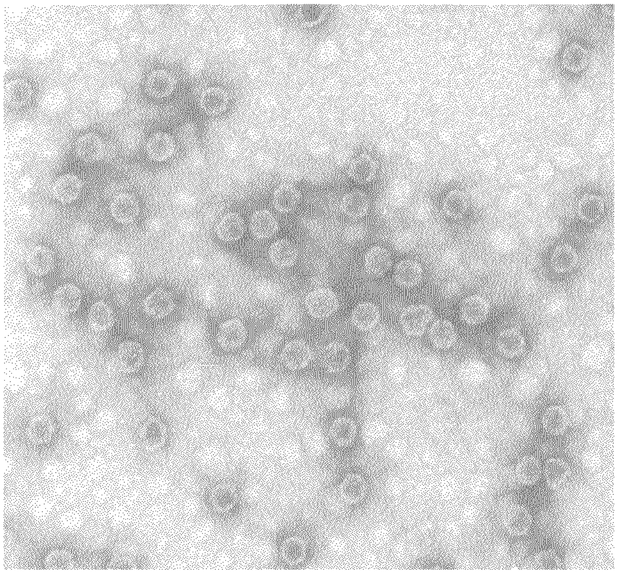
FIG. 2 shows an electron micrograph of purified ToTV-E01 particles. Particles are about 28 nm in diameter.
Figure 3:
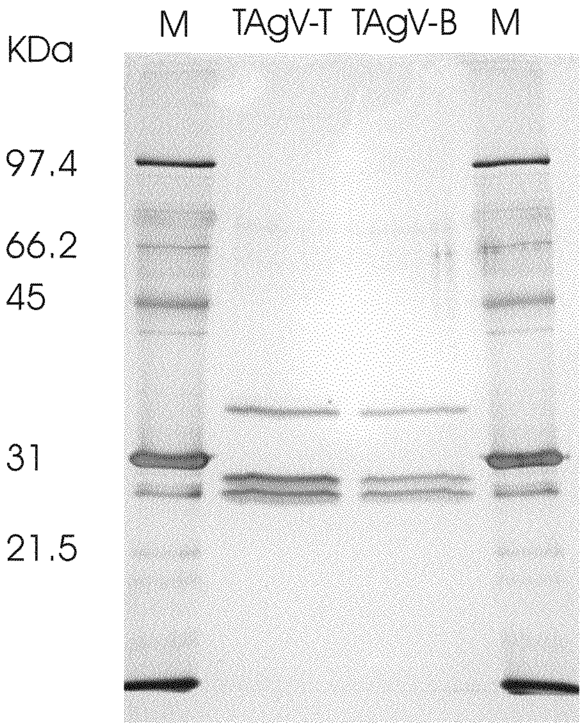
FIG. 3 shows the result of a silver-stained PAGE gel of purified ToTV-E01 virus top (TAgV-T) and bottom (TAgV-B) fractions indicating the three capsid proteins of approximately 23, 26 and 35 kDa.
Figure 4:
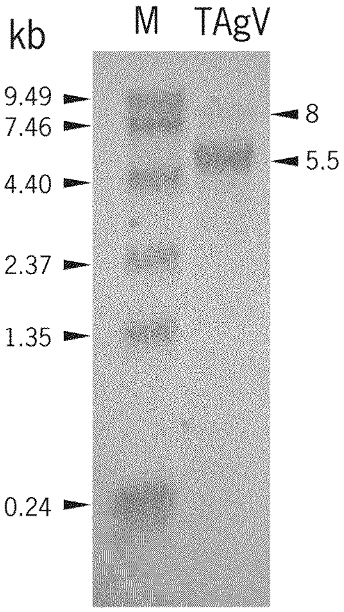
FIG. 4 shows the result of denaturing agarose gel electrophoresis. Sizes of the segments are indicated in kilobases (kb). The gel was stained using ortho-toluidine blue. M: molecular size standard. TAgV: 1 μg of isolated ToTV-E01 RNA.
Figure 7:
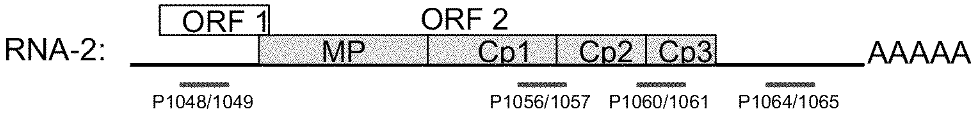
FIG. 7 shows the general structure of the ToTV-E01 virus indicating the site of annealing of the various primer sets as used in Example 2 to RNA 2.
Figure 10:
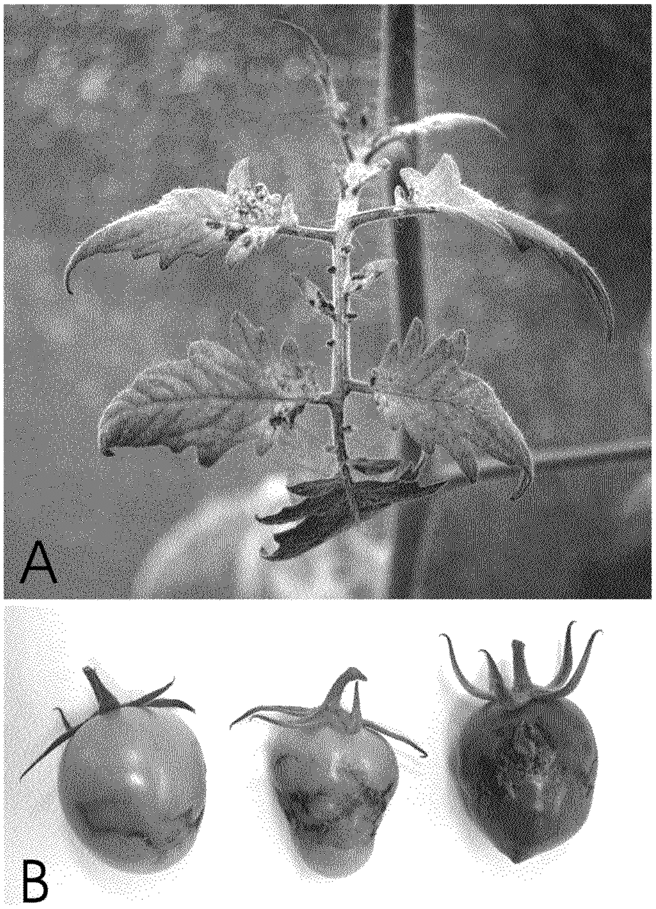
FIG. 10 shows the typical symptoms of tomato marchitez virus in A) tomato leaves: necrosis surrounded by a yellow or bright green area, beginning at the base of the leaflets, and B) tomato fruits: necrotic rings and patches.
Figure 11:
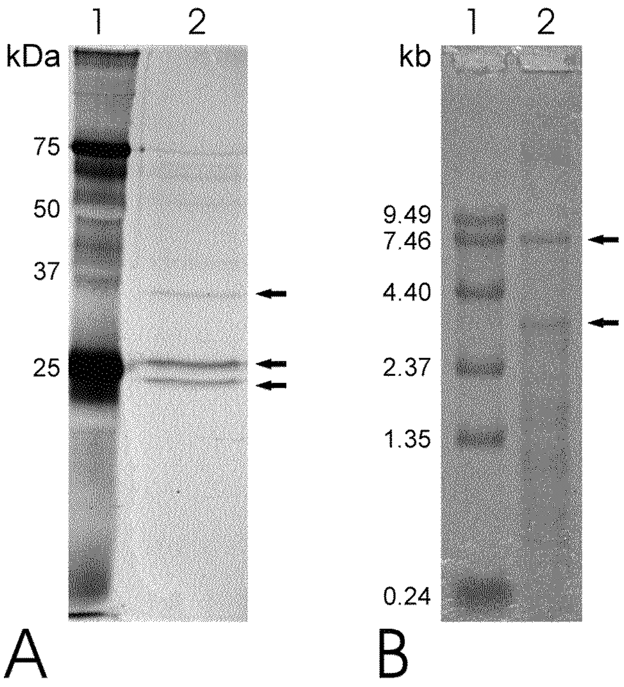
FIG. 11 shows in panel A) the result of denaturing polyacrylamide gel electrophoresis (SDS-PAGE) of ToMarV capsid proteins. Proteins were visualized by silver staining. 1) molecular weight markers (Bio-Rad Precision Plus Protein Standards (note: the prestained 37 kDa and 50 kDa standards do not stain in the used silver staining method), 2) ToMarV purified virions after $Cs_2SO_4$ buoyant density gradient centrifugation; in panel B) the result of denaturing agarose gel electrophoresis of RNA extracted from ToMarV virions and stained with ortho-toluidine blue. 1:molecular size standard (Invitrogen 0.24-9.5-kb RNA Ladder); 2: RNA purified from ToMarV virions. Arrows indicate positions of the ~3.5-kb and 7.5-kb RNA bands.
Figure 12:
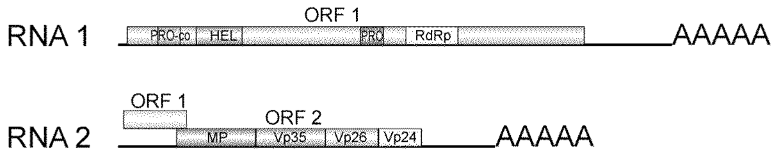
FIG. 12 shows the genome organization of ToMarV.
Figure 13:
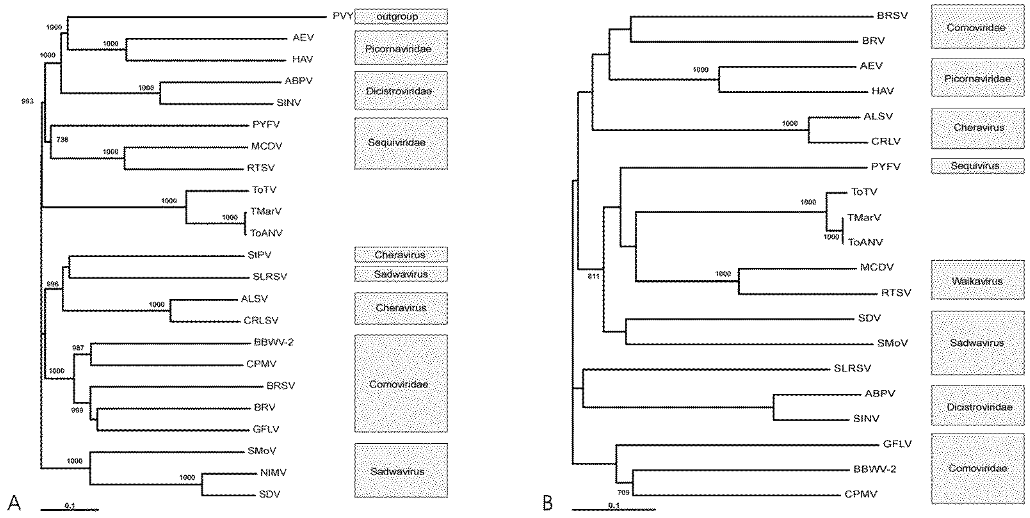
FIG. 13 shows a phylogenetic analysis of ToMarV (PRI-TMarV0601) and related viruses (e.g. ToTV-E01) based on the alignment of A) the region between the protease CG motif and GDD RdRp motif of RNA1; and B) the helicase region between motifs A and C of RNA1.

Altschul, S. F., Gish, W., Miller, W., Myers, E. W., Lipman, D. J. (1990). Basic local alignment search tool. *J. Mol. Biol.,* 215:403-410.

Altschul, S. F., Madden, T. L., Schaffer, A. A., Zhang, J., Zhang, Z., Miller, W., Lipman, D. J. (1997). Gapped BLAST and PSI-BLAST: A new generation of protein database search programs. *Nucl. Acids Res.,* 25, 3389-3402.

Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

Barany, F. (1991) Genetic disease detection and DNA amplification using cloned thermostable ligase. *Proc. Natl. Acad. Sci. USA* 88: 189-193.

Boom, R., Sol, C. J. A., Salimans, M. M. M., Jansen, C. L., Wertheim-van Dillen, P. M. E., Noordaa, van der J. (1990) Rapid and simple method for purification of nucleic acids. *J. Clin. Microbiol.* 28: 495-503.

Chomczynski, P., Sacchi, N. (1987) Single-step method of RNA isolation by acid guanidinium thiocyanate-phenol-chloroform extraction. *Anal. Bio.* 162:156-159.

Clark, M. F., Adams A. N. (1977) Characteristics of the microplate method of enzyme-linked immunosorbent assay for the detection plant viruses. *J. Gen. Virol.* 34:475-483.

Coligan, J. E., Kruisbeek, A. M., Margulies, D. H., Shevach, E. M. Strober, W. (Eds.) (1997) Current Protocols in Immunology. John Wiley & Sons Inc. Baltimore.

Compton, J. (1991) Nucleic acid sequence-based amplification. *Nature* 1991, 350:91-92.

Devereux, J., Haeberli, P., Smithies, O. (1984) A comprehensive set of sequence analysis programs for the VAX. *Nucleic Acids Res.* 12: 387-395.

Dijkstra, J., de Jager, C. (Eds.) (1998) Practical Plant Virology—Protocols and Exercises, Springer Duffus, J. E., Liu, H. Y., Wisler, G. C. (1996) Tomato infectious chlorosis virus—a new clostero-like virus transmitted by *Trialeurodes vaporariorum. European Journal of Plant Pathology,* 102(3), 219-226.

Felsenstein, J. 1989. PHYLIP—Phylogeny Inference Package (Version 3.2). *Cladistics* 5: 164-166.

Guatelli, J. C., Whitfield, K. M., Kwoh, D. Y., Barringer, K. J., Richman, D. D., Gingeras, T. R. (1990) Isothermal, in vitro amplification of nucleic acids by a mutienzyme reaction modeled after retroviral replication. *Proc. Natl. Acad. Sci. USA* 87:1874-1878.

Hagiwara, K., Ichiki, T. U., Ogawa, Y., Omura, T., Tsuda, S. (2002). A single amino acid substitution in 126-kDa protein of Pepper mild mottle virus associates with symptom attenuation in pepper; the complete nucleotide sequence of an attenuated strain, C-1421. *Arch Virol* 147:833-340.

Harlow, E. and Lane, D. (1988) Antibodies: A Laboratory Manual. Cold Spring Harbor Laboratory, Cold Spring Harbor, N.Y.

Hirata, H., Lu, X., Yamaji, Y., Kagiwada, S., Ugaki, M. Namba, S. (2003) A single silent substitution in the genome of Apple stem grooving virus causes symptom attenuation. *J Gen Virol* 84:2579-2583.

Jacobs M. V., Snijders P. J., van der Brule A. J. (1997) A general primer (GP5+/GP6+)-mediated PCR-enzyme immunoassay method for rapid detection of 14 high-risk and 8 low-risk human papillomavirus genotypes in cervical scrapings. *J Clin Microbiol* 35:791-795.

Katz, E., Eksteen, R., Schoenmakers, P., Miller, N. (eds.) (1998) Handbook of HPLC. Marcel Dekker, New York.

Kinter, M., Sherman, N. E. (2000) Protein Sequencing and Identification Using Tandem Mass Spectrometry. Wiley Interscience.

Koonin, E. V. (1991) The phylogeny of RNA-dependent RNA polymerases of positive-strand RNA viruses. *J Gen Virol* 72:2197-2206.

Kwoh, D. Y., Davis, G. R., Whitefield, K. M., Chappelle, H. L., DiMichele, L. J., Gingeras, T. R. (1989) Transcription-Based Amplification System and Detection of Amplified Human Immunodeficiency Virus Type 1 with a Bead-Based Sandwich Hybridization Format. *Proc. Natl. Acad. Sci. USA,* 86, 1173-1177.

Laemmli, U. K. (1970) Cleavage of structural proteins during the assembly of the head of bacteriophage T4. *Nature* 227, 680-685.

Lerner, R. A., Kang, A. S., Bain, J. D., Burton, D. R., Barbas, C. F. (1992) Antibodies without immunization. *Science* 258:1313-1314.

Lizardi, P. M., Guerra, C. E., Lomeli, H., Tussie-Luna, I., Kramer, F. R. (1988) Exponential amplification of recombinant RNA hybridization probes. *Biotechnology* 6, 1197-1202.

Lowman, H. B., Bass, S. H., Simpson, N., Wells, J. A. (1991) Selecting high-affinity binding proteins by monovalent phage display. *Biochem.* 30(45): 10832-8.

Lu, X., Hirata, H., Yamaji, Y., Ugaki, M., Namaba, S. (2001). Random mutagenesis in a plant viral genome using a DNA repair-deficient mutator *Escherichia coli* strain. *J Virol Methods* 94:37-43.

Marks, J. D., Hoogenboom, H. R., Griffiths, A. D., Winter, G. (1992a) Molecular evolution of proteins on filamentous phage. *Journal of Biological Chemistry,* 267, 16007-16010.

Marks, J. D., Griffiths, A. D., Malmqvist, M., Clackson, T. P., Bye, J. M. Winter, G. (1992b). By passing immunization: building high affinity human antibodies by chain shuffling. *Biotechnology* 10: 779:783.

Meinkoth J., Wahl G. (1984) Hybridization of nucleic acids immobilized on solid supports. *Anal Biochem,* 138(2):267-284.

Mullis, K. B., Faloona, F. A. (1987) Specific synthesis of DNA in vitro via a polymerasecatalyzed chain reaction. *Meth. Enzymol.* 155:335-350.

Pierik, R. L. M. (1999) In vitro Culture of Higher Plants, 4th edition, 360 pages, ISBN: 0-7923-5267-X.

Rose, N., DeMacrio, E., Fahey, J., Friedman, H., Penn, G. (1997) Manual of Clinical Laboratory Immunology. American Soc. Microbiology Press, Washington, D.C.

Sambrook, J., Russell D. W., Sambrook, J. (2001) Molecular Cloning: a Laboratory Manual. Cold Spring Harbor Laboratory Press, Plainview, N.Y.

Sanger, F., Nicklen, S., Coulson, A. R. (1977) DNA sequencing with chain-terminating inhibitors. *Proc. Natl. Acad. Sci. U.S.A.* 74; 5463-5467.

Schagger H., von Jagow, G. (1987) Tricine-sodium dodecyl sulfate-polyacrylamide gel electrophoresis for the separation of proteins in the range from 1 to 100 kDa. *Analytical Biochemistry* 166, 368-379.

Smith, L. M., Sanders, J. Z., Kaiser, R. J., Hughs, P., Dodd, C., Connell, C. R., Heins, C., Kent, S. B. H., Hood, L. E. (1986) Fluorescent detection in automated DNA sequence analysis. *Nature* 321:673-681.

Swofford, D. L. (2000). PAUP*: phylogenetic analysis using parsimony (*and other methods). 4th edition. Sinauer Associates, Sunderland, Mass.

Takeshita, M., Suzuki, M., Takanami, Y. (2001). Combination of amino acids in the 3a protein and the coat protein of Cucumber mosaic virus determines symptom expression and viral spread in bottle gourd. *Arch Virol* 146:697-711.

Thompson, J. D., Gibson, T. J., Plewniak, F., Jeanmougin, F., Higgins, D. G. (1997) The ClustalX windows interface: flexible strategies for multiple sequence alignment aided by quality analysis tools. *Nucleic Acids Research,* 24:4876-4882.

Thompson, J. R., Perry, K. L., De Jong, W. (2004a) A new potato virus in a new lineage of picorna-like viruses. *Arch Virol.* 149:2141-2154.

Thompson, J. R., Perry, K. L., De Jong, W. (2004b) The characterization of a new picorna-like virus infecting tomato. Abstract book of the 23rd Annual Meeting of the American Society for Virology, Montreal, Canada, July 2004.

Tijssen, P. 1993. Laboratory Techniques in Biochemistry and Molecular Biology-Hybridization with Nucleic Acid Probes, Part I, Chapter 2 "Overview of principles of hybridization and the strategy of nucleic acid probe assays", Elsevier. N.Y.

Van den Brule, A. J. C., Pol, R., Fransen-Daalmeijer, N., Schouls, L. M., Meijer, C. J. L. M., Snijders, P. J. F. (2002) GPS+/6+ PCR followed by Reverse Line Blot Analysis Enables Rapid and High-Throughput Identification of Human Papillomavirus Genotypes. *J. Clin. Microbiol.* 40:779-787.

Vela, C., Cambra, M., Cortés, E., Moreno, P., Miguet, J. G., Pérez de San Roman, C., Sanz, A. (1986) Production and characterization of monoclonal antibodies specific for citrus tristeza virus and their use for diagnosis. *J. Gen. Virol.* 67:91-96.

Walker, G. T., Fraiser, M. S., Schram, J. L., Little, M. C., Nadeau, J. G., Malinowski, D. P. (1992) Strand displacement amplification—an isothermal, in vitro DNA amplification technique *Nucleic Acids Res* 20:1691-1696.

Walker, J. M. 2004. PCR Protocols on CD. Humana Press.

Wisler, G. C., Li, R. H., Liu, H. Y., Lowry, D. S., Duffus, J. E. (1998) Tomato chlorosis virus: a new whitefly-transmitted, phloem-limited, bipartite closterovirus of tomato. *Phytopathology,* 88(5), 402-409.

Young R. A., Davis, R. W. (1983) Efficient isolation of genes using antibody probes. *Proc. Natl. Acad. Sci. U.S.A.* 80:1194-1198.

What is claimed:

1. A method for identifying a plant that is resistant to i) a plant virus named Tomato Marchitez virus (ToMarV), deposited under depositors reference PRI-TMarV0601 on Jul. 10, 2007 with the Deutsche Sammlung von Mikroorganismen and Zellkulturen GmbH, in Braunschweig, Germany, the deposited material receiving the accession number DSM 19656, or ii) a Tomato Marchitez virus comprising at least one nucleic acid sequence selected from the group consisting of SEQ ID NO: 16 and a sequence having a nucleotide sequence homology of at least 80% thereto, said virus having isometric virus particles with a diameter of approximately 28 nm, having a viral genome consisting of two (+) ssRNA molecules of about 7.2 kb (RNA1) and about 4.9 kb (RNA2), wherein the viral capsid contains three coat proteins of approximately 35, 26 and 24 kDa, respectively, and wherein the virus induces severe leaf necrosis in tomato plants, beginning at the base of the leaflets, and necrotic rings on tomato fruits, the method comprising the steps of:

a) exposing a plant or plant part to an infective dosage of the virus by mechanical inoculation of virus particles or virus nucleic acid on plants, and b) identifying said plant as a resistant plant when, after said exposure, either disease-symptoms in said plant or plant part remain absent or are delayed in expression or are at least reduced in severity or are localized relative to a susceptible control plant, and/or the virus or genomic sequences thereof are not present in said plant or plant part or the presence of the virus is at least quantitatively reduced relative to a susceptible control plant.

2. The method according to claim 1, wherein, in step b), the presence of the virus in said plant or plant part is determined by determining in a sample the presence of the virus or component thereof by reacting said sample with a polynucleotide capable of hybridizing under stringent conditions to a nucleic acid sequence selected from the group consisting of: SEQ ID NO: 16, a sequence having a nucleotide sequence homology of at least 80% to SEQ ID NO: 16, or their complementary strands and fragments thereof; or by reacting said sample with an antibody specifically directed against an antigen comprising an isolated or recombinant polypeptide obtainable from a virus named Tomato Marchitez virus (ToMarV), deposited under depositors reference PRI-TMarV0601 on Jul. 10, 2007 with the Deutsche Sammlung von Mikroorganismen and Zellkulturen GmbH, in Braunschweig, Germany, the deposited material receiving the accession number DSM 19656.

3. The method of claim 1 wherein the virus comprises SEQ ID NO: 16 or a sequence having a nucleotide sequence homology of at least 90% thereto.

4. The method of claim 1 wherein the virus comprises SEQ ID NO: 16 or a sequence having a nucleotide sequence homology of at least 95% thereto.

5. The method of claim 1 wherein the virus comprises SEQ ID NO: 16 or a sequence having a nucleotide sequence homology of at least 98% thereto.

6. The method of claim 1 wherein the virus comprises SEQ ID NO: 16 or a sequence having a nucleotide sequence homology of at least 99% thereto.

7. The method according to claim 1, wherein, in step b), the presence of the virus in said plant or plant part is determined by determining in a sample the presence of the virus or component thereof by reacting said sample with a polynucleotide capable of hybridizing under stringent conditions to SEQ ID NO: 16, a sequence having a nucleotide sequence homology of at least 90% to SEQ ID NO: 16, or their complementary strands and fragments thereof or an antibody specifically directed against an antigen comprising an isolated or recombinant polypeptide obtainable from a virus named Tomato Marchitez virus (ToMarV), deposited under depositors reference PRI-TMarV0601 on Jul. 10, 2007 with the Deutsche Sammlung von Mikroorganismen und Zellkulturen GmbH, in Braunschweig, Germany, the deposited material receiving the accession number DSM 19656 or a fragment thereof.

8. The method according to claim 1, wherein, in step b), the presence of the virus in said plant or plant part is determined by determining in a sample the presence of the virus or component thereof by reacting said sample with a polynucleotide capable of hybridizing under stringent conditions to SEQ ID NO:16, a sequence having a nucleotide sequence homology of at least 95% to SEQ ID NO:16, or their complementary strands and fragments thereof or an antibody specifically directed against an antigen comprising an isolated or recombinant polypeptide obtainable from a virus named Tomato Marchitez virus (ToMarV), deposited under depositors reference PRI-TmarV0601 on Jul. 10, 2007 with the Deutsche Sammlung von Mikroorganismen und Zellkulturen GmbH, in Braunschweig, Germany, the deposited material receiving the accession number DSM 19656 or a fragment thereof.

9. The method according to claim 1, wherein, in step b), the presence of the virus in said plant or plant part is determined by determining in a sample the presence of the virus or component thereof by reacting said sample with a polynucleotide capable of hybridizing under stringent conditions to SEQ ID NO:16, a sequence having a nucleotide sequence homology of at least 99% to SEQ ID NO:16, or their complementary strands and fragments thereof or an antibody specifically directed against an antigen comprising an isolated or recombinant polypeptide obtainable from a virus named Tomato Marchitez virus (ToMarV), deposited under depositors reference PRI-TmarV0601 on Jul. 10, 2007 with the Deutsche Sammlung von Mikroorganismen und Zellkulturen GmbH, in Braunschweig, Germany, the deposited material receiving the accession number DSM 19656 or a fragment thereof.

* * * * *

UNITED STATES PATENT AND TRADEMARK OFFICE

CERTIFICATE OF CORRECTION

PATENT NO. : 9,080,142 B2
APPLICATION NO. : 12/631259
DATED : July 14, 2015
INVENTOR(S) : van den Heuvel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 915 days.

Signed and Sealed this
Twenty-first Day of June, 2016

Michelle K. Lee
*Director of the United States Patent and Trademark Office*